(12) United States Patent
Choi et al.

(10) Patent No.: US 11,629,155 B2
(45) Date of Patent: Apr. 18, 2023

(54) SMALL MOLECULE ANTAGONIST COMPOUND TAC5 SERIES HAVING TOLL-LIKE RECEPTOR 3/7/8/9 INHIBITORY FUNCTION

(71) Applicant: AJOU UNIVERSITY INDUSTRY-ACADEMIC COOPERATION FOUNDATION, Suwon-si (KR)

(72) Inventors: Sangdon Choi, Suwon-si (KR); Eunha Kim, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 72 days.

(21) Appl. No.: 17/057,967

(22) PCT Filed: May 20, 2019

(86) PCT No.: PCT/KR2019/005978
§ 371 (c)(1),
(2) Date: Nov. 23, 2020

(87) PCT Pub. No.: WO2019/225920
PCT Pub. Date: Nov. 28, 2019

(65) Prior Publication Data
US 2021/0214372 A1    Jul. 15, 2021

(30) Foreign Application Priority Data
May 23, 2018  (KR) .................. 10-2018-0058503
Sep. 10, 2018  (KR) .................. 10-2018-0107638

(51) Int. Cl.
*C07D 498/04*  (2006.01)
*C07D 213/72*  (2006.01)
*C07D 401/04*  (2006.01)

(52) U.S. Cl.
CPC ......... *C07D 498/04* (2013.01); *C07D 213/72* (2013.01); *C07D 401/04* (2013.01)

(58) Field of Classification Search
CPC ... C07D 498/04; C07D 213/72; C07D 401/04
See application file for complete search history.

(56) References Cited

FOREIGN PATENT DOCUMENTS

| WO | 2004/004720 A1 | 1/2004 | |
|---|---|---|---|
| WO | 2005/002673 A1 | 1/2005 | |
| WO | 2009/044160 A1 | 4/2009 | |
| WO | 2017/141927 A1 | 8/2017 | |
| WO | WO-2019174601 A1 * | 9/2019 | ............. A61K 31/44 |

OTHER PUBLICATIONS

Bristol; Synthesis 1981,971-973. DOI: 10.1055/S-1981-29663 (Year: 1981).*
Connolly; Current Opinion in Pharmacology 2012, 12, 510-518. http://dx.doi.org/10.1016/j.coph.2012.06.002 (Year: 2012).*
Gao; Front. Physiol. 2017, 8, 508. https://doi.org/10.3389/fphys.2017.00508 (Year: 2017).*
Patra; Expert Opinion on Therapeutic Patents 2016, 26, 719-730. https://doi.org/10.1080/13543776.2016.1185415 (Year: 2016).*
Scarbaci; ChemMedChem 2014, 9, 1801-1816. https://doi.org/10.1002/cmdc.201402075 (Year: 2014).*
Chemical Abstracts STN Registry Database, Record for RN 1822820-53-0, "1-[3-(Phenylmethoxy)-2-pyridinyl]-1H-pyrazole-4-carbonitrile", Entered STN Dec. 4, 2015. (Year: 2015).*
Honghua Rao et al.,. "Copper-Catalyzed Arylation of Amines Using Diphenyl Pyrrolidine-2-phosphonate as the New Ligand", The Journal of Organic Chemistry. 2005, pp. 8107-8109, vol. 70.
Osamu Takeuchi et al., "Cutting Edge: Role of Toll-Like Receptor 1 in Mediating Immune Response to Microbial Lipoproteins", The Journal of Immunology, 2002, pp. 10-14, vol. 169.
Osamu Takeuchi et al., "Discrimination of bacterial lipoproteins by Toll-like receptor 6", International Immunology 2001, pp. 933-940, vol. 13, No. 7.
Alexander Poltorak et al., "Defective LPS Signaling in C3H/HeJ and C57BL/10ScCr Mice Mutations in Tlr4 Gene", Science, Dec. 11, 1998, pp. 2085-2088, vol. 282.
Sandra S. Diebold et al., "Innate Antiviral Responses by Means of TLR7-Mediated Recognition of Single-stranded RNA", Science, Mar. 5, 2004, pp. 1529-1531, vol. 303.
Florian Heil et al., "Species-Specific Recognition of Single-Stranded RNA via Toll-like Receptor 7 and 8", Science, Mar. 5, 2004, pp. 1526-1529, vol. 303.
Hiroaki Hemmi et al., "A Toll-like receptor recognizes bacterial DNA", Nature, Dec. 7, 2000, pp. 740-745, vol. 408.
Shizuo Akira et al., "Toll-Like Receptor Signalling", Nature Reviews Immunology, Jul. 2004, pp. 499-511, vol. 4.
Hiroaki Hemmi et al., "Small anti-viral compounds activate immune cells via the TLR7 MyD88-dependent signaling pathway", Nature Immunol, Feb. 2002, pp. 196-200, vol. 3, No. 2.

(Continued)

*Primary Examiner* — Daniel R Carcanague
(74) *Attorney, Agent, or Firm* — Sughrue Mion, PLLC

(57) ABSTRACT

A small molecule antagonist compound having a toll-like receptor 3/7/8/9 inhibitory function and its use in inhibiting TLR7, TLR8, TLR9 and TLR3 are disclosed. A novel compound expressed by TAC5 and TAC5-a, TAC5-c, TAC5-d or TAC5-e which are derivatives thereof not only prevents TNFα secretion, NFkB activation, IkB degradation and MAPKs phosphorylation induced by poly(I:C) (TLR3 agonist), IMQ (TLR7 agonist), CL075 (TLR7/8 agonist), R848 (TLR7/8 agonist), TL8 (TLR8 agonist) or CpG ODN (TLR9 agonist), but also inhibits generation of inflammatory cytokine, and thus is highly advantageous for preventive or therapeutic use for TLR3/7/8/9-related autoimmune diseases and inflammatory diseases including systemic lupus erythematosus, psoriasis and the like.

5 Claims, 38 Drawing Sheets
Specification includes a Sequence Listing.

(56) References Cited

OTHER PUBLICATIONS

Oliver Demaria et al., "TLR8 deficiency leads to autoimmunity in mice", The Journal of Clinical Investigation, Oct. 2010, pp. 3651-3662, vol. 120, No. 10.

Fabien B. Vincent et al., "The BAFF/APRIL system in SLE pathogenesis", Nature Reviews Rheumatology, Jun. 2014, pp. 365-373, vol. 10.

Arthur M. Krieg et al., "Toll-like receptor 7, 8 and 9: linking innate immunity to autoimmunity", Immunol Review, 2007, pp. 251-269, vol. 220.

Dorothea Terhorst et al., "Dynamics and Transcriptomics of Skin Dendritic Cells and Macrophages in an Imiquimod-Induced, Biphasic Mouse Model of Psoriasis", The Journal of Immunology, 2015, pp. 4953-4961, vol. 195.

Keith K. B. Gorden et al., "Oligodeoxynucleotides Differentially Modulate Activation of TLR7 and TLR8 by Imidazoquinolines", The Journal of Immunology, 2006, pp. 8164-8170, vol. 177.

Marion Jurk et al., "Modulating responsiveness of human TLR7 and 8 to small molecule ligands with T-rich phosphorothiate oligodeoxynucleotides", Eur. J. Immunol, 2006, pp. 1815-1826, vol. 36.

International Search Report for PCT/KR2019/005978 dated Aug. 16, 2019 [PCT/ISA/210].

\* cited by examiner

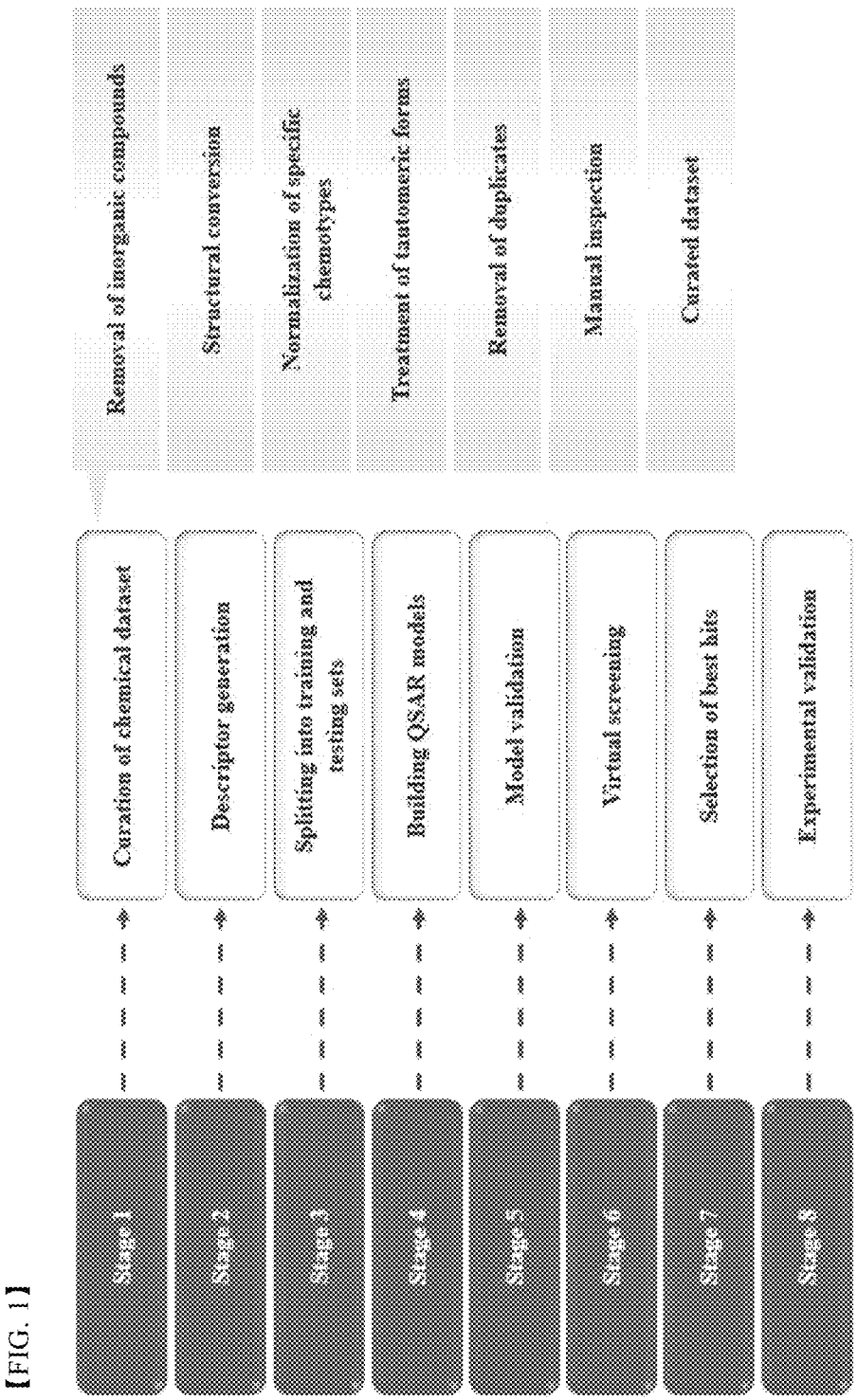
[FIG. 1]

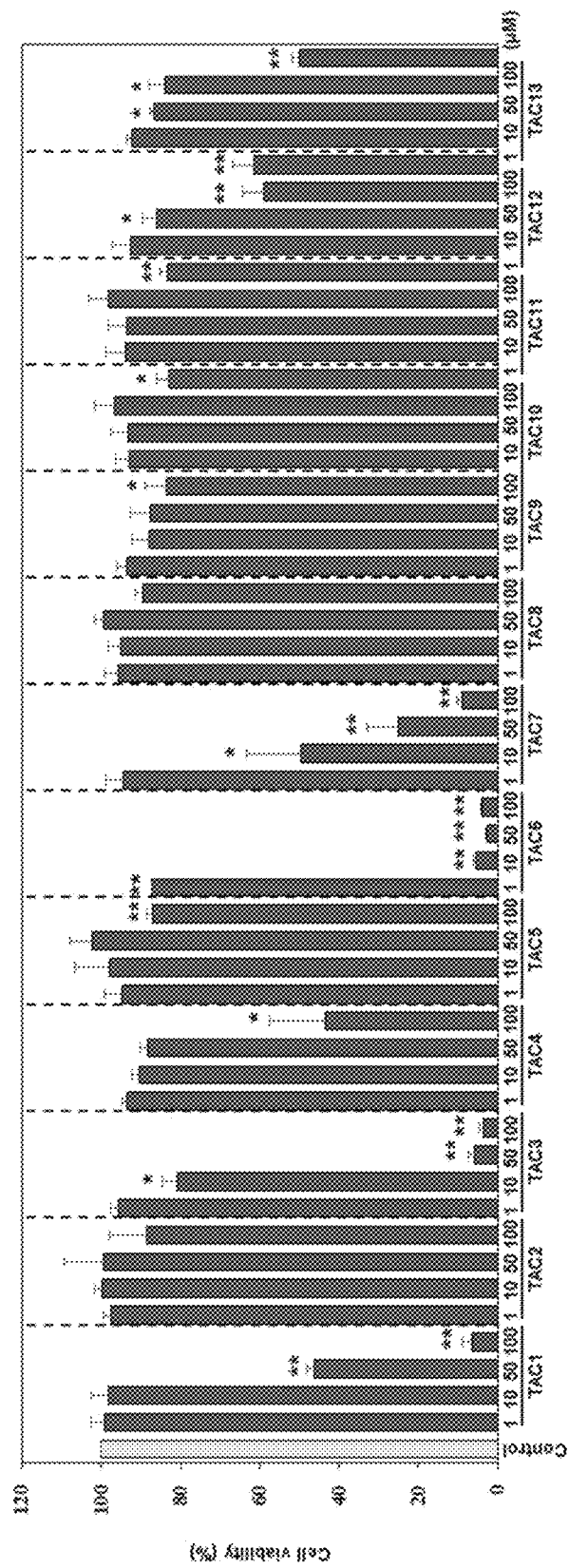
[FIG. 2A]

[FIG. 2B]
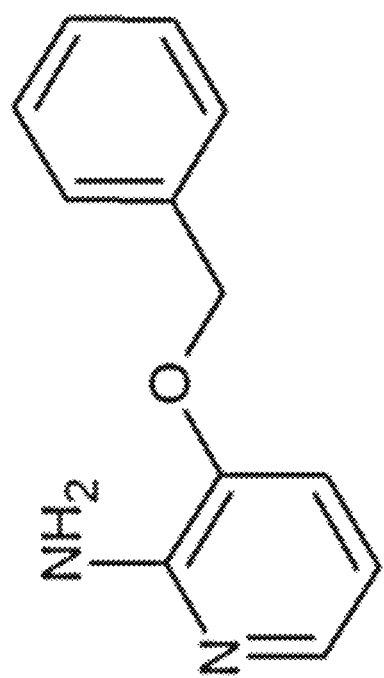
TAC5: 2-amino-3-benzyloxypyridine

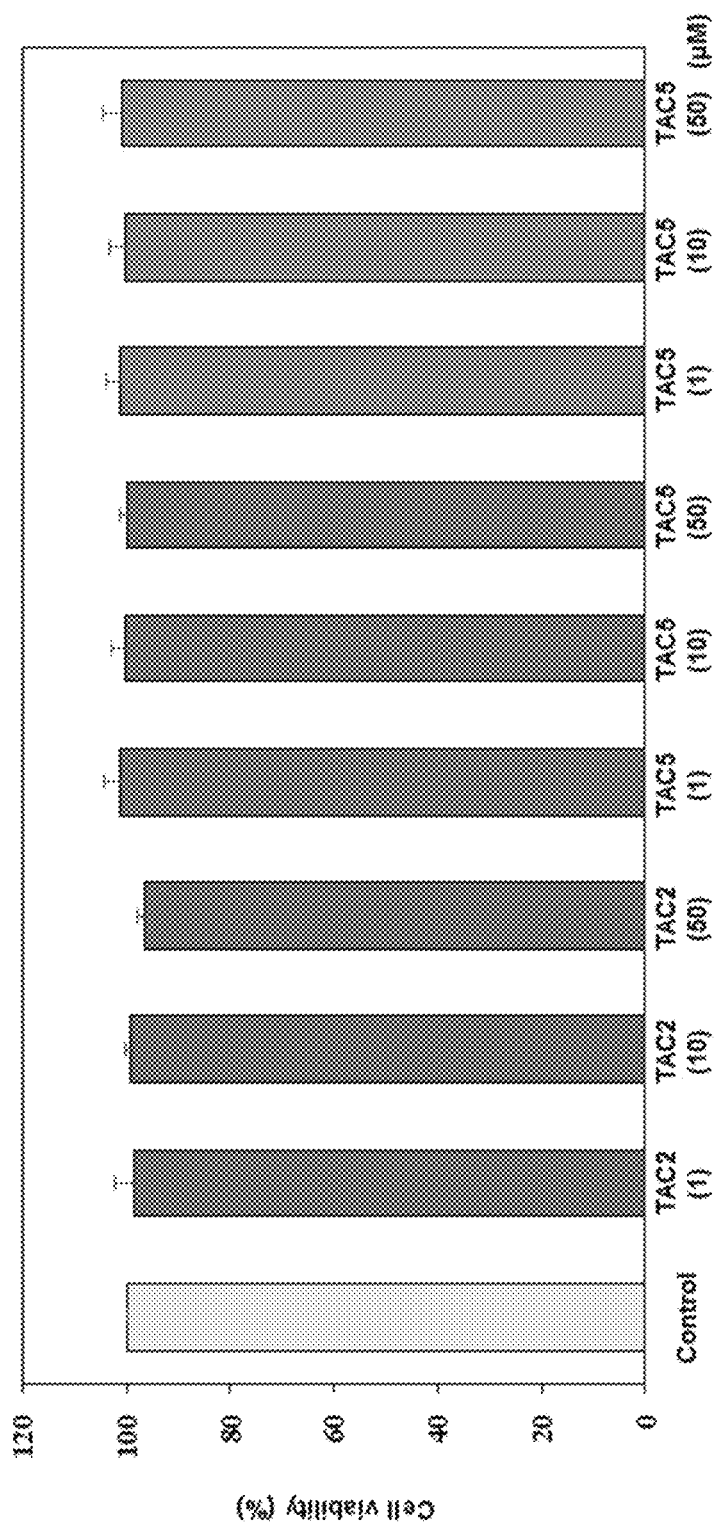
[FIG. 2C]

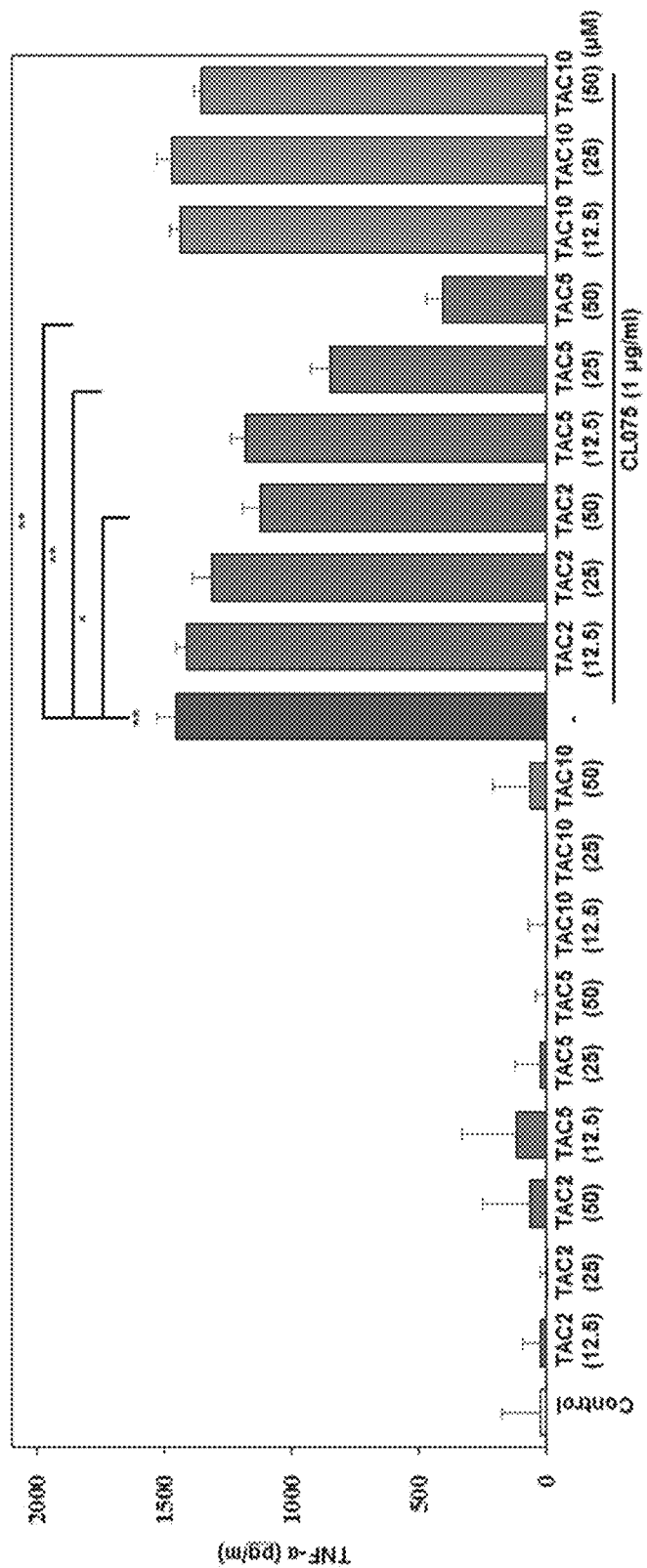
[FIG. 2D]

[FIG. 3A]
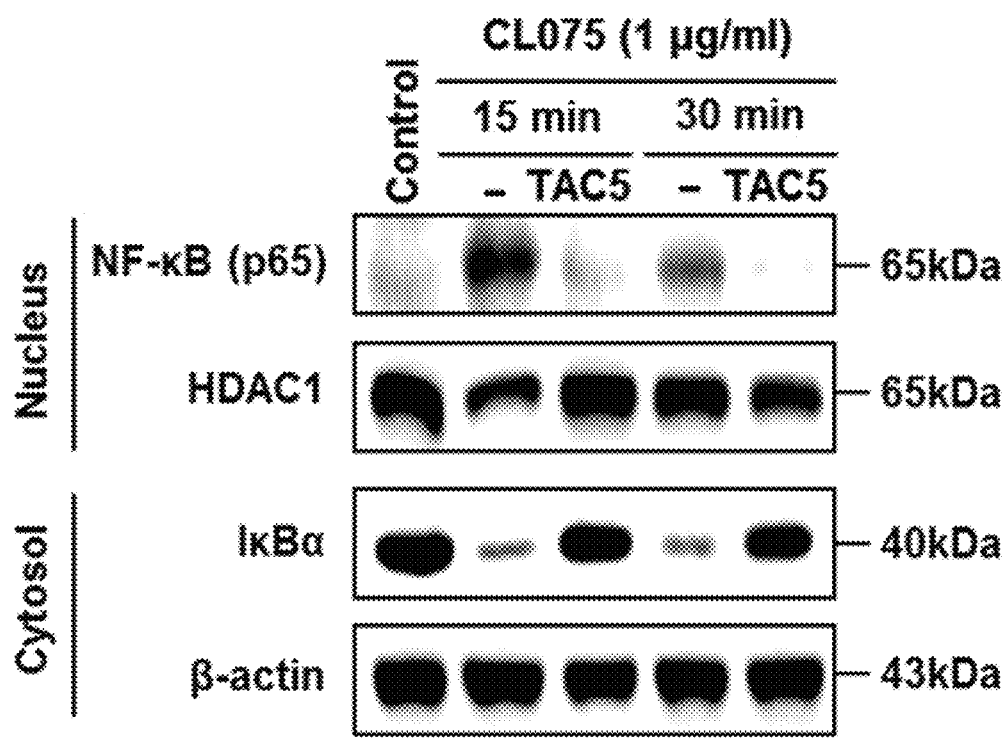

[FIG. 3B]
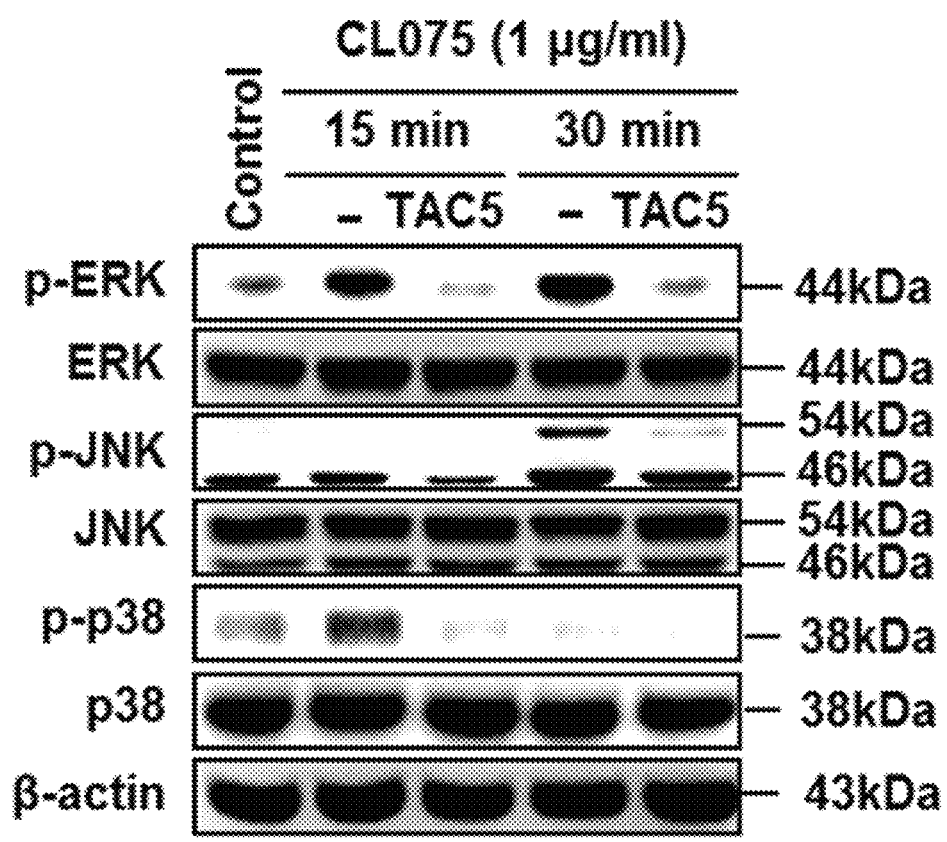

[FIG. 3C]
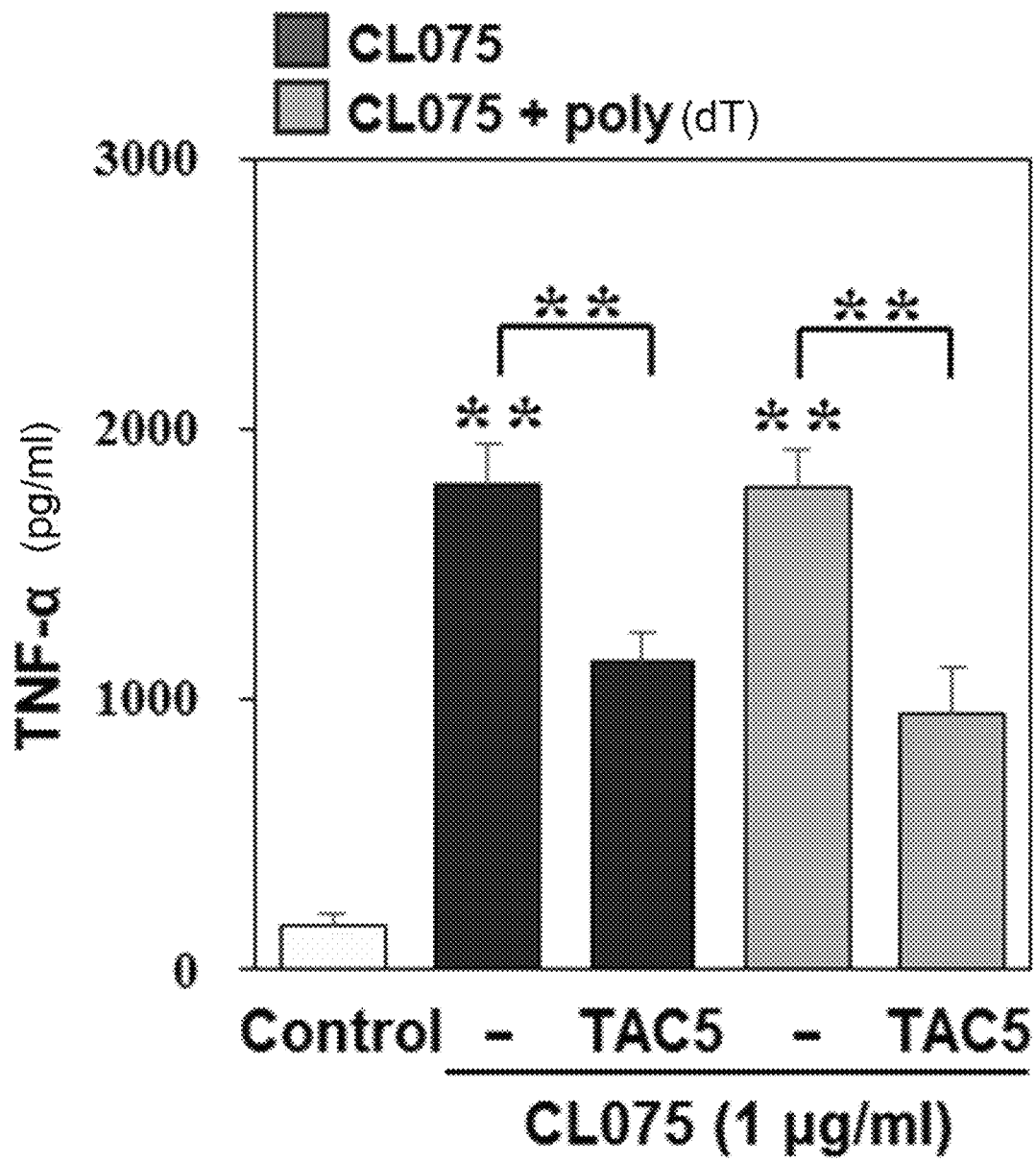

[FIG. 3D]
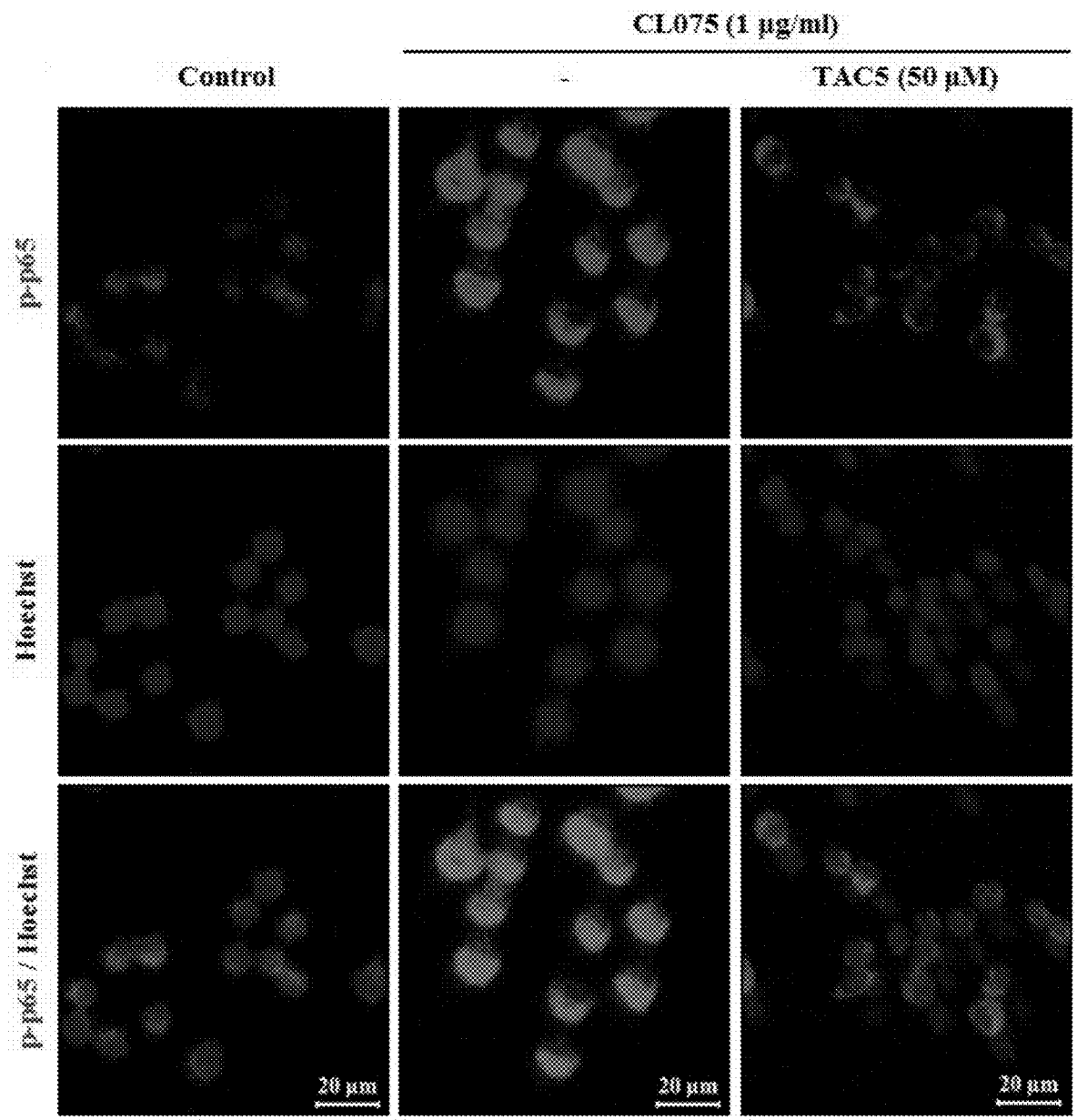

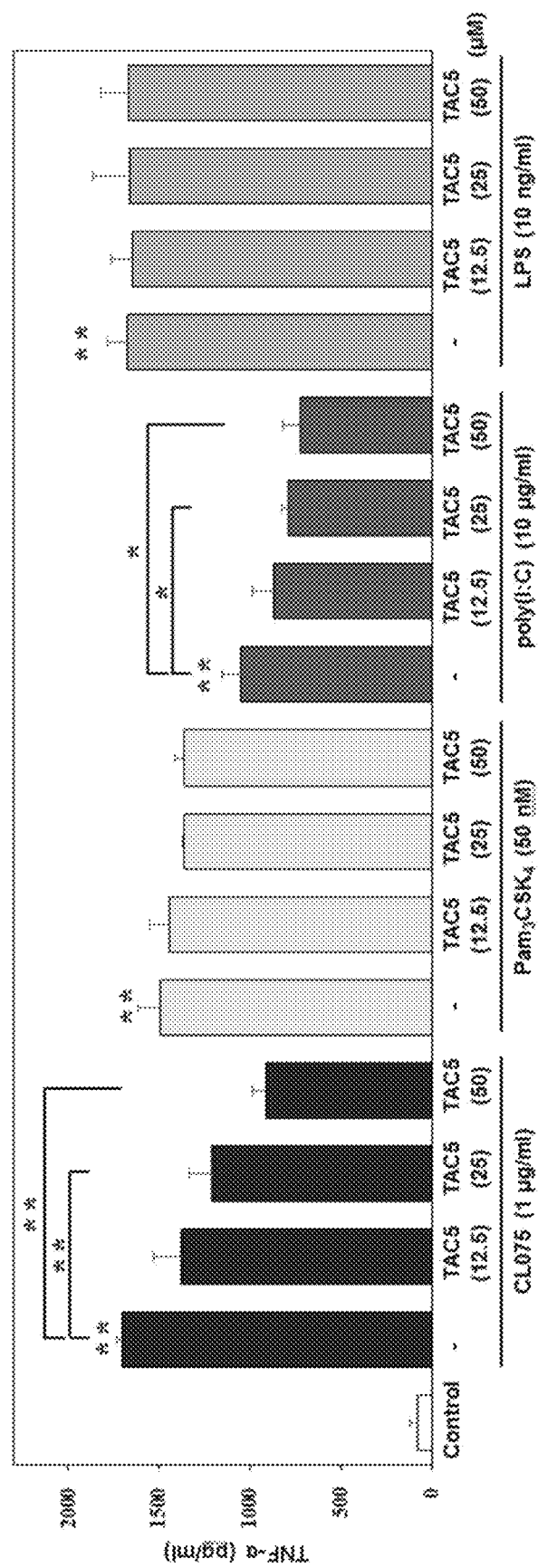
[FIG. 3E]

[FIG. 4A]
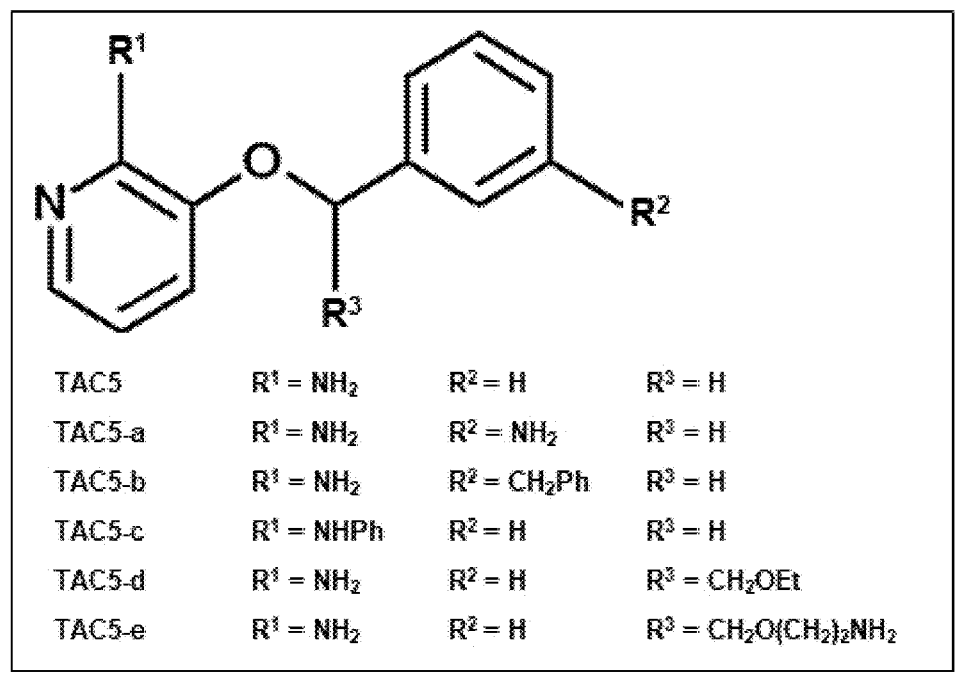

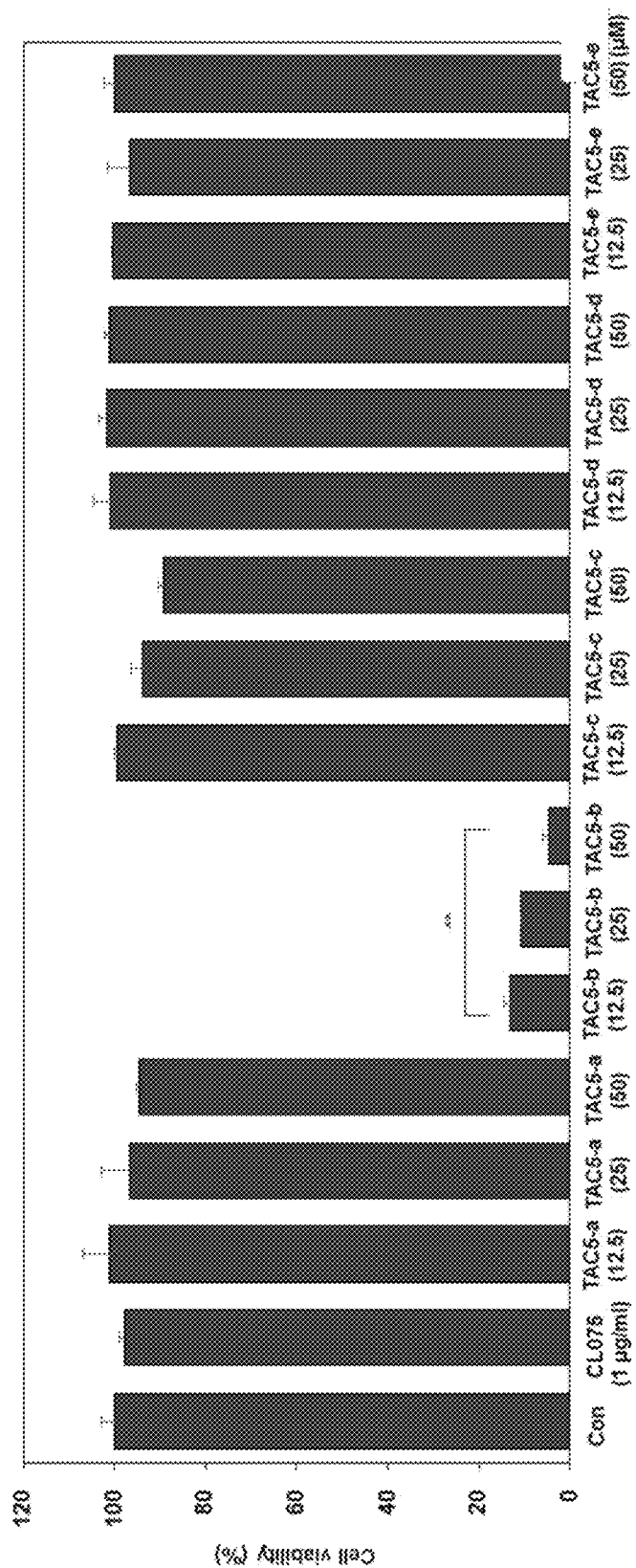
[FIG. 4B]

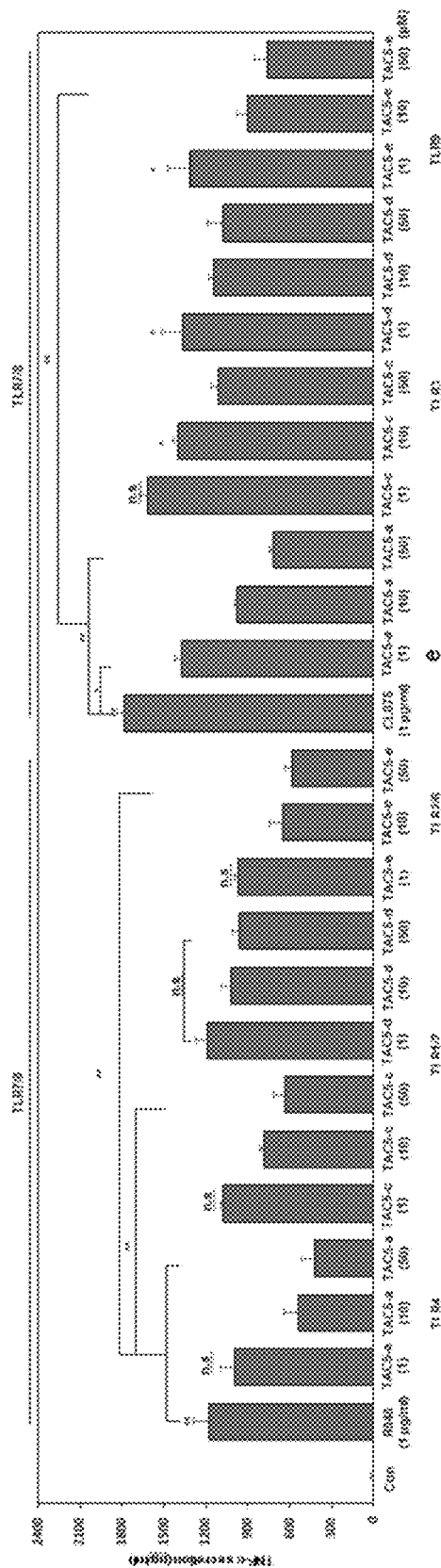
[FIG. 4C]

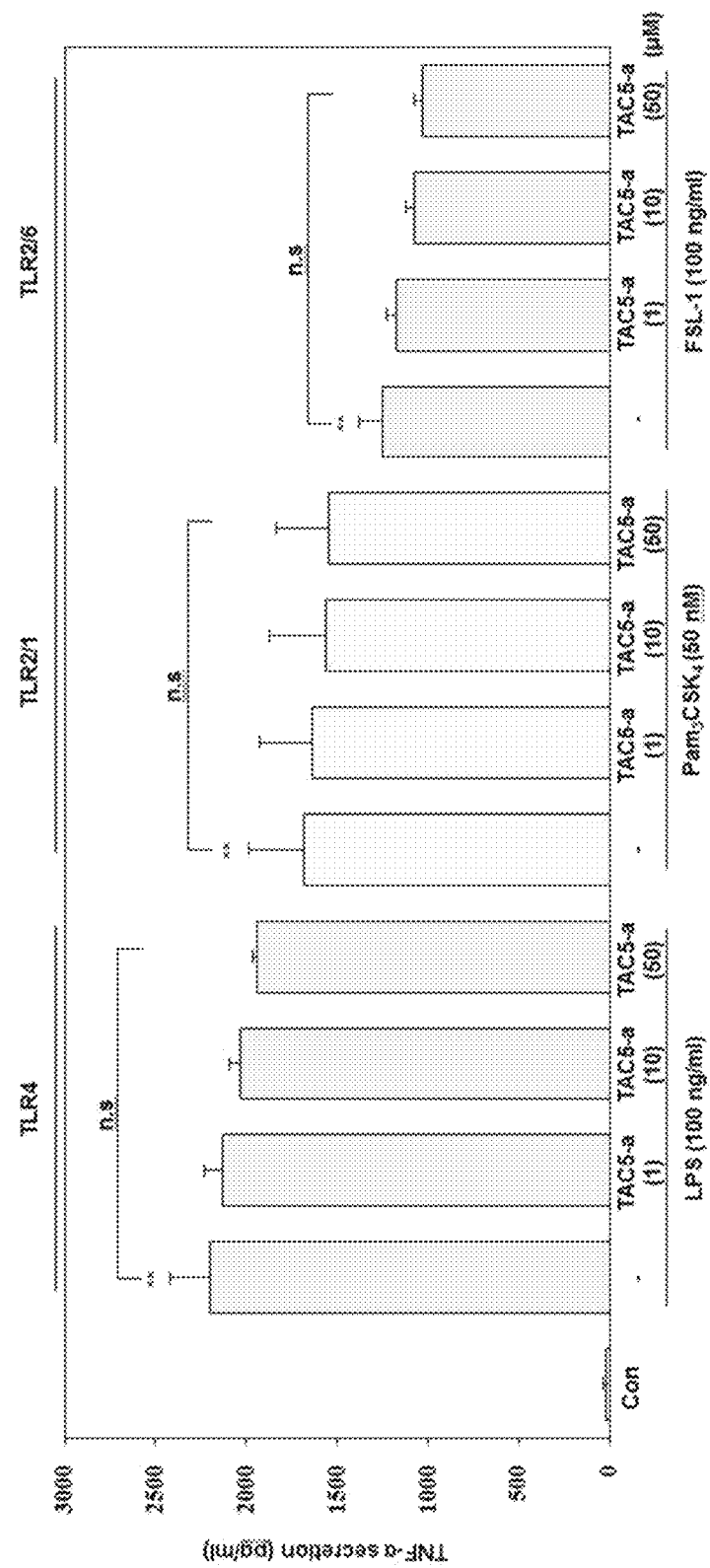
[FIG. 4D]

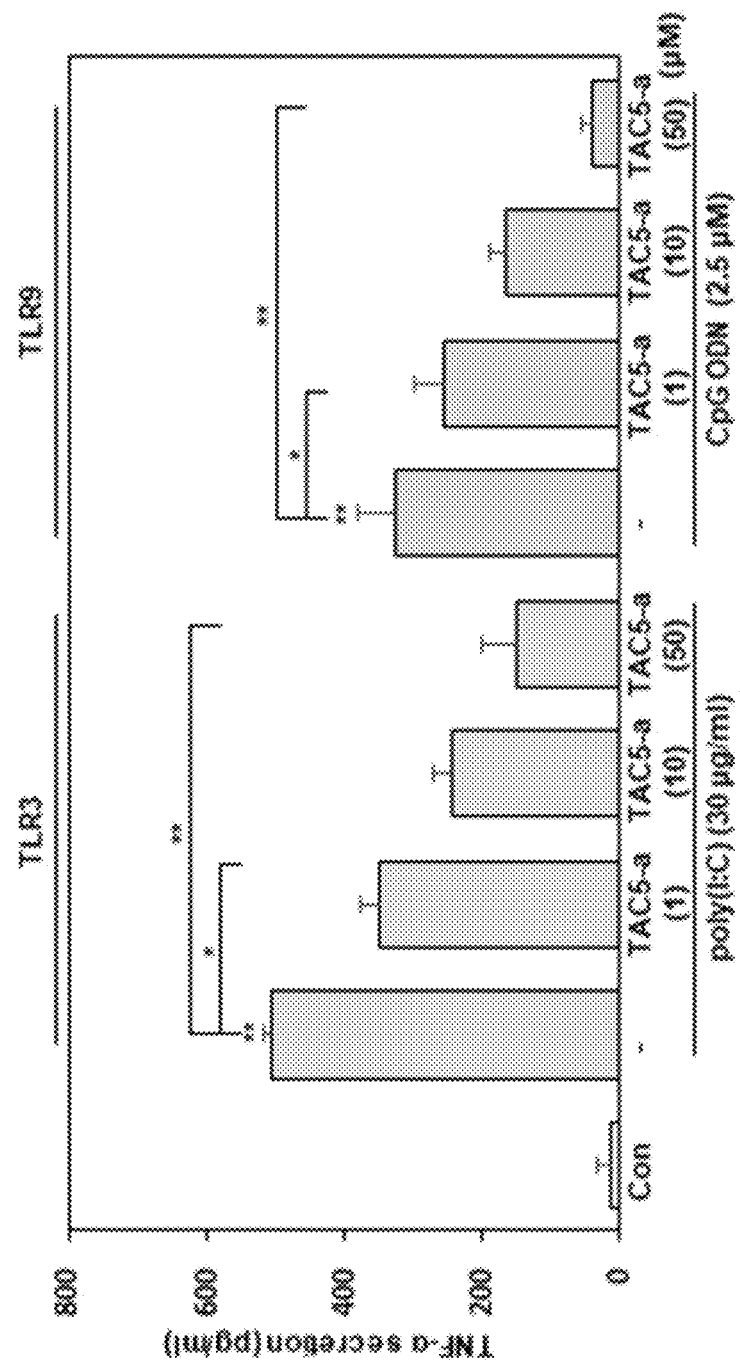
[FIG. 4E]

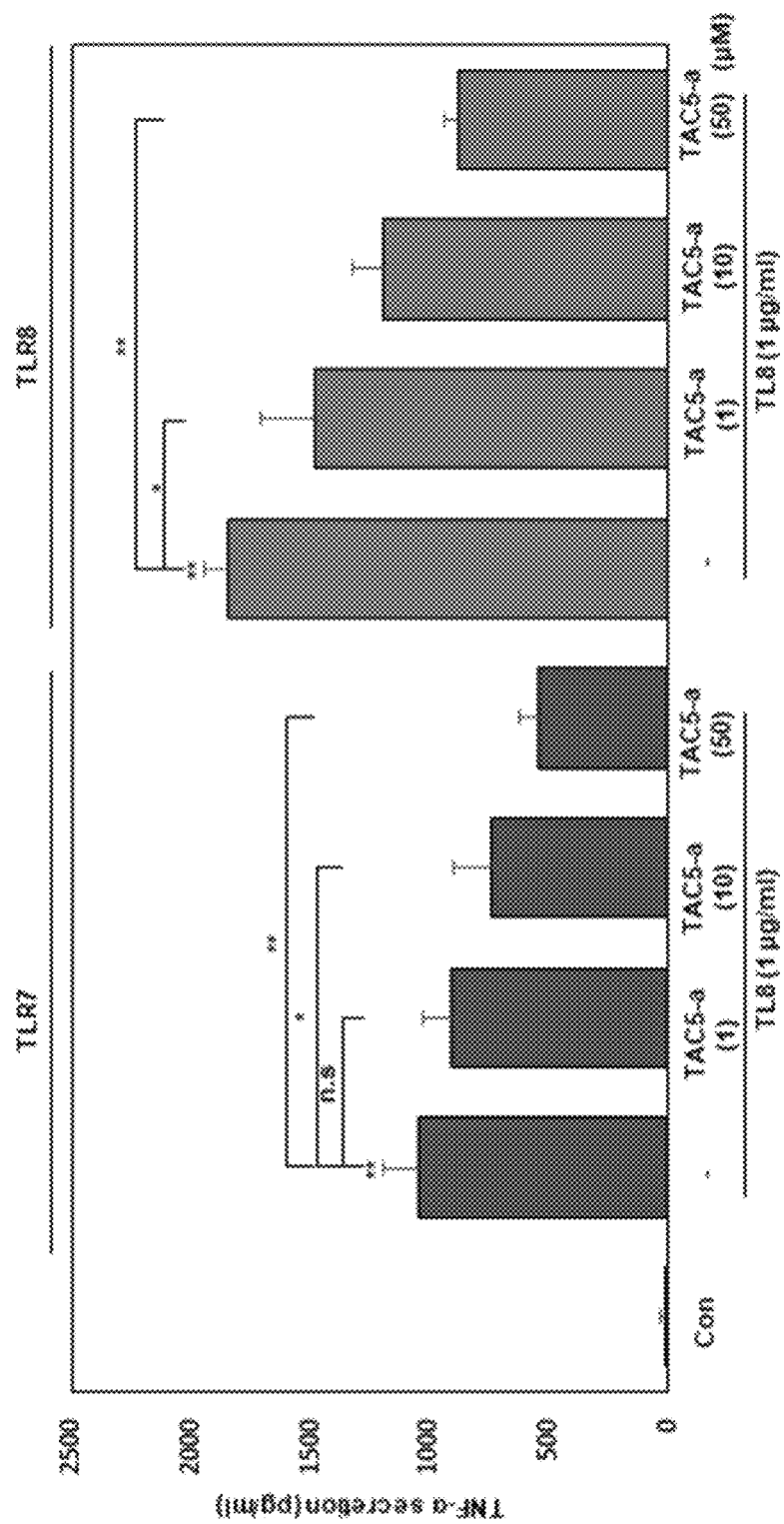
[FIG. 4F]

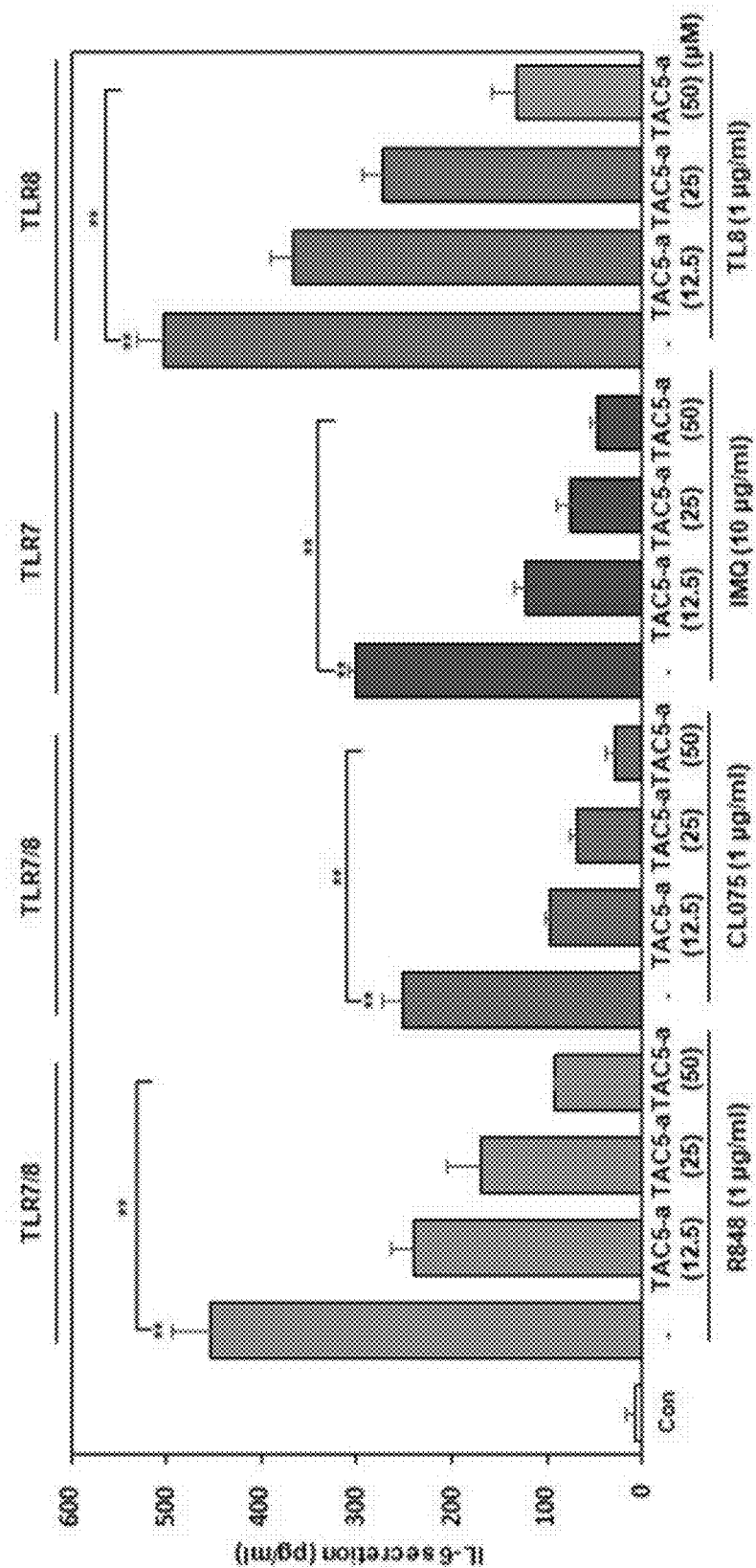
[FIG. 4G]

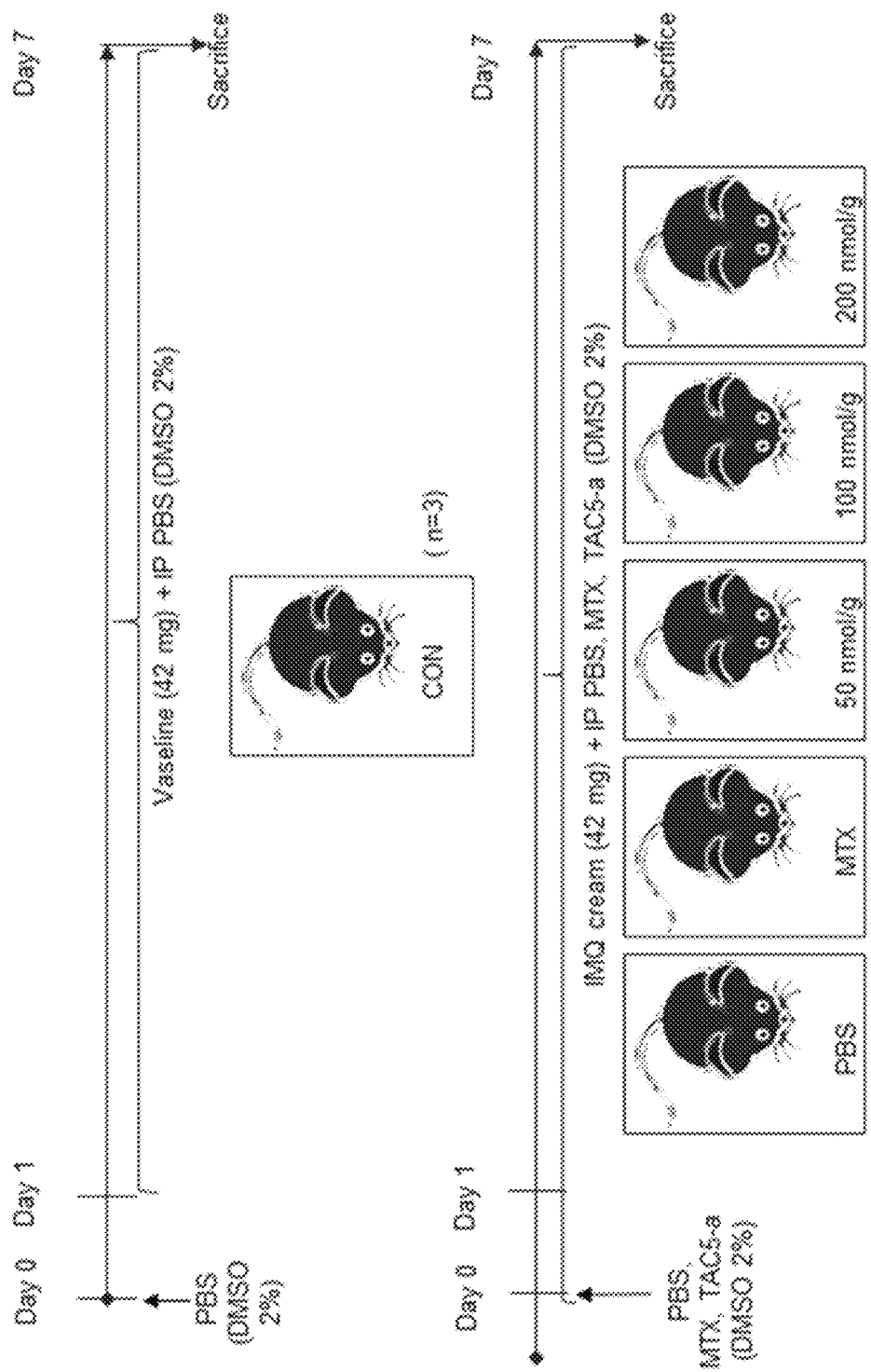
[FIG. 5A]

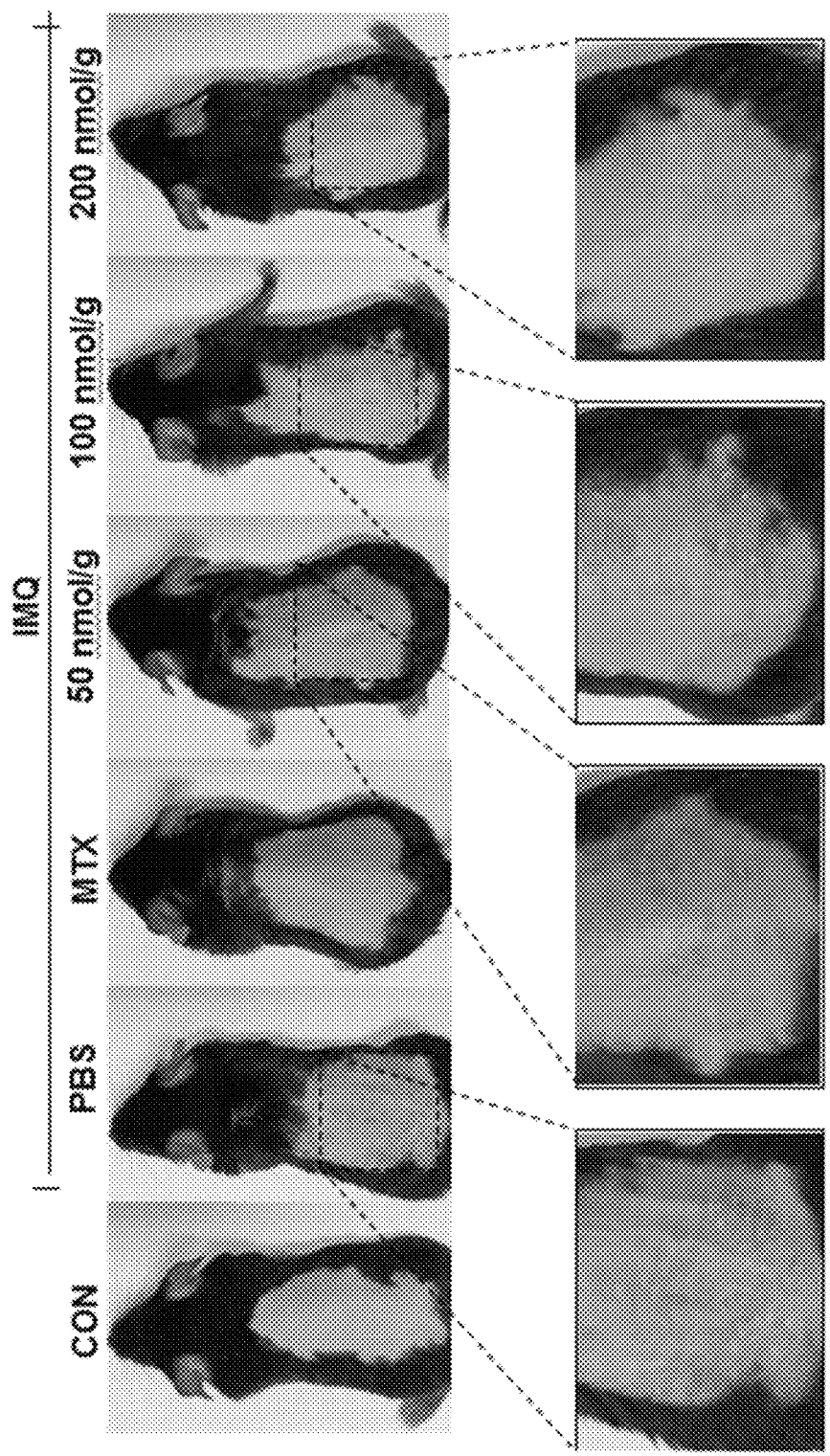
[FIG. 5B]

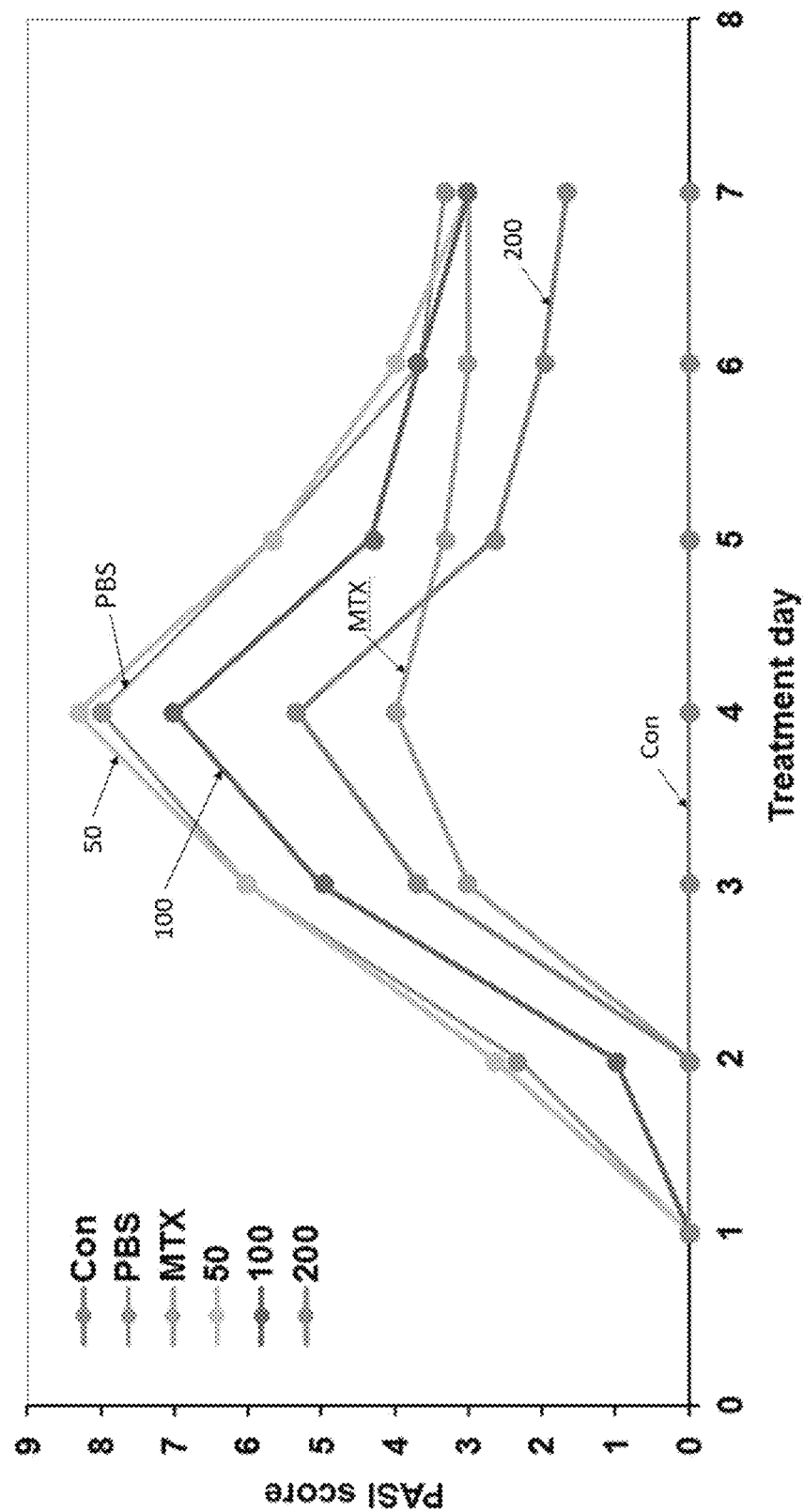
[FIG. 5C]

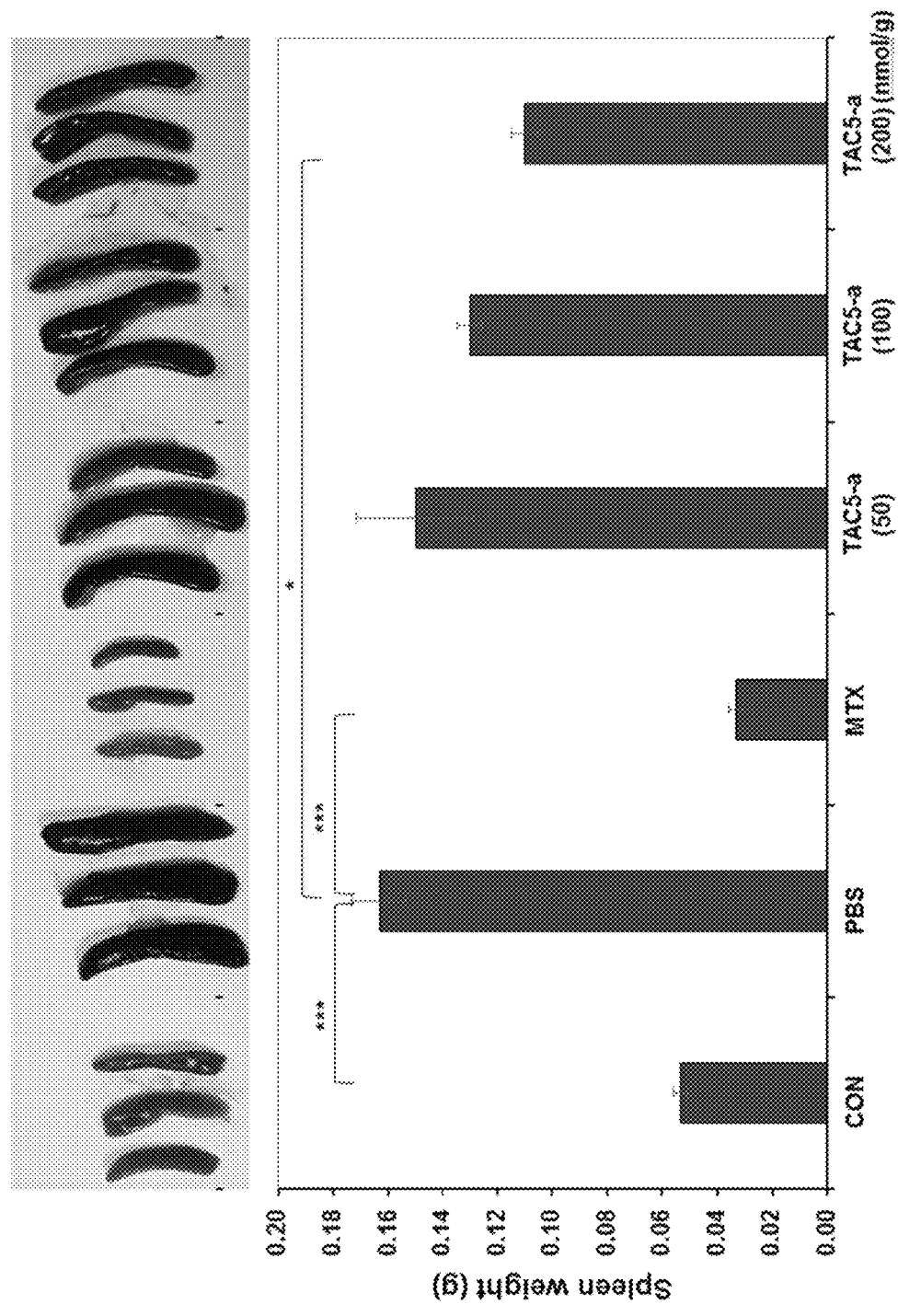
[FIG. 5D]

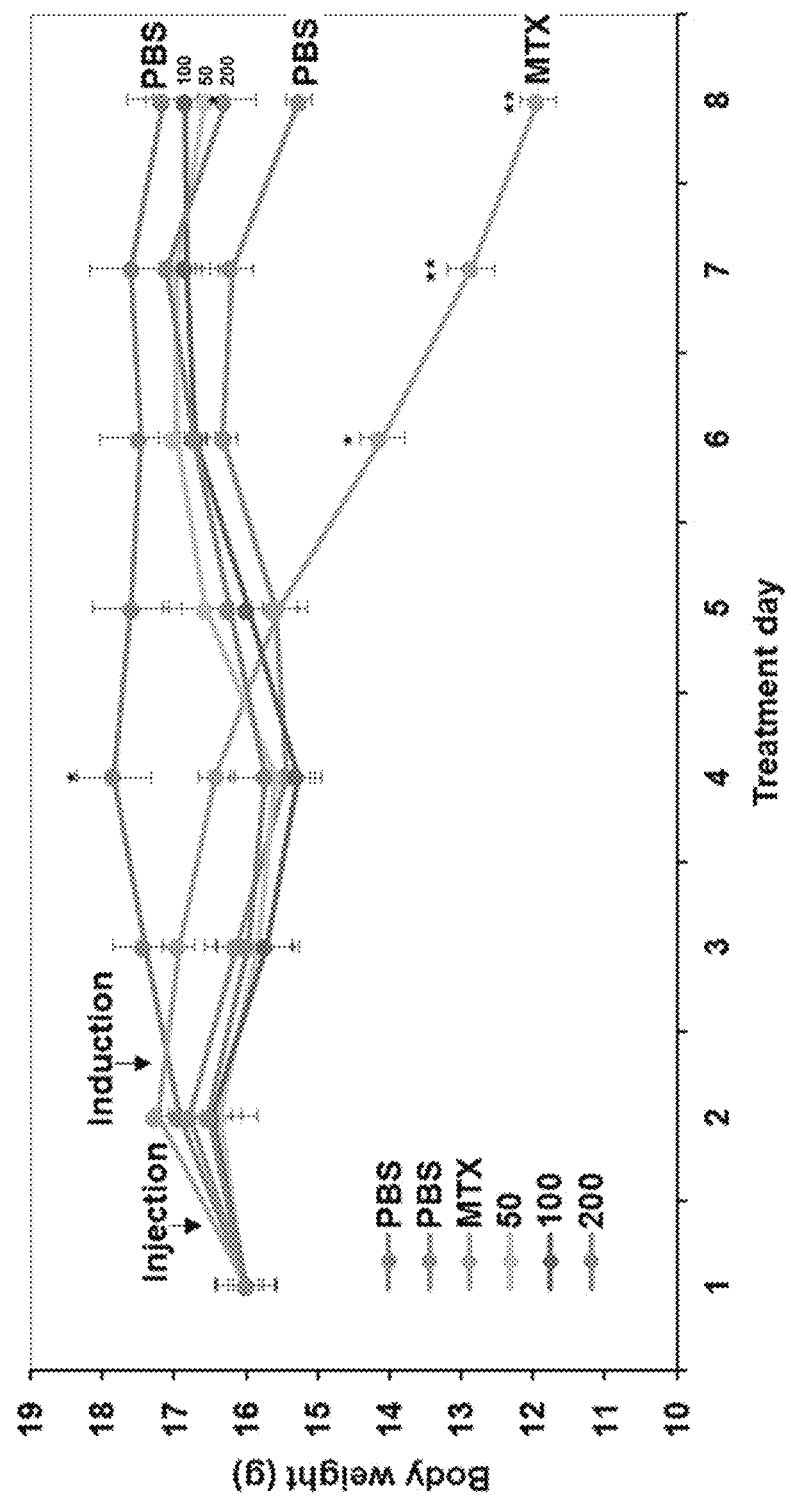
[FIG. 5E]

[FIG. 5F]
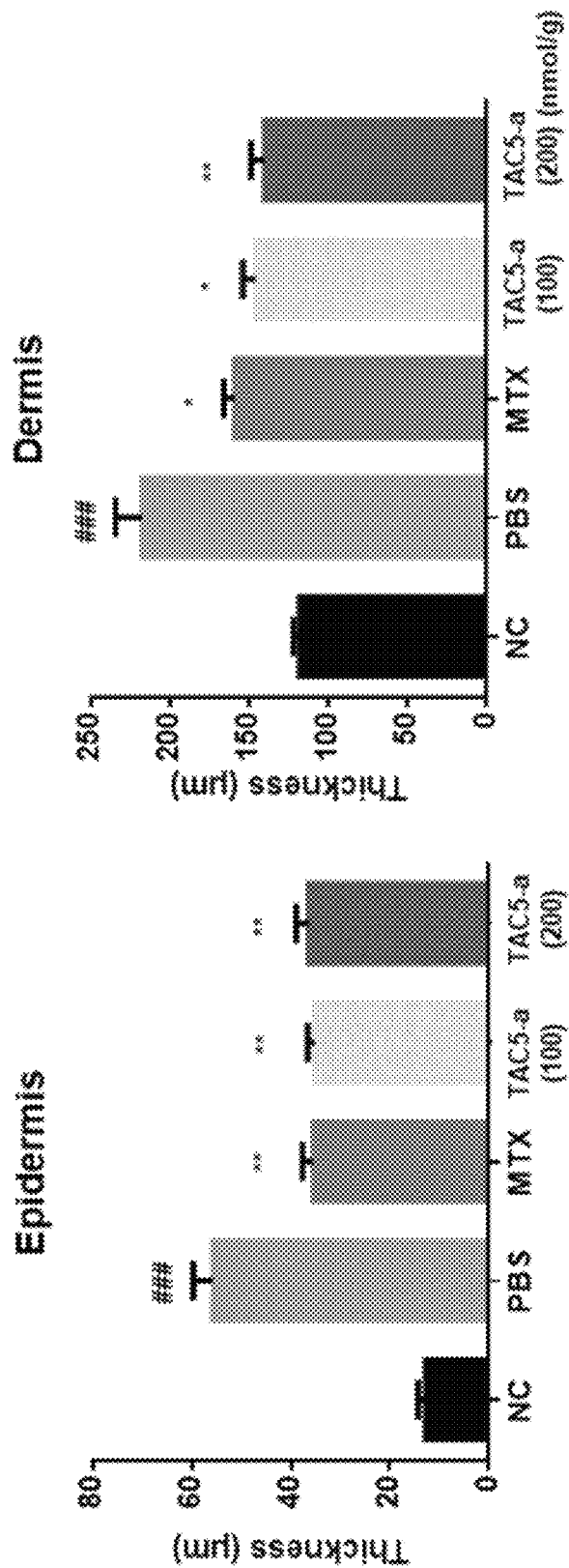

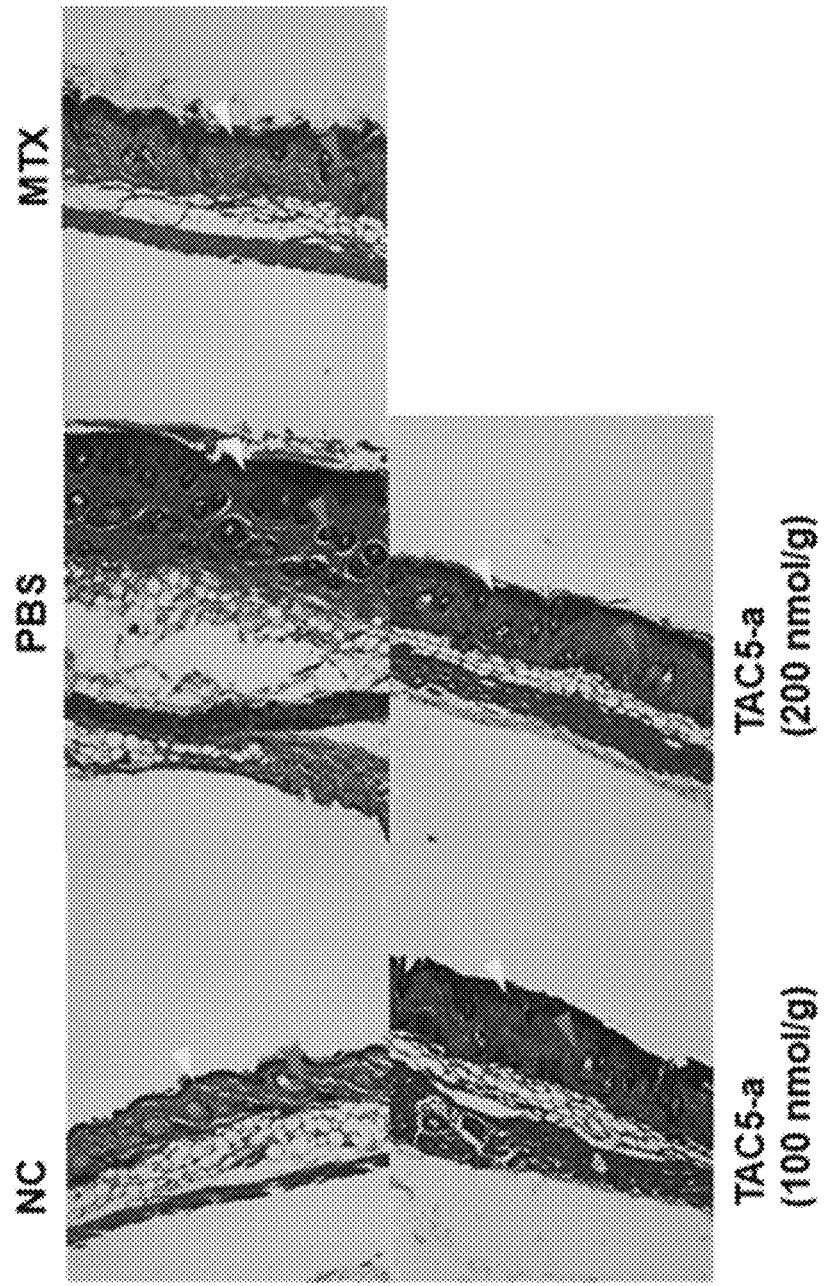
[FIG. 5G]

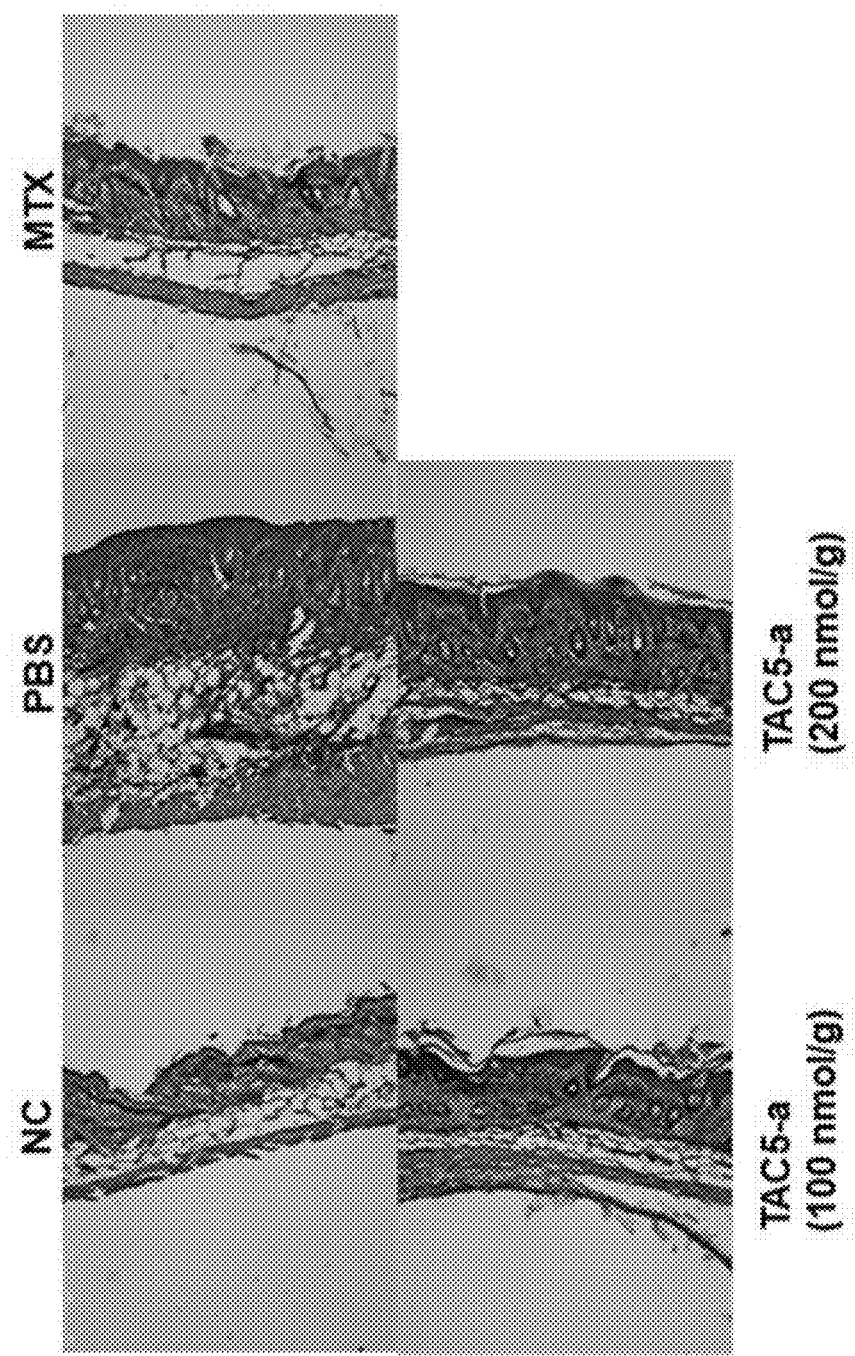
[FIG. 5H]

[FIG. 6A]
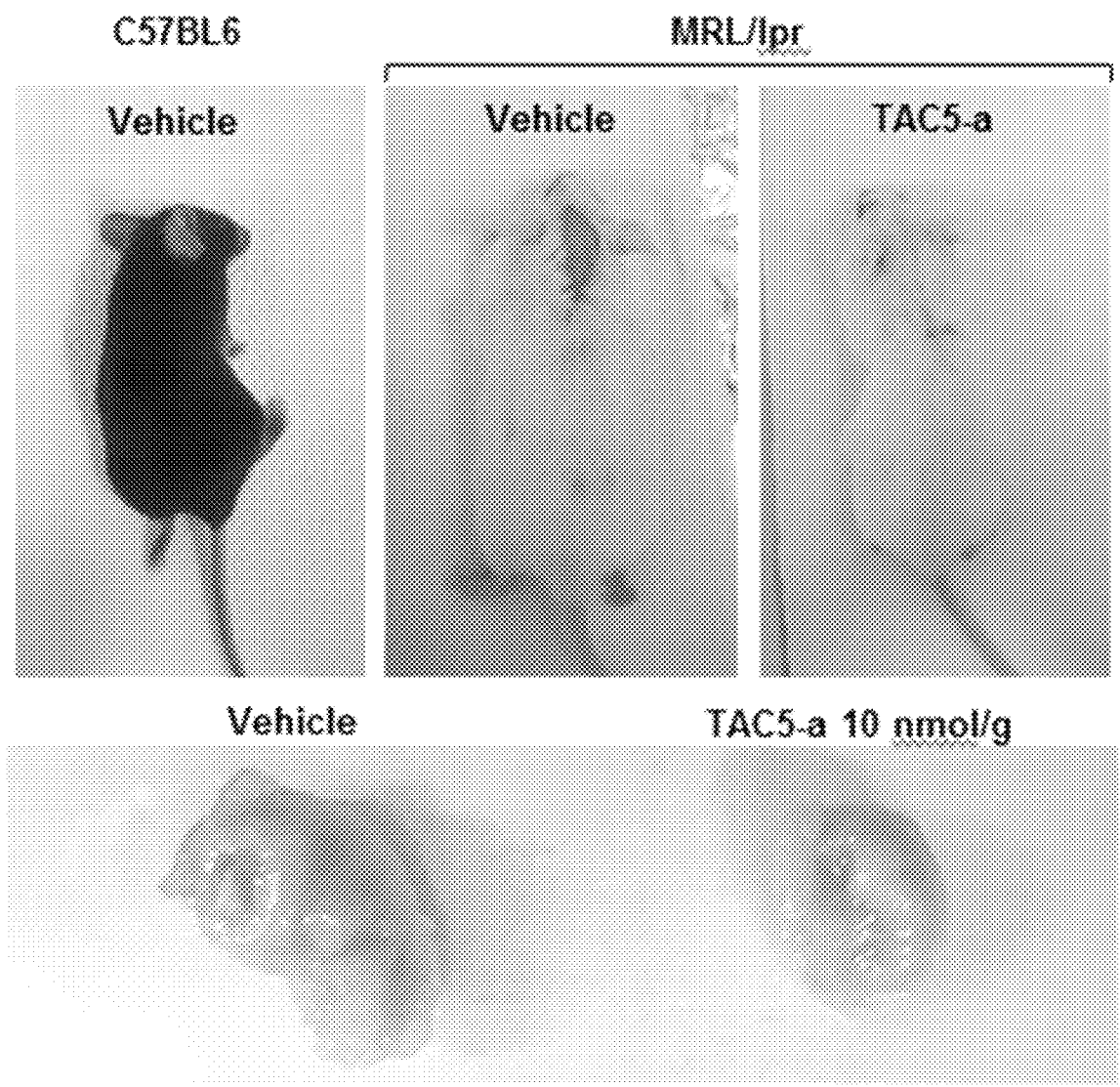

[FIG. 6B]
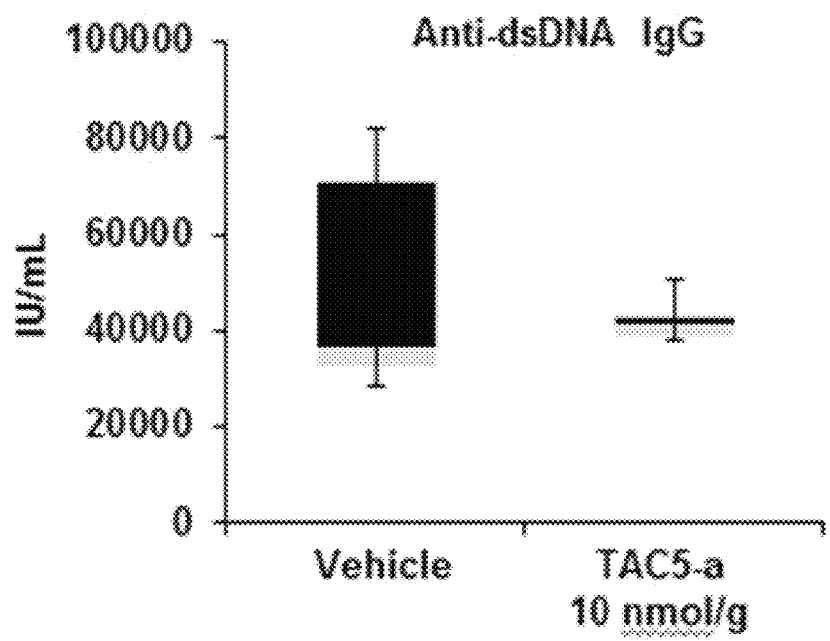
[FIG. 6C]
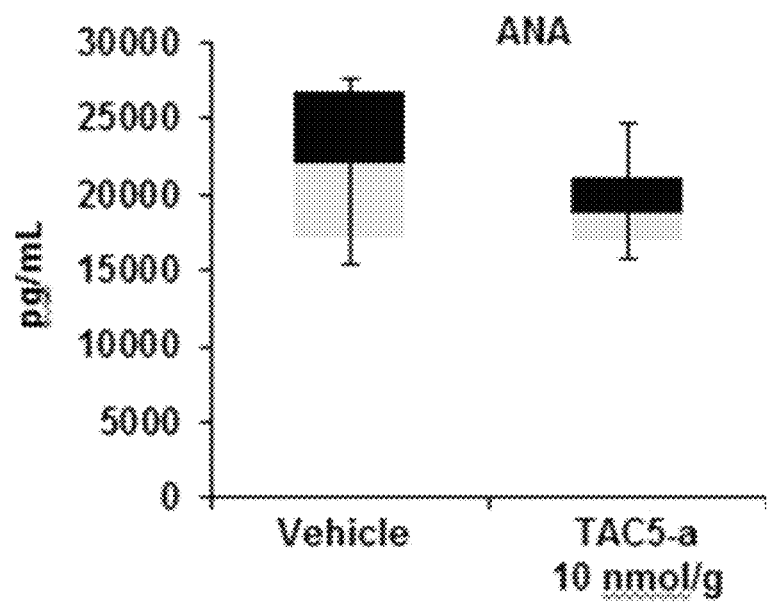

[FIG. 6D]
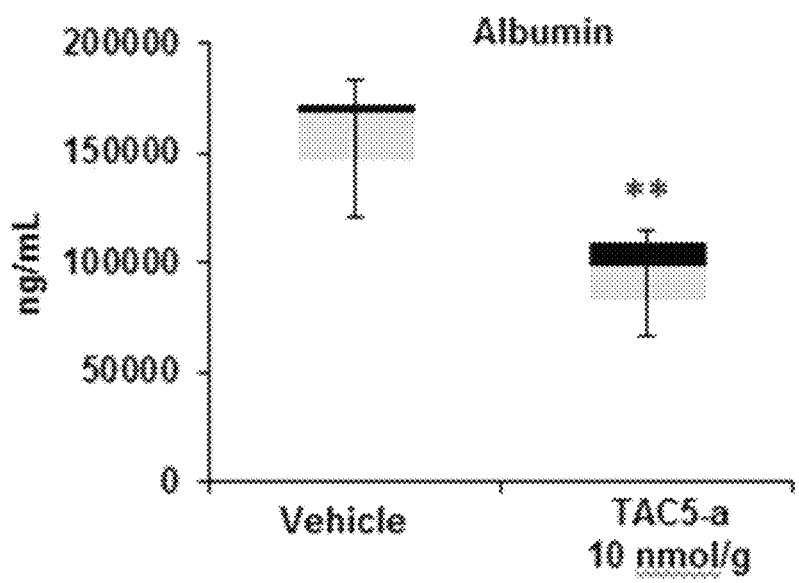
[FIG. 6E]
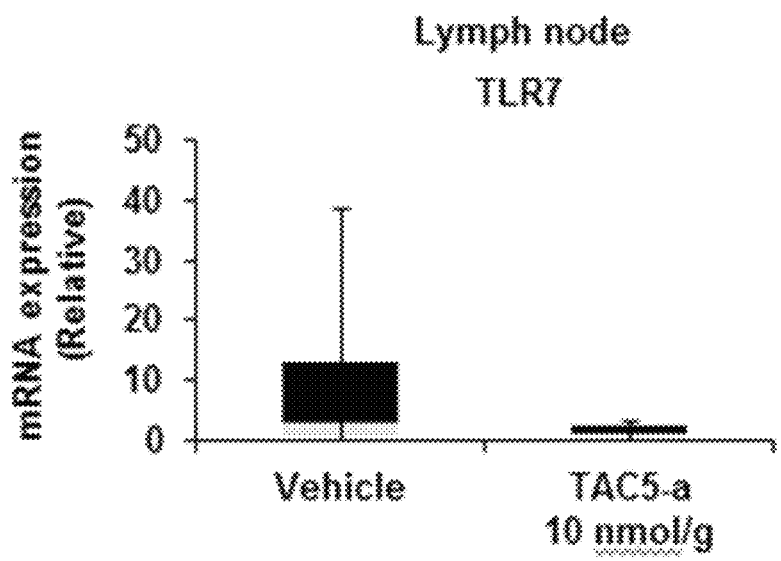

[FIG. 6F]
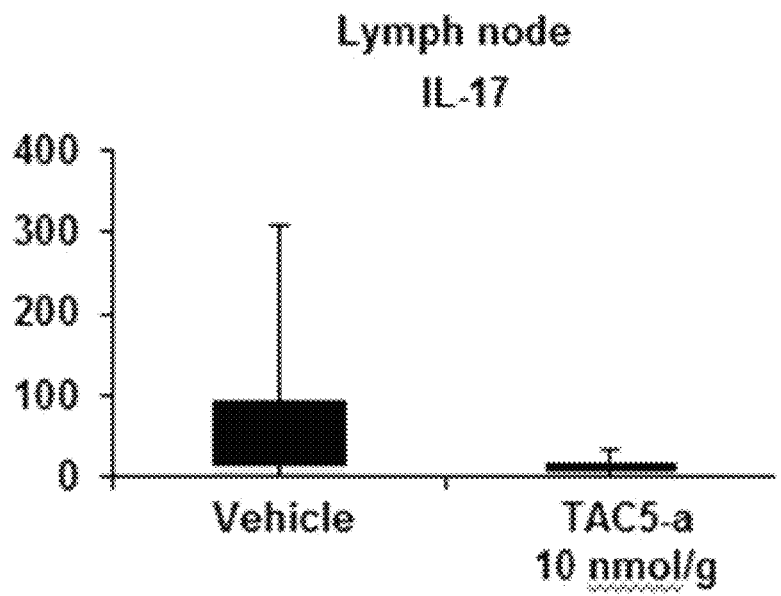
[FIG. 6G]
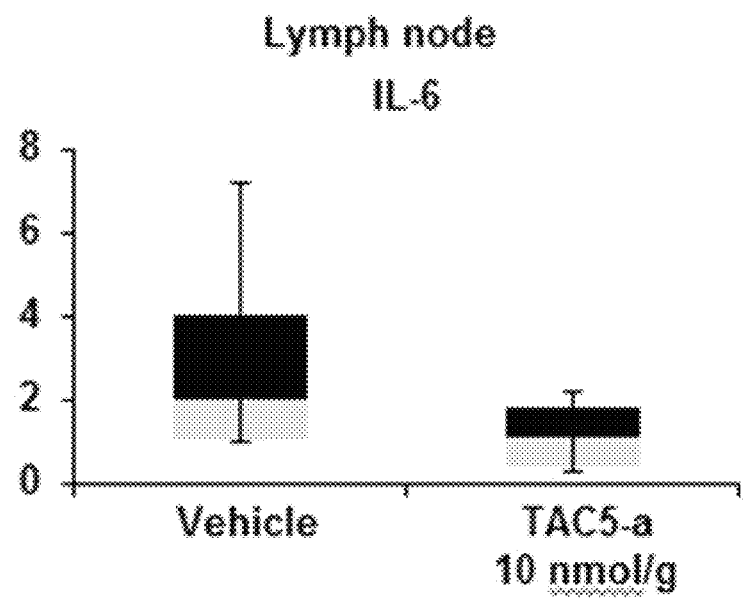

[FIG. 6H]
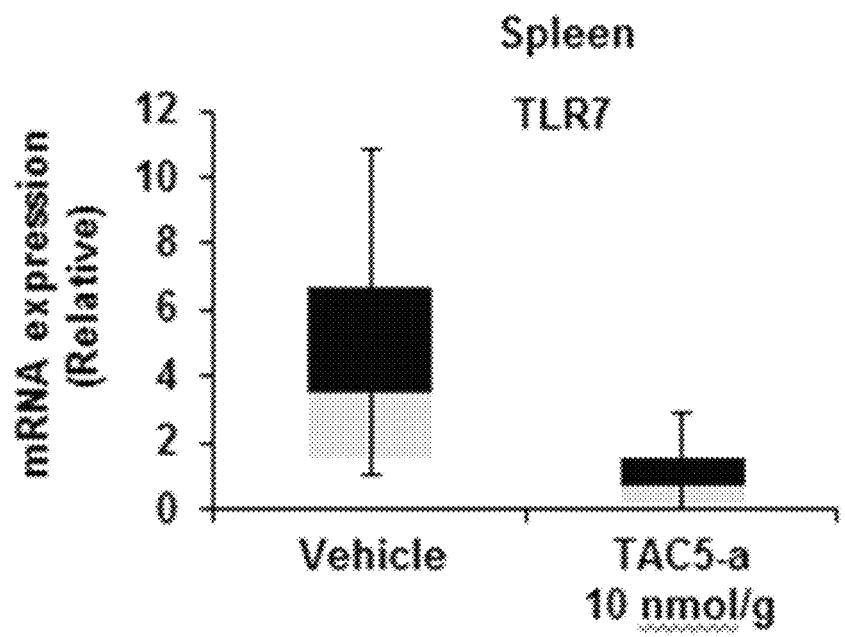
[FIG. 6I]
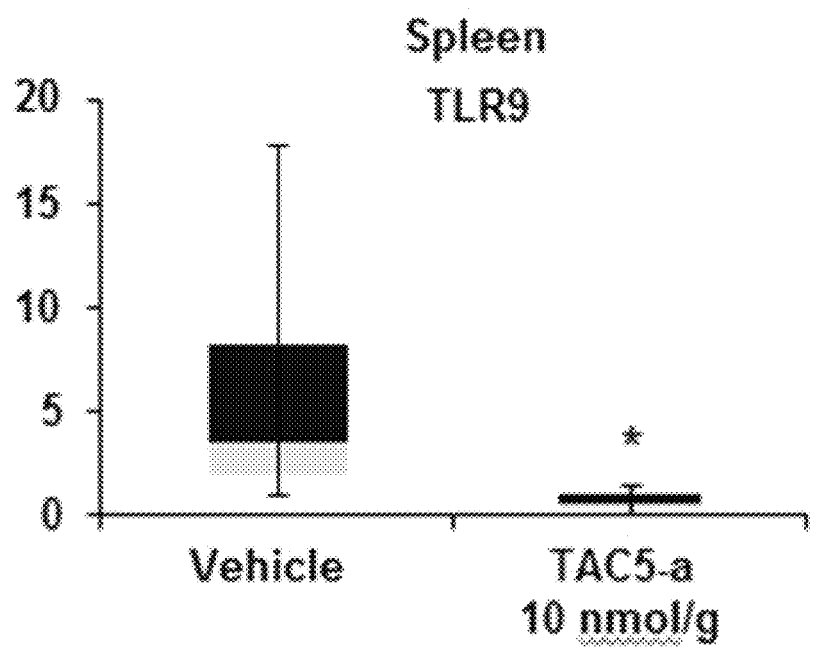

[FIG. 6J]
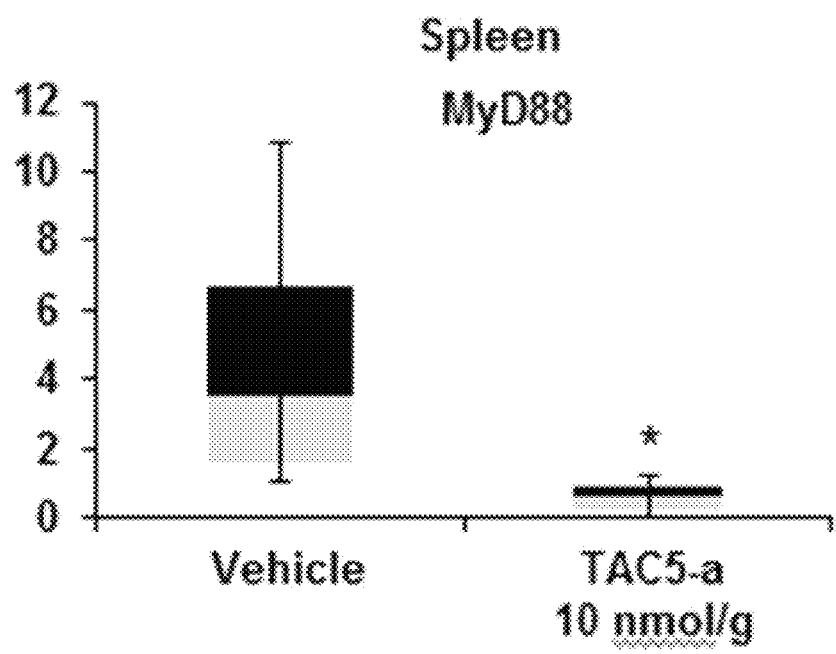

[FIG. 6K]
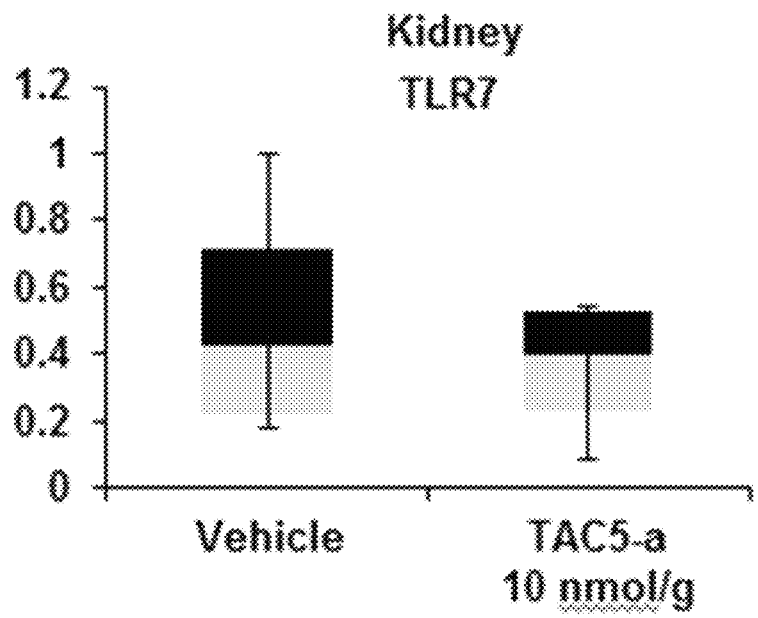
[FIG. 6L]
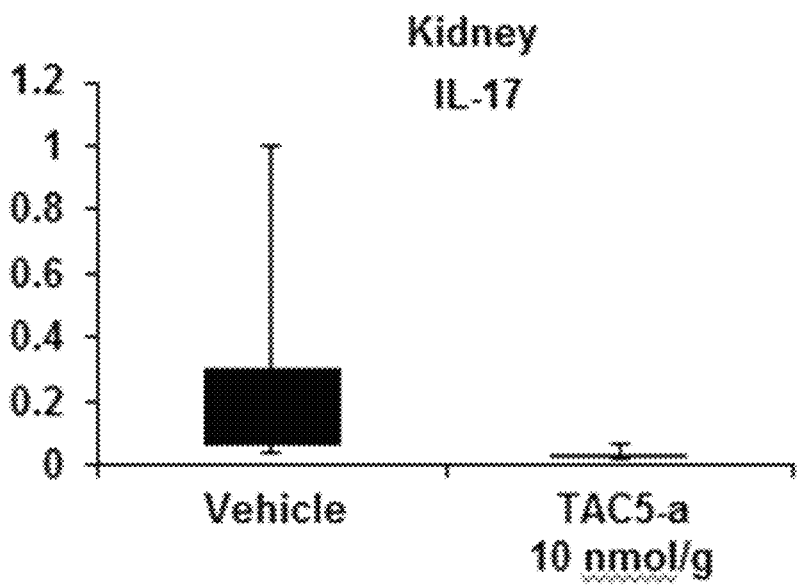

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: mTLR7 Forward Primer

<400> SEQUENCE: 1
atgtggacac ggaagagaca a                                              21

<210> SEQ ID NO 2
<211> LENGTH: 19
<212> TYPE: DNA
<213> ORGANISM: Artificial Sequence
<220> FEATURE:
<223> OTHER INFORMATION: mTLR7 Reverse Primer

<400> SEQUENCE: 2
ggtaagggta agattggtg                                                 19

<210> SEQ ID NO 3
<211> LENGTH: 21
<212> TYPE: DNA
<213> ORGANISM: Artificial Sequence
<220> FEATURE:
<223> OTHER INFORMATION: mTLR97 Forward Primer

<400> SEQUENCE: 3
atggttctcc gtcgaaggac t                                              21

<210> SEQ ID NO 4
<211> LENGTH: 19
<212> TYPE: DNA
<213> ORGANISM: Artificial Sequence
<220> FEATURE:
<223> OTHER INFORMATION: mTLR97 Reverse Primer

<400> SEQUENCE: 4
gaggcttcag ctcacaggg                                                 19

<210> SEQ ID NO 5
<211> LENGTH: 23
<212> TYPE: DNA
<213> ORGANISM: Artificial Sequence
<220> FEATURE:
<223> OTHER INFORMATION: mIL-6 Forward Primer

<400> SEQUENCE: 5
gaggatacca ctcccaacag acc                                            23

<210> SEQ ID NO 6
<211> LENGTH: 24
<212> TYPE: DNA
<213> ORGANISM: Artificial Sequence
<220> FEATURE:
<223> OTHER INFORMATION: mIL-6 Reverse Primer

<400> SEQUENCE: 6
aagtgcatca tcgttgttca taca                                           24

```
<210> SEQ ID NO 7
<211> LENGTH: 20
<212> TYPE: DNA
<213> ORGANISM: Artificial Sequence
<220> FEATURE:
<223> OTHER INFORMATION: mMyd88 Forward Primer

<400> SEQUENCE: 7
cacctgtgtc tggtccattg                                           20

<210> SEQ ID NO 8
<211> LENGTH: 20
<212> TYPE: DNA
<213> ORGANISM: Artificial Sequence
<220> FEATURE:
<223> OTHER INFORMATION: mMyd88 Reverse Primer

<400> SEQUENCE: 8
ctgttggaca cctggagaca                                           20

<210> SEQ ID NO 9
<211> LENGTH: 19
<212> TYPE: DNA
<213> ORGANISM: Artificial Sequence
<220> FEATURE:
<223> OTHER INFORMATION: mIL-17 Forward Primer

<400> SEQUENCE: 9
gctccagaag gccctcaga                                            19

<210> SEQ ID NO 10
<211> LENGTH: 19
<212> TYPE: DNA
<213> ORGANISM: Artificial Sequence
<220> FEATURE:
<223> OTHER INFORMATION: mIL-17 Reverse Primer

<400> SEQUENCE: 10
agctttccct ccgcattga                                            19

<210> SEQ ID NO 11
<211> LENGTH: 20
<212> TYPE: DNA
<213> ORGANISM: Artificial Sequence
<220> FEATURE:
<223> OTHER INFORMATION: mGAPDH Forward Primer

<400> SEQUENCE: 11
ctcaacacgg gaaacctcac                                           20

<210> SEQ ID NO 12
<211> LENGTH: 20
<212> TYPE: DNA
<213> ORGANISM: Artificial Sequence
<220> FEATURE:
<223> OTHER INFORMATION: mGAPDH Reverse Primer

<400> SEQUENCE: 12
cgctccacca actaagaacg                                           20
```

SMALL MOLECULE ANTAGONIST COMPOUND TAC5 SERIES HAVING TOLL-LIKE RECEPTOR 3/7/8/9 INHIBITORY FUNCTION

CROSS REFERENCE TO RELATED APPLICATIONS

This application is a National Stage of International Application No. PCT/KR2019/005978 filed May 20, 2019, claiming priority based on Korean Patent Application No. 10-2018-0058503 filed May 23, 2018 and Korean Patent Application No. 10-2018-0107638 filed Sep. 10, 2018.

SEQUENCE LISTING

The instant application contains a Sequence Listing which has been submitted electronically in ASCII format and is hereby incorporated by reference in its entirety. Said ASCII copy, created on Nov. 23, 2020, is named Q259455 Sequence Listing.txt and is 2,433 bytes in size.

TECHNICAL FIELD

The present invention relates to an antagonistic small-molecule compound having a function of inhibiting a toll-like receptor (TLR) 3/7/8/9, and more particularly to a novel small-molecule compound that inhibits a toll-like receptor 3/7/8/9 signaling pathway, a derivative thereof, a composition for preventing or treating an autoimmune disease or inflammatory disease containing the same, and a method for preventing or treating an autoimmune disease or inflammatory disease using the same.

BACKGROUND ART

Innate (or congenital) immunity is the first defense line against bacterial infection in the mammalian immune system, and pattern recognition receptors such as toll-like receptors (TLRs) are activated by recognizing pathogen-associated molecular patterns (PAMPs) or danger-associated molecular patterns (DAMPs). Examples include triacyl lipoprotein (e.g. Pam3CSK4) recognized by TLR1/2 (Takeuchi, O. et al., *J. Immunol.* 169: 10-14 (2002)), diacyl lipoprotein (e.g. Pam2CSK4) recognized by TLR2/6 (Takeuchi, O. et al., *Int. Immunol.* 13: 933-940 (2001)), lipopolysaccharide (LPS) recognized by TLR4 (Poltorak, A. et al., *Science* 282: 2085-2088 (1998)), bacterial flagellin recognized by TLR5 (Poltorak, A. et al. *Science* 282: 2085-2088 (1998), viral double-stranded RNA (dsRNA) recognized by TLR3 (Poltorak, A. et al. al., *Science* 282: 2085-2088 (1998)), viral single-stranded RNA (ssRNA) recognized by TLR7 and TLR8 (Diebold, S. S. et al., *Science* 303: 1529-1531 (2004); Heil, F. et al. al., Science 303: 1526-1529 (2004)), unmethylated CpG-containing oligodeoxynucleotides (ODN) recognized by TLR9 (Hemmi, H. et al. *Nature* 408: 740-745 (2000)) and the like.

TLRs play a key role in the innate immune response (Akira, S. & Takeda, K. Nat. Rev. Immunol. 4, 499-511), and are classified into extracellular TLRs acting on the plasma membrane, including TLR1, TLR2, TLR4, TLR5, TLR6 and TLR11, and intracellular TLRs acting in cells such as endosomes, including TLR3, TLR7, TLR8, and TLR9. Structurally, TLRs have a leucine-rich repeat (LRR) site recognized by a ligand or accessory molecule at the N-terminus of the extracellular domain, and have a toll/interleukin 1 receptor (TIR) domain that delivers a signal to the C-terminus of the intracellular part.

In particular, TLR7, TLR8, TLR9, and TLR3 sense exogenous single-stranded RNA (ssRNA), double-stranded RNA (dsRNA) and CpG DNA, which are exposed to endosomes from extracellular intruders, or recognize, as ligands, endogenous ssRNA or DNA fragments exposed from tissue damaged by necrosis or apoptosis in tissue due to an abnormal response, to thereby amplify inflammatory cytokines through signaling processes. In general, TLR7 and TLR8 recognize ssRNA from influenza or damaged cells, while TLR9 senses CpG DNA fragments generated from the genome of bacteria and viruses or damaged tissue, and TLR3 recognizes dsRNA, which is an intermediate product of viral proliferation, to thereby activate the innate immune response. Research associated with the use of TLR as a target for treatment of immune-associated diseases is being actively conducted worldwide due to the known roles of TLR.

MyD88 (myeloid differentiation primary response 88)-dependent signaling of TLR7/8/9 forms a dimer with the corresponding ligand, and the TIR domain of TLR combines with the TIR domain of MyD88 to form a complex and thereby activate a signaling pathway (Hemmi, H. et al., Nat. Immunol. 3, 196-200, (2002)). The activated TLR signal induces activation of NF-κB, migration to the nucleus, and activation of MAPK, and expresses interferon α (IFNα) and IFN-inducible genes. The activation of NF-κB and MAPK secretes inflammatory cytokines such as TNFα, IL1β (interleukin 1β) and IL-6. The MyD88-independent signaling process of TLR3 is initiated by the binding between the TIR domain of TLR3 and the TIR domain of TRIF (TIR domain-containing adapter-inducing interferon-β), and type 1 interferon is secreted by the activation of the interferon regulatory factor (IRF). In addition, TLR activity produces oxidative stressors such as NO and ROS in macrophages.

The TLRs (TLRs 3, 7, 8 and 9) in the endosome membrane play an important role in protecting hosts from various viral and bacterial infections. In particular, the expression of TLRs 7, 8 and 9 is essential for sustained defense against pathogenic components or self-antigens released from damaged or stressed tissue/cells (Demaria, O. et al., *J. Clin. Invest.* 120: 3651-3662 (2010)). Malfunctions of these nucleic-acid-sensing TLRs have been associated with several autoimmune pathologies such as psoriasis and systemic lupus erythematosus (SLE) (Vincent, F B et al., *Nat. Rev. Rheumatol.* 10: 365-373 (2014)). However, the etiology of these diseases remains unclear (Krieg, A. M. & Vollmer, J., *Immunol. Rev.* 220: 251-269 (2007); Terhorst, D. et al., *J. Immunol.* 195: 4953-4961 (2015)). Thus, there is increasing need for the development of novel antagonists that inhibit the progression of endosomal TLR-mediated diseases.

As described above, TLR may serve as a target for treatment of various diseases such as autoimmune diseases, inflammatory diseases and cancer, and thus research has been actively conducted on substances targeting TLR and medical compositions for treating TLR-associated diseases.

Accordingly, as a result of intensive research efforts to develop substances targeting TLR and medical compositions for treating TLR-associated diseases, the present inventors found that a novel compound containing TAC5 (TLR antagonistic compound 5) or a derivative thereof, TAC5-a or TAC5-c, inhibits the TLR-signaling pathway induced by TLR7, TLR8, TLR9 or TLR3 activation, thereby inhibiting the secretion of cytokines (IL6, TNFα, IFNβ), NO and ROS, and overactivation of NF-κB and MAPK, treating skin erythema and lupus nephritis in the lupus mouse model

[MRL/Fas$^{lpr/lpr}$] and reducing inflammatory cytokines to thereby alleviate inflammatory response. Based on this finding, the present invention was completed.

SUMMARY

It is one object of the present invention to provide an antagonistic small-molecule compound having a function of inhibiting a toll-like receptor (TLR) 3/7/8/9 and TLR7, TLR8, TLR9 and TLR3 inhibitors containing the same.

It is another object of the present invention to provide a composition for preventing or treating an autoimmune disease containing the compound as an active ingredient.

It is another object of the present invention to provide a composition for preventing or treating an inflammatory disease containing the compound as an active ingredient.

It is another object of the present invention to provide a method for preventing or treating an autoimmune disease or inflammatory disease including administering the composition for preventing or treating an autoimmune disease or inflammatory disease containing the compound as an active ingredient to a subject in need of prevention or treatment thereof.

In accordance with one aspect of the present invention, the above and other objects can be accomplished by the provision of a compound represented by the following Formula (1) or a pharmaceutically acceptable salt thereof:

[Formula 1]

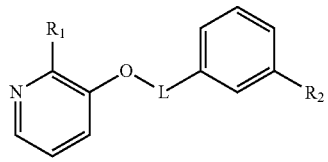

wherein L is a single bond, substituted or unsubstituted linear or branched alkylene, cycloalkylene, haloalkylene, arylene, heteroalkylene, heteroarylene, arylene alkylene, alkylene arylene, alkylene heteroarylene, heteroarylene alkylene, alkylene ester or alkylene amide, wherein the alkylene is $C_{2-30}$, the cycloalkylene is $C_{3-30}$, the arylene is $C_{6-30}$, and the heteroalkylene or the heteroarylene contains a heteroatom selected from fluorine, oxygen, sulfur and nitrogen, and $R_1$ and $R_2$ are the same as or different from each other, and are each independently a hydrogen atom, $C_{1-6}$ straight- or branched-chain alkyl, amino, —NR$_3$R$_4$ (wherein R$_3$ and R$_4$ are the same as or different from each other and are independently substituted with a hydrogen atom, alkyl, cycloalkyl or aryl), hydroxy, halogen, a nitrile group, a nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide or acryl, wherein the alkyl or the alkoxy is $C_{1-30}$, the cycloalkyl is $C_{3-30}$, the allyl is $C_{2-30}$, the aryl is $C_{6-30}$, and heteroaryl and heterocycloalkyl contain a heteroatom selected from fluorine, oxygen, sulfur and nitrogen.

In accordance with another aspect of the present invention, provided is a method of preparing a compound represented by Formula 1-1 including the following steps:
(a) reacting a solution of 2-amino-3-hydroxypyridine and cesium carbonate with 3-nitrobenzyl bromide to produce 3-((3-nitrobenzyl)oxy)-pyridin-2-amine, and (b) reacting the 3-((3-nitrobenzyl)oxy)-pyridin-2-amine with SnCl$_2$ to produce 3-((3-aminobenzyl)oxy)pyridin-2-amine.

[Formula 1-1]

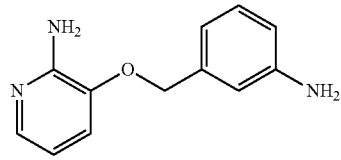

In accordance with another aspect of the present invention, provided is a method of preparing a compound represented by Formula 1-3 including reacting a solution of 2-amino-3-benzyloxypyridine, copper (I) iodide, potassium carbonate, and N,N'-dimethylethylenediamine with bromobenzene to synthesize 3-(benzyloxy)-N-phenylpyridin-2-amine.

[Formula 1-3]

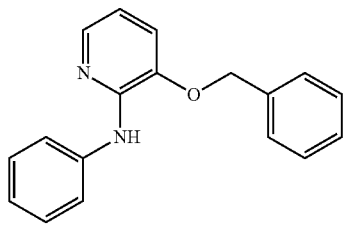

In accordance with another aspect of the present invention, provided is a pharmaceutical composition for preventing or treating an autoimmune disease or an inflammatory disease containing the compound or a pharmaceutically acceptable salt thereof as an active ingredient.

In accordance with another aspect of the present invention, provided is a method for preventing or treating an autoimmune disease or inflammatory disease including administering the composition for preventing or treating an autoimmune disease or an inflammatory disease containing the compound as an active ingredient to a subject in need of prevention or treatment thereof.

In accordance with another aspect of the present invention, provided is the use of the composition for preventing or treating an autoimmune disease or inflammatory disease containing the compound as an active ingredient for the prevention or treatment of the autoimmune disease or inflammatory disease.

DESCRIPTION OF DRAWINGS

FIG. 1 is a flowchart relating to screening of a QSAR model according to the present invention.

FIGS. 2A-2D show the result of analysis of cell viability of TAC5 and the tumor necrosis factor α (TNF-α) inhibitor profile according to an embodiment of the present invention.

FIGS. 3A-3E show the effects of TAC5 on NF-κB and MAPK activity according to an embodiment of the present invention.

FIGS. 4A-4G show the inhibitory effects of TAC5-a, TAC5-c, TAC5-d and TAC5-e on the TLR-signaling pathway according to an embodiment of the present invention.

FIGS. 5A-5H show the defense effect of TAC5-a in a psoriasis mouse model according to an embodiment of the present invention.

FIGS. 6A-6L show the defense effect of TAC5-a in a systemic lupus erythematosus mouse model according to an embodiment of the present invention.

DISCLOSURE

Figure 7A:
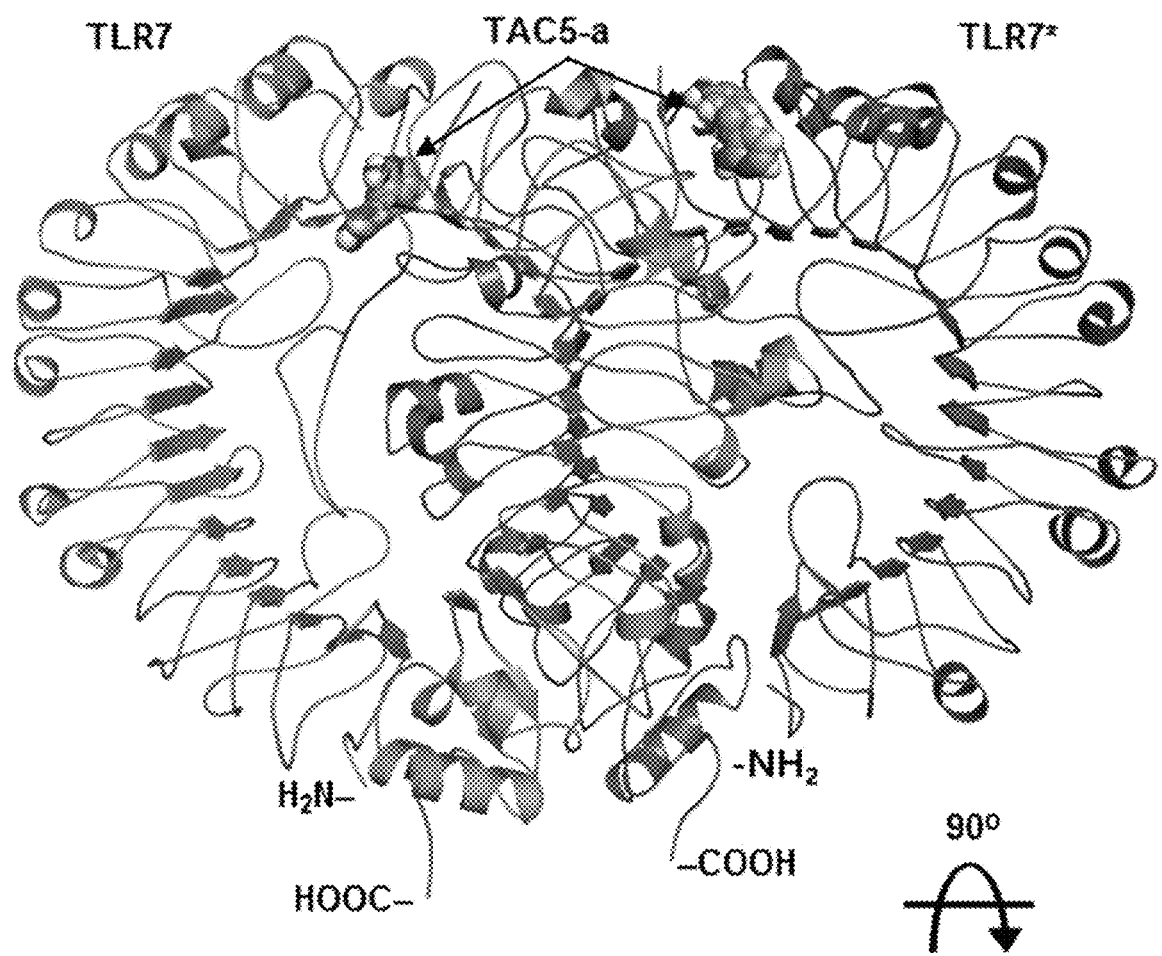
FIGS. 7A-7F show a construction model of TAC5-a binding to TLR7 and TLR8 according to an embodiment of the present invention.
Figure 7B:
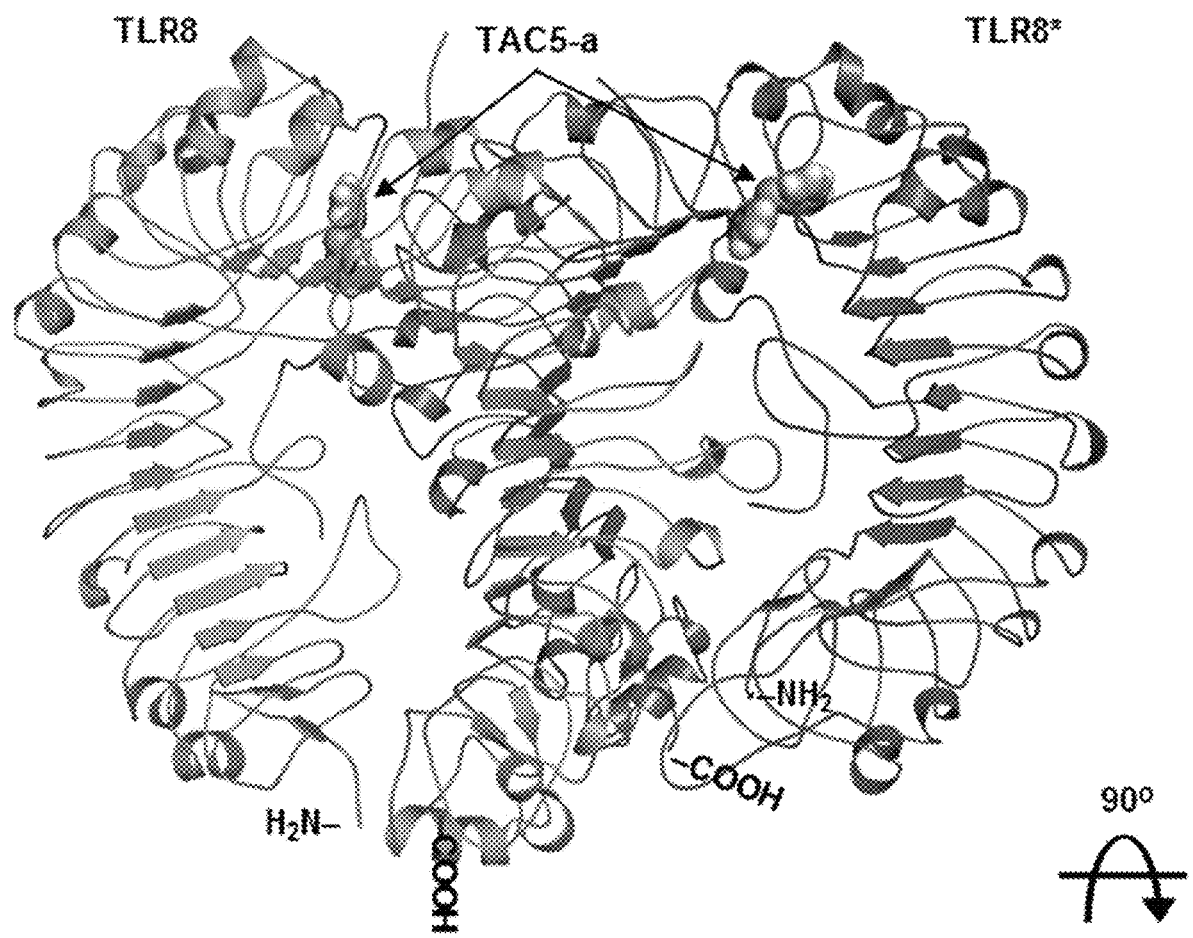
Figure 7C:
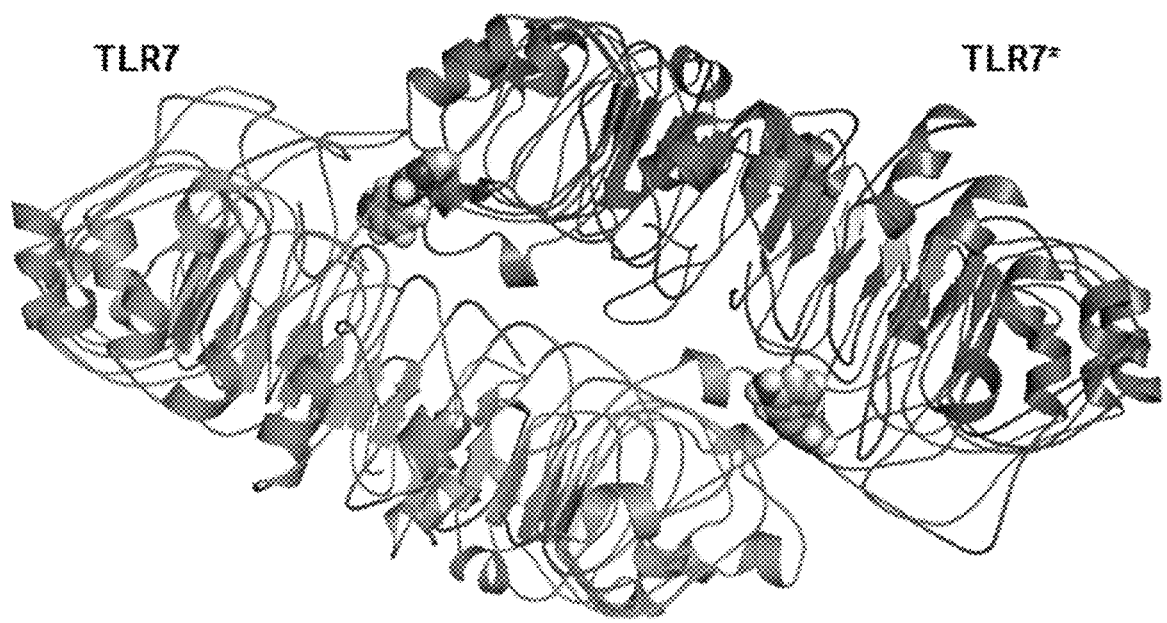
Figure 7D:
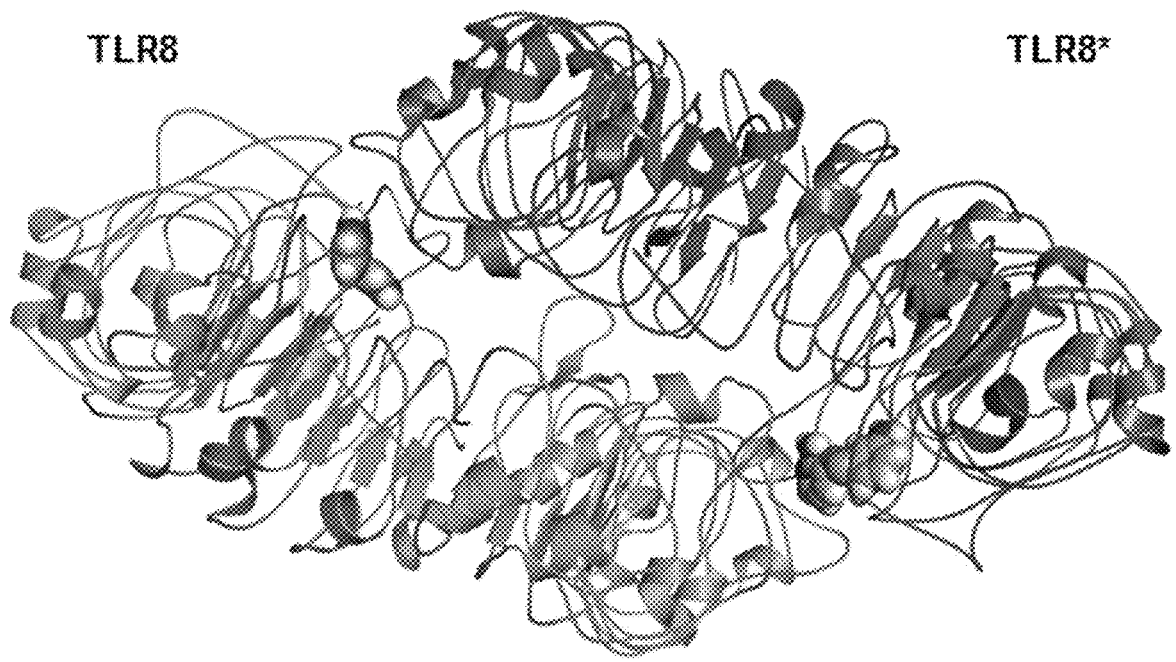

Unless defined otherwise, all technical and scientific terms used herein have the same meanings as appreciated by those skilled in the field to which the present invention pertains. In general, the nomenclature used herein is well-known in the art and is ordinarily used.

The present invention is based on the finding that a novel compound containing TAC5 (TLR antagonistic compound 5) or a derivative thereof, TAC5-a or TAC5-c, inhibits the TLR-signaling pathway induced by TLR7, TLR8, TLR9 or TLR3 activation, thereby inhibiting the secretion of cytokines (IL6, TNFα, IFNβ), NO and ROS, and overactivation of NF-κB and MAPK, treating skin erythema and lupus nephritis in the lupus mouse model [MRL/Fas$^{lpr/lpr}$] and reducing inflammatory cytokines to thereby alleviate inflammatory responses, and on identification that the compound has therapeutic effects in the psoriasis mouse model.

In one aspect, the present invention is directed to a compound represented by the following Formula (1) or a pharmaceutically acceptable salt thereof:

[Formula 1]

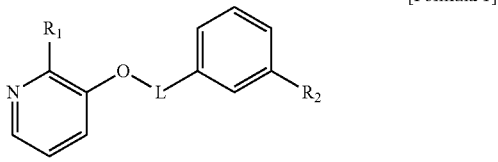

wherein L is a single bond, substituted or unsubstituted linear or branched alkylene, cycloalkylene, haloalkylene, arylene, heteroalkylene, heteroarylene, arylene alkylene, alkylene arylene, alkylene heteroarylene, heteroarylene alkylene, alkylene ester or alkylene amide, wherein the alkylene is $C_{2-30}$, the cycloalkylene is $C_{3-30}$, the arylene is $C_{6-30}$, and the heteroalkylene or the heteroarylene contains a heteroatom selected from fluorine, oxygen, sulfur and nitrogen, wherein the substituent is $C_{1-30}$ alkyl, $C_{3-30}$ cycloalkyl, $C_{1-30}$ alkyl ester, $C_{1-30}$ alkylamide, —CH$_2$OCH$_2$CH$_3$ and —CH$_2$OCH$_2$CH$_2$NR$_5$R$_6$ (wherein R$_5$ and R$_6$ are the same as or different from each other and are independently selected from a hydrogen atom, $C_{1-30}$ alkyl, $C_{3-30}$ cycloalkyl, and $C_{6-30}$ aryl), but is not limited thereto, R$_1$ and R$_2$ are the same as or different from each other, and are each independently a hydrogen atom, straight- or branched-chain alkyl, amino, —NR$_3$R$_4$ (wherein R$_3$ and R$_4$ are the same as or different from each other and are independently substituted with a hydrogen atom, alkyl, cycloalkyl or aryl), hydroxy, halogen, a nitrile group, a nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide or acryl, wherein the alkyl or the alkoxy is $C_{1-30}$, the cycloalkyl is $C_{3-30}$, the allyl is $C_{2-30}$, the aryl is $C_{6-30}$, and the heteroaryl and heterocycloalkyl contain a heteroatom selected from fluorine, oxygen, sulfur and nitrogen.

In another aspect, the present invention is directed to a method of preparing a compound represented by Formula 1-1 including (a) reacting a solution of 2-amino-3-hydroxypyridine and cesium carbonate with 3-nitrobenzyl bromide to produce 3-((3-nitrobenzyl)oxy)-pyridin-2-amine, and (b) reacting the 3-((3-nitrobenzyl)oxy)-pyridin-2-amine with SnCl$_2$ to produce 3-((3-aminobenzyl)oxy)pyridin-2-amine.

[Formula 1-1]

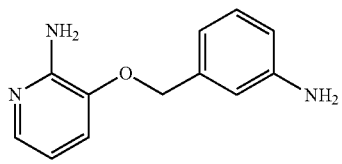

In accordance with another aspect of the present invention, provided is a method of preparing a compound represented by Formula 1-3 including reacting a solution of 2-amino-3-benzyloxypyridine, copper (I) iodide, potassium carbonate, and N,N'-dimethylethylenediamine with bromobenzene to synthesize 3-(benzyloxy)-N-phenylpyridin-2-amine.

[Formula 1-3]

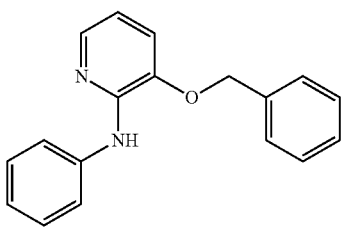

In accordance with another aspect of the present invention, provided is a pharmaceutical composition for preventing or treating an autoimmune disease or an inflammatory disease containing the compound or a pharmaceutically acceptable salt thereof as an active ingredient.

Hereinafter, the present invention will be described in detail.

The present invention provides a small-molecule compound, TAC5 (TLR antagonistic compound 5), which inhibits the TLR7-, TLR8-, TLR9- and TLR3-signaling pathways, and novel derivatives thereof, TAC5-a and TAC5-c, a method of preparing the compound, and a composition containing the compound for preventing or treating an autoimmune disease or inflammatory disease including systemic lupus erythematosus, psoriasis, skin rash, photosensitivity, arthritis, oral ulcers, nephritis, hemocytopenia, vasculitis and serositis. That is, the present invention provides a small-molecule compound that prevents secretion of TNFα (tumor necrosis factor α) induced by IMQ (TLR7 agonist), CL075 (TLR7/8 agonist), R848 (TLR7/8 agonist), TL8 (TLR8 agonist), CpG ODN (TLR9 agonist), or poly(I:C) (TLR3 agonist), NF-κB (nuclear factor kappa-light-chain-enhancer of activated B cell) activity, and phosphorylation of MAPKs (mitogen-activated protein kinases: p38, c-Jun N-terminal kinase, and extracellular signal-regulated kinase), and additionally suppresses the production of inflammatory cytokines including IL-6 (interleukin 6), and a composition containing the compound for preventing or treating an autoimmune disease or inflammatory disease including systemic lupus erythematosus, psoriasis, skin rash, photosensitivity, arthritis, oral ulcers, nephritis, hemocytopenia, vasculitis and serositis.

The present invention provides a compound represented by the following Formula (1) (TAC5) or a pharmaceutically acceptable salt thereof:

[Formula 1]

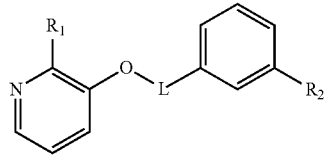

wherein L is a single bond, substituted or unsubstituted linear or branched alkylene, cycloalkylene, haloalkylene, arylene, heteroalkylene, heteroarylene, arylene alkylene, alkylene arylene, alkylene heteroarylene, heteroarylene alkylene, alkylene ester or alkylene amide, wherein the alkylene is $C_{2-30}$, the cycloalkylene is $C_{3-30}$, the arylene is $C_{6-30}$, and the heteroalkylene or heteroarylene is a divalent radical containing a heteroatom selected from fluorine, oxygen, sulfur and nitrogen, and $R_1$ and $R_2$ are the same as or different from each other, and are each independently a hydrogen atom, straight- or branched-chain alkyl, amino, —$NR_3R_4$ (wherein $R_3$ and $R_4$ are the same as or different from each other and are independently substituted with a hydrogen atom, alkyl, cycloalkyl or aryl), hydroxy, halogen, a nitrile group, a nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide or acryl, wherein the alkyl or the alkoxy is $C_{1-30}$, the cycloalkyl is $C_{3-30}$, the allyl is $C_{2-30}$, the aryl is $C_{6-30}$, and the heteroaryl and heterocycloalkyl contain a heteroatom selected from fluorine, oxygen, sulfur and nitrogen.

In the present invention, it is preferable that L, $R_1$ and $R_2$ have combinations of substituents as shown in Table 1 below.

TABLE 1

| L | $R_1$ | $R_2$ |
|---|---|---|
| Alkylene | —$NR_3R_4$ (wherein $R_3$ and $R_4$ are the same as or different from each other, and are independently a hydrogen atom, alkyl, cycloalkyl or aryl) | —$NR_3R_4$ (wherein $R_3$ and $R_4$ are the same as or different from each other, and are independently a hydrogen atom, alkyl, cycloalkyl or aryl) Alkylaryl Hydrogen |
| Heteroarylene | | Hydrogen |
| Alkylene amide | —$NR_3R_4$ (wherein $R_3$ and $R_4$ are the same as or different from each other, and are independently a hydrogen atom, alkyl, cycloalkyl or aryl) | Hydrogen |

In addition, the compound of the present invention is preferably any one selected from Formula 1-1 (TAC5-a), Formula 1-2 (TAC5-b), Formula 1-3 (TAC5-c), Formula 1-4 (TAC5-d), Formula 1-5 (TAC5-e), Formula 1-6 (TAC5-f), Formula 1-7 (TAC5-g), Formula 1-8 (TAC5-h), and Formula 1-9 (TAC5-e-1), particularly preferably Formula 1-1 (TAC5-a) and Formula 1-3 (TAC5-c), but it is not limited thereto.

[Formula 1-1]

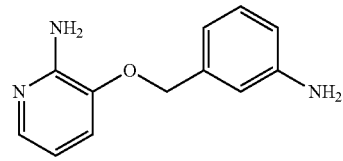

[Formula 1-2]

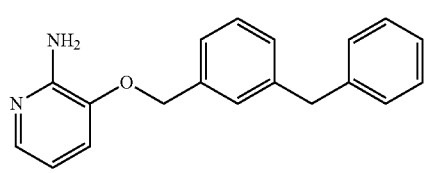

[Formula 1-3]

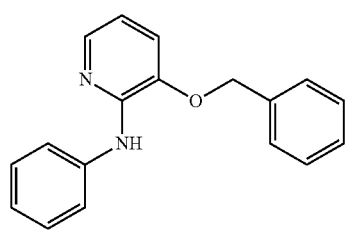

[Formula 1-4]

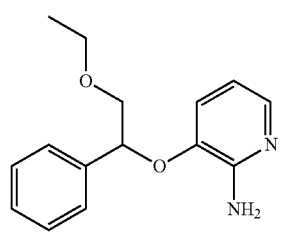

[Formula 1-5]

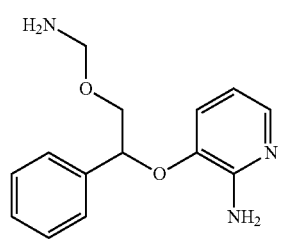

[Formula 1-6]

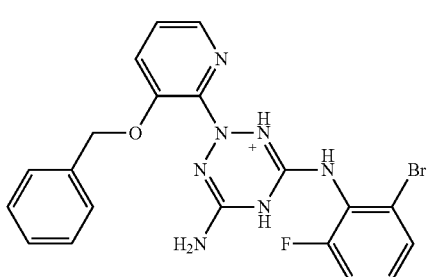

[Formula 1-7]

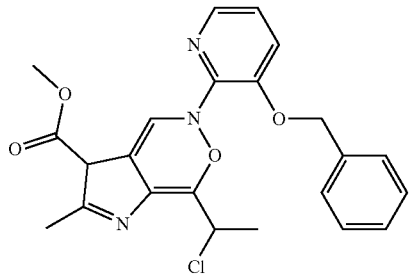

[Formula 1-8]

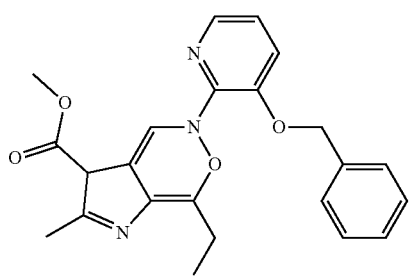

[Formula 1-9]

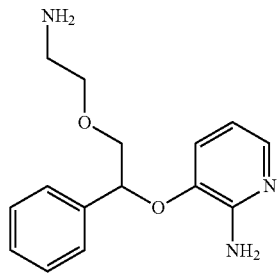

In the present invention, TAC5 and the derivative thereof, TAC5-a, TAC5-c, TAC5-d or TAC5-e, may be prepared according to a chemical synthesis method known in the art, and may be synthesized as described below in detail.

In an embodiment of the present invention, provided is a method of preparing a compound represented by Formula 1-1 including (a) reacting a solution of 2-amino-3-hydroxypyridine and cesium carbonate with 3-nitrobenzyl bromide to produce 3-((3-nitrobenzyl)oxy)-pyridin-2-amine, and (b) reacting the 3-((3-nitrobenzyl)oxy)-pyridin-2-amine with SnCl₂ to produce 3-((3-aminobenzyl)oxy)pyridin-2-amine.

[Formula 1-1]

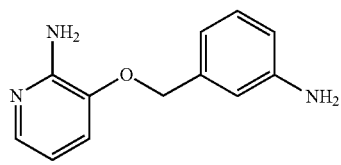

In another embodiment of the present invention, provided is a method of preparing a compound represented by Formula 1-3 including reacting a solution of 2-amino-3-benzyloxypyridine, copper (I) iodide, potassium carbonate and N,N'-dimethylethylenediamine with bromobenzene to synthesize 3-(benzyloxy)-N-phenylpyridin-2-amine.

[Formula 1-3]

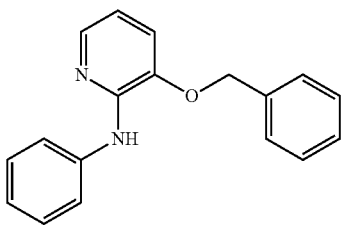

The present invention provides a pharmaceutical composition for preventing or treating an autoimmune disease or an inflammatory disease containing the compound or a pharmaceutically acceptable salt thereof as an active ingredient.

In the present invention, the autoimmune disease or inflammatory disease is selected from the group consisting of psoriasis, systemic lupus erythematosus (SLE), skin rash, photosensitivity, arthritis, oral ulcer, nephritis, hemocytopenia, vasculitis, serositis, inflammatory bowel disease (IBD), diabetes, multiple sclerosis, skin sclerosis, pemphigus, atopic dermatitis, urethritis, cystitis, arteriosclerosis, allergic disease, rhinitis, asthma, acute pain, chronic pain, periodontitis, gingivitis, gout, myocardial infarction, congestive heart failure, high blood pressure, angina pectoris, gastric ulcer, cerebral infarction, Down's syndrome, multiple sclerosis, obesity, dementia, depression, schizophrenia, tuberculosis, sleep disorders, sepsis, burns, pancreatitis, Parkinson's disease, and stroke.

In addition, the pharmaceutical composition for preventing or treating an autoimmune disease or inflammatory disease according to the present invention may further include a pharmaceutically acceptable carrier, excipient or diluent.

The terms used to define the compound according to the present invention have the following meanings.

As used herein, the term "$C_{1-30}$ alkyl" refers to a monovalent linear or branched saturated hydrocarbon moiety that has 1 to 30 carbon atoms and contains only carbon and hydrogen atoms. Examples of the alkyl group include, but are not limited to, methyl, ethyl, propyl, isopropyl, butyl, isobutyl, sec-butyl, tert-butyl, and the like. Examples of the "branched alkyl" include isopropyl, isobutyl, tert-butyl and the like.

As used herein, the term "$C_{1-30}$ alkoxy" refers to the formula —O—$C_{1-30}$ alkyl and includes, but is not limited to, methoxy, ethoxy, isopropoxy, tert-butoxy and the like.

Specific examples of the term "halo" include fluorine (F), chlorine (Cl), bromine (Br) and iodine (I).

As used herein, the term "$C_{6-30}$ aryl" refers to a compound including at least one ring having a shared pi electron system, for example, a monocyclic or fused-ring polycyclic (i.e., rings sharing adjacent pairs of carbon atoms) group. That is, in the present specification, the aryl may include phenyl, naphthyl and biaryl, unless otherwise defined. In one embodiment of the present invention, the aryl refers to an aromatic ring having 6 to 30 carbon atoms.

As used herein, the term "$C_{3-30}$ cyclic alkyl" refers to a cyclic saturated hydrocarbon moiety that has 5 to 6 carbon atoms and contains only carbon and hydrogen atoms. Examples of the cyclic alkyl group include, but are not limited to, cyclopentyl, cyclohexyl and the like.

As used herein, the term "heteroaryl" refers to an aromatic ring having 5 or 6 ring atoms containing 1 to 4 heteroatoms selected from the group consisting of N, O and S, or a bicyclic ring having a heteroaryl ring fused to a benzene ring or another heteroaryl ring, unless otherwise defined. Examples of a monocyclic heteroaryl include, but are not limited to, thiazolyl, oxazolyl, thiophenyl, furanyl, pyrrolyl, imidazolyl, isoxazolyl, isothiazolyl, pyrazolyl, triazolyl, triazinyl, thiadiazolyl, tetrazolyl, oxadiazolyl, pyridinyl, pyridazinyl, pyrimidinyl, pyrazinyl, and groups similar thereto. Examples of the bicyclic heteroaryl include, but are not limited thereto, indolyl, azaindolyl, indolinyl, benzothiophenyl, benzofuranyl, benzimidazolyl, benzooxazolyl, benzisoxazolyl, benzothiazolyl, benzothiadiazolyl, benzotriazolyl, quinolinyl, isoquinolinyl, purinyl, furopyridinyl and groups similar thereto.

As used herein, the term "heterocycloalkyl" refers to a saturated or partially unsaturated carbocyclic ring having 5 to 9 ring atoms containing 1 to 3 heteroatoms selected from N, O and S, in addition to carbon atoms. For example, the heterocycloalkyl may be azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, dihydroindolyl, dihydrofuryl, dihydroimidazolinyl, dihydrooxazolyl, tetrahydropyridinyl, dihydropyranyl, dihydrobenzofuranyl, benzodioxolyl, or benzodioxanyl.

As used herein, the term "TLR7" refers to a protein categorized as a toll-like receptor (TLR), which is a family of transmembrane proteins that function as monitors for pathogen infection, which is a protein encoded by a TLR7 gene and is also called UNQ248/PRO285. The TLR7 recognizes ssRNA (single-stranded RNA) of an RNA virus or synthetic small molecules, imidazoquinoline, loxoribine and bropirimine to activate the innate immune system.

As used herein, the term "TLR8" refers to a protein categorized as a toll-like receptor (TLR), which is a family of transmembrane proteins that function as monitors for pathogen infection, which is a protein encoded by a TLR8 gene and is also called CD288 (cluster of differentiation 288) or UNQ249/PRO286. The TLR8 is activated by single-stranded viral RNA, phagocytized bacterial RNA or the synthetic small molecule TL8.

As used herein, the term "TLR9" refers to a protein categorized as a toll-like receptor (TLR), which is a family of transmembrane proteins that function as monitors for pathogen infection, which is a protein encoded by a TLR9 gene and is also called CD289 or UNQ5798/PRO19605. The TLR9 recognizes unmethylated CpG oligodeoxynucleotide DNA fragments from bacteria or DNA viruses to activate the innate immune system.

As used herein, the term "TLR3" refers to a protein categorized as a toll-like receptor (TLR), which is a family of transmembrane proteins that function as monitors for pathogen infection, which is a protein encoded by a TLR3 gene and is also called CD283 or IIAE2. TLR3 is very important for the activation of the innate immune system because it recognizes the double-stranded RNA (dsRNA) and poly I:C of the virus.

As used herein, the term "TLR-signaling pathway" refers to a signaling pathway through TLR, which may be a reaction that depends on a complex formed by TLR and the adapter protein MyD88 (for TLR7/8/9) or a complex formed by TLR and the adapter protein TRIF (for TLR3) and functions to transmit a signal. Activated TLR7/8/9 activates NF-κB through a Myd88-dependent signaling process, moves to the nucleus, and induces activation of MAPK. The activation of NF-κB and MAPK causes inflammatory cytokines such as TNFα, IL1β and IL6 to be secreted and oxidative stressors such as nitrogen monoxide (hereinafter referred to as NO) and reactive oxygen species (hereinafter referred to as ROS) to be produced in macrophages. In addition, TLR3 activates TRIF, interferon-regulator (IRF) and NF-κB, thus inducing MyD88-independent signaling process and secretion of type 1 interferon.

As used herein, the term "TIR domain" is a domain for intracellular signaling, has three highly conserved regions, and mediates the interaction between TLR and other signaling molecules. In an activated reaction, the TIR domain induces binding with MyD88 or TRIF and activates the TLR-signaling pathway.

As used herein, the term "inhibition" refers to a phenomenon in which biological activity or signaling activity is deteriorated due to deficiency, disharmony or many other causes, and may include partial or complete blocking, reduction or prevention of activity of TLR, delaying of activation, inactivation, or down-regulation.

Accordingly, the present invention provides the use of small-molecule compounds represented by TAC5, TAC5-a or TAC5-c for inhibition of TLR7-, TLR8-, TLR9- or TLR3-signaling pathways, and downstream signal molecules thereof, for example, BAFF (B-cell-activating factor of the TNF family; B-lymphocyte stimulator; BLyS).

According to an embodiment of the present invention, the compound represented by TAC5 and the derivative thereof, TAC5-a or TAC5-c, has excellent effects of inhibiting the TLR-signaling pathway induced by TLR7, TLR8, TLR9 or TLR3 activation, thereby inhibiting the secretion of the cytokines (IL6, TNFα, IFNβ), NO and ROS, and overactivation of NF-κB and MAPK, treating skin erythema and lupus nephritis in the lupus mouse model [MRL/Faslpr/lpr] and reducing inflammatory cytokines (mitigating inflammatory reactions). Thus, the compound can be used as a composition for preventing or treating autoimmune diseases and inflammatory diseases caused by activation of TLR7, TLR8, TLR9 or TLR3.

In addition, the present invention provides a TLR7, TLR8, TLR9 and/or TLR3 inhibitor containing the compound.

As used herein, the term "inhibitor" refers to a molecule that partially or completely inhibits influences on other molecules such as receptors or intracellular mediators by any mechanism.

As used herein, the term "TLR7, TLR8, TLR9 and/or TLR3 inhibitor" refers to a substance that is capable of directly or indirectly, or substantially interfering with, reducing or inhibiting the biological activity of TLR7, TLR8, TLR9 and/or TLR3, preferably a substance that is capable of reducing the secretion of NF-κB, MAPK, inflammatory cytokines, NO and ROS by binding to TLR7, TLR8, TLR9 and/or TLR3 receptors, neutralizing the activity thereof, and thereby blocking TLR7-, TLR8-, TLR9- and/or TLR3-signaling pathways.

Thus, the present invention provides a composition for preventing or treating an autoimmune disease containing the compound as an active ingredient.

As used herein, the term "autoimmune disease" refers to a disease caused by a process in which a problem occurs in inducing or maintaining self-tolerance, leading to an immune response to a self-antigen and thus an attack on the organism's own tissue. The term "self-tolerance" refers to immunologic unresponsiveness meaning the lack of harmful response to an antigenic substance constituting the self. An autoimmune disease includes a disease resulting from the breakdown of self-resistance in which an adaptive immune system responds to a self-antigen and mediates cellular and tissue damage. In certain embodiments, the autoimmune disease at least partially results from a humoral immune response.

The autoimmune diseases of the present invention include systemic lupus erythematosus, insulin-dependent diabetes mellitus, multiple sclerosis, autoimmune encephalomyelitis, rheumatoid arthritis, autoimmune arthritis, myasthenia gravis, thyroiditis, experimental uveitis, Hashimoto's thyroiditis, primary myxedema, thyroid toxicosis, pernicious anemia, autoimmune atrophy gastritis, Addison's disease, early menopause, male infertility, childhood diabetes, Goodpasture syndrome, common pemphigus, pemphigus, sympathetic ophthalmitis, lens uveitis, autoimmune hemolytic anemia, idiopathic leukocytosis, primary biliary cirrhosis, chronic active hepatitis Hbs-ve, latent cirrhosis, ulcerative colitis, Sjogren's syndrome, scleroderma, Wegener's granulomatosis, polymyositis/dermatomyositis, and discoid LE, but are not limited thereto.

In addition, non-limiting examples of the autoimmune disease include acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, antibody-mediated transplant rejection, anti-GBM/anti-TBM nephritis, antiphospholipid antibody syndrome (APS), autoimmune angioedema, autoimmune aplastic anemia, autoimmune autonomic dystrophy, autoimmune hepatitis, autoimmune hyperlipidemia, autoimmune immunodeficiency syndrome, autoimmune inner-ear disease (AIED), autoimmune myocarditis, autoimmune pancreatitis, autoimmune diabetic retinopathy, autoimmune thrombocytopenia purpura (ATP), autoimmune thyroid disease, autoimmune urticaria, axon and neuronal neuropathy, Balo disease, Bechet's disease, pemphigus, cardiomyopathy, Castleman's disease, celiac disease, Chagas disease, chronic fatigue syndrome, chronic inflammatory demyelinating polyneuropathy (CIDP), chronic recurrent multifocal osteomyelitis (CRMO), Churg-Strauss syndrome, scarring pemphigus/benign mucosal pemphigus, Crohn's disease, Cogan syndrome, cold agglutinin disease, congenital heart blockage, coxsackie myocarditis, CREST disease, essential mixed cryoglobulinemia, demyelinating neuropathies, herpetic dermatitis, dermatitis, Devic's disease (optic neuromyelitis), discoid lupus, Dressler's syndrome, endometriosis, eosinophilic fasciitis, nodular erythema, experimental allergic encephalomyelitis, Evans syndrome, fibromyalgia, fibrous alveolitis, giant-cell arteritis (temporal arteritis), glomerulonephritis, Goodpasture syndrome, granulomatosis with polyangiitis (GPA), Graves' disease, Guillain-Barre syndrome, Hashimoto's encephalitis, Hashimoto thyroiditis, hemolytic anemia, Henoch-Schoenlein purpura, gestational herpes, hypogammaglobulinemia, hypergammaglobulinemia, idiopathic thrombocytopenia purpura (ITP), IgA kidney disease, IgG4-related sclerotic disease, immunomodulatory lipoprotein, inclusion body myositis, inflammatory bowel disease, insulin-dependent diabetes (type 1), interstitial cystitis, juvenile arthritis, juvenile diabetes, Kawasaki syndrome, Eaton-Lambert syndrome, leukopenia vasculitis, lichen planus, lichen sclerosis, ligneous conjunctivitis, linear IgA disease (LAD), lupus (SLE), Lyme disease, Meniere's disease, microscopic polyangiitis, mixed connective tissue disease (MCTD), monoclonal gammopathy of undetermined significance (MGUS), encroaching corneal ulcer, Mucha-Habermann disease, multiple sclerosis, myasthenia gravis, myositis, narcolepsy, neuromyelitis (Devic's disease), neutropenia, ocular cicatricial pemphigoid, optic neuritis, recurrent rheumatism, PANDAS (pediatric autoimmune neuropsychiatric disorders associated with streptococcal infections), antitumor cerebellar degeneration, paroxysmal nocturnal hemoglobinuria (PNH), facial unilateral atrophy, Parsonage-Turner syndrome, pars planitis (peripheral uveitis), pemphigus, peripheral neuropathy, perivenous encephalomyelitis, pernicious anemia, POEMS syndrome, polyarteritis nodosa, type I, type II, and type III autoimmune polyglandular syndrome, multiple muscle pain rheumatism, polymyositis, post-myocardial-infarction syndrome, post-pericardiectomy syndrome, progesterone dermatitis, primary biliary cirrhosis, primary sclerosing cholangitis, psoriasis, psoriatic arthritis, idiopathic pulmonary fibrosis, gangrene pyoderma, pure red blood cell aplasia, Raynaud's phenomenon, reflex sympathetic dystrophy, Reiter's syndrome, recurrent polychondritis, restless legs syndrome, retroperitoneal fibrosis, rheumatoid fever, rheumatoid arthritis, sarcoidosis, scimitar syndrome, scleritis, scleroderma, Sjogren's syndrome, sperm and testicular autoimmunity, stiff person syndrome, subacute bacterial endocarditis (SBE), Susac's syndrome, sympathetic ophthalmitis, Takayasu's arteritis, temporal arteritis/giant-cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom macroglobulinemia (WM), and Wegener's granulomatosis (granulomatosis with polyangiitis; GPA).

The composition for preventing or treating an autoimmune disease of the present invention may contain a pharmaceutically effective amount of the compound alone or may further contain at least one pharmaceutically acceptable carrier, excipient or diluent. The term "pharmaceutically effective amount" above refers to an amount sufficient to prevent, ameliorate and treat symptoms of an autoimmune disease.

As used herein, the term "pharmaceutically acceptable" refers to a composition that is physiologically acceptable and does not usually cause allergic reactions such as gastrointestinal disorders, dizziness, or similar reactions when administered to humans. Examples of the carrier, excipient and diluent include lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oils. In addition, the composition may further contain fillers, anti-aggregating agents, lubricants, wetting agents, flavoring agents, emulsifying agents and preservatives.

In addition, the composition of the present invention may contain at least one known active ingredient having an effect of treating an autoimmune disease along with the compound.

The composition of the present invention may be formulated using a method known in the art to provide rapid, sustained or delayed release of the active ingredient after administration to a non-human mammal. The formulation may be in the form of a powder, granule, tablet, emulsion, syrup, aerosol, soft or hard gelatin capsule, a sterile injectable solution, or sterile powder.

The composition of the present invention may be administered through various routes, including oral, transdermal, subcutaneous, intravenous or intramuscular administration, and the dosage of the active ingredient depends on various factors such as the route of administration, the patient's age, gender, weight, and the severity of disease of the patient. The composition for preventing or treating an autoimmune disease according to the present invention may be administered in combination with a known compound having an effect of preventing, ameliorating or treating symptoms of autoimmune diseases.

In addition, the present invention provides a composition for preventing or treating an inflammatory disease containing the compound as an active ingredient.

As used herein, the term "inflammatory disease" refers to a disease caused by an inflammatory substance (inflammatory cytokine) such as TNFα, IL1, IL6, prostaglandin, leukotriene or NO secreted by immune cells such as macrophages due to excessive excitation of the immune system by harmful stimulation such as inflammation-inducing factors or irradiation. The "inflammatory disease" may be an acute or chronic inflammatory condition, and may be caused by an infectious or non-infectious factor.

The inflammatory disease of the present invention includes psoriasis, asthma, eczema, allergies, rheumatoid arthritis, psoriatic arthritis, contact dermatitis, atopic dermatitis, acne, atopic rhinitis, allergic dermatitis, chronic sinusitis, seborrheic dermatitis, gastritis, gout, gouty arthritis, ulcers, chronic bronchitis, pulmonary inflammation, Crohn's disease, ulcerative colitis, ankylosing spondylitis, sepsis, vasculitis, bursitis, lupus, rheumatoid polymyalgia, temporal arteritis, multiple sclerosis, solid cancer, Alzheimer's disease, arteriosclerosis, obesity and viral infections, but is not limited thereto.

In addition, non-limiting examples of the inflammatory disease include atherosclerosis, arteriosclerosis, autoimmune disorders, multiple sclerosis, systemic lupus erythematosus, multiple muscle pain rheumatism (PMR), gouty arthritis, degenerative arthritis, tendinitis, bursitis, psoriasis, cystic fibrosis, osteoarthritis, rheumatoid arthritis, inflammatory arthritis, Sjogren's syndrome, giant-cell arteritis, progressive systemic sclerosis (scleroderma), ankylosing spondylitis, polymyositis, dermatitis, pemphigus, pemphigoid, diabetes (e.g., type I), myasthenia gravis, Hashimoto's thyroiditis, Graves' disease, Goodpasture disease, mixed connective tissue disease, sclerosing cholangitis, inflammatory bowel disease, Crohn's disease, ulcerative colitis, pernicious anemia, inflammatory skin disease, usual interstitial pneumonia (UIP), asbestos disease, silicosis, bronchiectasis, beryllium poisoning, talcosis, pneumoconiosis, sarcoidosis, detachable interstitial pneumonia, lymphocytic interstitial pneumonia, giant-cell interstitial pneumonia, cellular interstitial pneumonia, exogenous allergic alveolitis, Wegener's granulomatosis and vasculitis-associated forms (temporal arteritis and polyarteritis nodosa), inflammatory skin disease, hepatitis, delayed-type hypersensitivity (e.g. poison ivy dermatitis), pneumonia, airway inflammation, adult respiratory disorder syndrome (ARDS), encephalitis, immediate hypersensitivity, asthma, hay fever, allergy, acute anaphylaxis, rheumatic fever, glomerulonephritis, pyelonephritis, cellulitis, cystitis, chronic cholecystitis, ischemia (ischemic injury), allograft rejection, host-to-transplant rejection, appendicitis, arteritis, blepharitis, bronchiolitis, bronchitis, cervicitis, cholangitis, chorionic amnionitis, conjunctivitis, psoriasis, dermatitis, endocarditis, endometritis, enteritis, intestinal inflammation, epididymitis, epididymitis, fasciitis, connective tissue infection, gastritis, gastroenteritis, gingivitis, ileitis, iritis, laryngitis, myocarditis, nephritis, omphalitis, ovaritis, orchitis, osteitis, otitis, pancreatitis, mumps, pericarditis, pharyngitis, nephritis, phlebitis, interstitial pneumonia, rectal analitis, prostatitis, rhinitis, salpingitis, sinusitis, stomatitis, synovitis, orchitis, tonsillitis, urethritis, urocystitis, uveitis, vaginitis, vasculitis, vulvitis, vulvovaginitis, vasculitis, chronic bronchiolitis, osteomyelitis, optic neuritis, temporal arteritis, transverse myelitis, cerebral fasciitis, and cerebral encephalopathy. In certain embodiments, the inflammatory disease is selected from the group consisting of atherosclerosis, arteriosclerosis, autoimmune disorders, multiple sclerosis, systemic lupus erythematosus, rheumatoid arthritis, inflammatory arthritis, and myocarditis.

As used herein, the term "treatment" means an action of stopping or delaying the progression of a disease when used for a subject having symptoms.

As used herein, the term "pharmaceutical composition" may include a pharmaceutically acceptable carrier, diluent, excipient, or a combination thereof, as needed, along with the compound of the present invention.

As used herein, the term "pharmaceutically acceptable" means a property of not impairing the biological activity and physical properties of a compound.

As used herein, the term "carrier" refers to a substance that facilitates the addition of a compound to a cell or tissue.

As used herein, the term "diluent" is defined as a substance that stabilizes the biological activity of a subject compound and is diluted in water to dissolve the compound.

Other terms and abbreviations used in the present specification may be interpreted as having meanings commonly understood by those skilled in the art to which the present invention pertains, unless otherwise defined.

Since the composition for preventing or treating an inflammatory disease includes a pharmaceutical formulation containing the compound described above as an active ingredient, content overlapping the composition of the present invention described above will be not described again in order to avoid excessive complexity of the disclosure due to the overlapping content.

In addition, the present invention provides a method for preventing or treating an autoimmune disease including administering a compound represented by TAC5, TAC5-a or TAC5-c to a subject.

In addition, the present invention provides a method for preventing or treating an inflammatory disease including administering a compound represented by TAC5, TAC5-a or TAC5-c to a subject.

In the present invention, the composition containing the compound represented by TAC5, TAC5-a or TAC5-c may further contain an appropriate carrier, excipient or diluent according to a conventional method. Examples of the carrier, excipient or diluent that may be contained in the composition containing the compound may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil.

The composition containing the compound represented by TAC5, TAC5-a or TAC5-c of the present invention may have a formulation selected from the group consisting of powders, pills, granules, capsules, suspensions, oral liquids/solutions, emulsions, syrups, sterilized aqueous solutions, non-aqueous solutions, suspensions, freeze-dried agents and suppositories according to a conventional method.

The pharmaceutical composition may be formulated using a commonly used diluent or excipient such as filler, extender, binder, wetting agent, disintegrant or surfactant. Solid formulations for oral administration may include tablets, pills, powders, granules, capsules and the like, and may be prepared by mixing the compound with at least one excipient, for example, starch, calcium carbonate, sucrose, lactose, gelatin or the like. In addition to simple excipients, lubricants such as magnesium stearate and talc may also be used. Liquid formulations for oral administration may be suspensions, oral liquids and solutions, emulsions, syrups and the like, and may contain various excipients such as wetting agents, sweeteners, fragrances, preservatives and the like, in addition to water and liquid paraffin, which are simple diluents that are commonly used. Formulations for parenteral administration may include sterilized aqueous solutions, non-aqueous solutions, suspensions, emulsions, freeze-dried preparations and suppositories. Examples of non-aqueous solutions and suspensions include propylene glycol, polyethylene glycol, vegetable oil such as olive oil, injectable esters such as ethyl oleate, and the like. Examples of the suppository base include Witepsol, macrogol, Tween 60, cacao butter, laurin butter, glycerogelatin and the like.

In addition, the pharmaceutical composition according to the present may be administered orally or parenterally (for example, intravenous, subcutaneous, intraperitoneal or topical application) depending on the desired method, and the dose (administered amount) of the pharmaceutical composition according to the present invention may vary depending on the patient's health status, weight, age, gender, diet, excretion rate, severity of disease, drug type, administration time, administration route and administration period, and may be determined by those skilled in the art. However, in order to obtain preferable effects, the pharmaceutical composition may be administered in a dose of about 0.001 to about 1000 mg/kg, specifically about 0.01 to about 100 mg/kg. The administration may be conducted once a day or divided into several doses throughout the day. Thus, the dose is not intended to limit the scope of the invention in any aspect.

Hereinafter, the present invention will be described in more detail with reference to the following examples. However, it will be obvious to those skilled in the art that the following examples are provided only for illustration of the present invention, and should not be construed as limiting the scope of the present invention based on the subject matter of the present invention.

EXAMPLE

The $^1$H and $^{13}$C NMR spectra were recorded using JNM-ECZ400S (JEOL, Japan), and the chemical shift was measured within the downfield range of ppm of the internal tetramethylsilane standard.

The multiplicity was expressed as: s (singlet); d (doublet); t (triplet); q (quartet); m (multiplet); dd (doublet of doublet); ddd (doublet of doublet of doublet); dt (doublet of triplet); td (triplet of doublet); brs (broad singlet).

The coupling constant was reported as H. Routine mass analyses were performed using an LC/MS system equipped with a reverse-phase column (C-18, 50×2.1 mm, 5 μm) and electron spray ionization (ESI).

2-amino-3-hydroxy pyridine, cesium carbonate, 3-nitrobenzyl bromide, 2-amino-3-benzyloxypyridine, bromobenzene, and 2-amino-3-benzyloxypyridine were purchased from TCI (Japan), and tin (II) chloride anhydride was purchased from Alfa Aesar (US). Copper (I) iodide and N,N'-dimethylenediamine were purchased from Sigma Aldrich (US).

The progress of the reaction was monitored using TLC (silica gel 60 F254 0.25 mm), and the components were visualized by observation under UV light (254 nm, 365 nm) or by heating after treating the TLC plate with anisaldehyde, KMnO$_4$, and phosphomolybdic acid. Unless otherwise specified, all reactions were carried out in oven-dried glassware under a dry argon atmosphere.

Preparation Example 1: Preparation of 3-((3-aminobenzyl)oxy)pyridin-2-amine (TAC5-a)

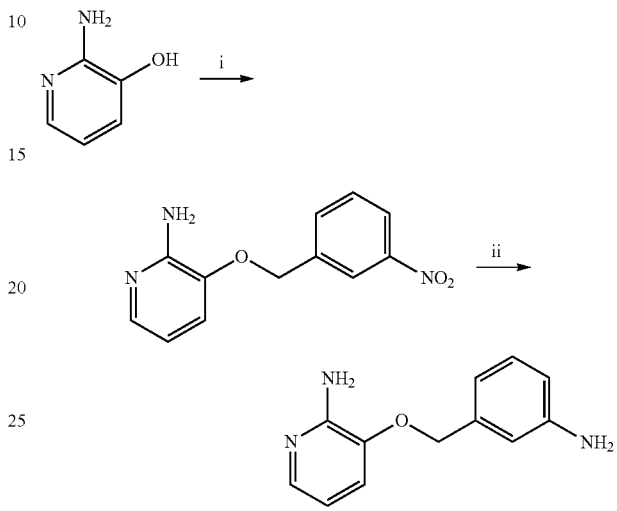

Reagents and conditions: (i) 3-nitrobenzylbromide, Cs$_2$CO$_3$, DMF, RT; (ii) SnCl$_2$, EtOH, reflux.

Step 1: Preparation of 3-((3-nitrobenzyl)oxy)-pyridin-2-amine (TAC5-a Intermediate)

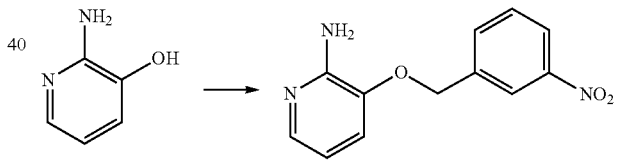

2.04 g of 2-amino-3-hydroxypyridine and 6.03 g of cesium carbonate were dissolved in 80 ml of dimethylformaldehyde (DMF). Then, a solution of 4.0 g of 3-nitrobenzyl bromide in 20 ml of dimethylformaldehyde was added to the resulting solution, and the reaction mixture was stirred at room temperature for 3 hours. After confirming completion of the reaction by TLC, saturated sodium hydrogen carbonate was added to the solution, and then the organic substance was extracted with dichloromethane three times. The obtained organic layer was dried over anhydrous sodium sulfate and filtered to obtain a solution. The obtained solution was concentrated in vacuum and then the residue was purified by silica gel flash column chromatography to obtain 2.20 g of 3-((3-nitrobenzyl)oxy)-pyridin-2-amine (48.4%).

$^1$H NMR (600 MHz, CDCl$_3$) δ 8.29 (s, 1H), 8.21 (dd, J=8.1 Hz, 1H), 7.76 (d, J=7.7 Hz, 1H), 7.70 (d, J=4.8 Hz, 1H), 7.59 (t, J=7.9 Hz, 1H), 6.95 (dd, J=7.8 Hz, 1H), 6.60 (dd, J=7.8 Hz, 1H), 5.12 (s, 2H), 4.75 (bs, 2H); $^{13}$C NMR (600 MHz, CDCl$_3$) δ 150.2, 148.5, 141.0, 139.9, 138.5, 133.4, 129.9, 123.4, 122.4, 117.0, 113.7, 69.0.

Step 2: Preparation of 3-((3-aminobenzyl)oxy)pyridin-2-amine (TAC5-a)

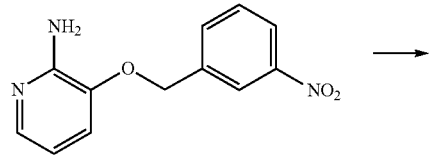

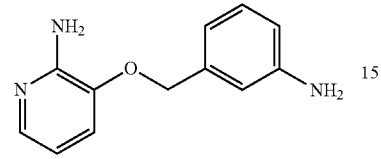

7.73 g of anhydrous tin (II) chloride was added to a solution of 0.2 ml of 1N hydrochloric acid in 40 ml of ethanol and then dissolved therein at room temperature. 2.0 g of 3-((3-nitrobenzyl)oxy)-pyridin-2-amine was added to the resulting solution and the resulting mixture was refluxed for 3 hours. After confirming the completion of the reaction through TLC, the reaction mixture was filtered using filter paper to obtain a solid mixture. The obtained solid mixture was added to saturated sodium hydrogen carbonate and dichloromethane, and the organic layer was extracted three times. The obtained organic layer was dried over anhydrous sodium sulfate and filtered to obtain a solution. The obtained solution was concentrated in vacuum to obtain 945 mg of 3-((3-aminobenzyl)oxy)pyridin-2-amine (TAC5_a) (53.9%).

$^1$H NMR (600 MHz, CDCl$_3$) δ 7.86 (dd, J=4.8 Hz, 1H), 7.70 (d, J=7.8 Hz, 2H), 7.46-7.39 (m, 5H), 7.23 (t, J=7.8 Hz, 2H), 7.07 (bs, 1H), 7.04 (dd, J=7.8 Hz, 1H), 6.69 (dd, J=7.4 Hz, 1H), 5.14 (s, 2H); $^{13}$C NMR (600 MHz, CDCl$_3$) δ 150.3, 146.9, 141.6, 139.1, 137.7, 129.7, 117.6, 116.9, 115.0, 113.9, 113.7, 70.3. LRMS (ESI) m/z calcd. For C$_{18}$H$_{17}$N$_2$O [M+H]$^+$ 277.13; found 277.15.

Preparation Example 2: Preparation of 3-((3-benzylbenzyl)oxy)pyridin-2-amine (TAC5-b)

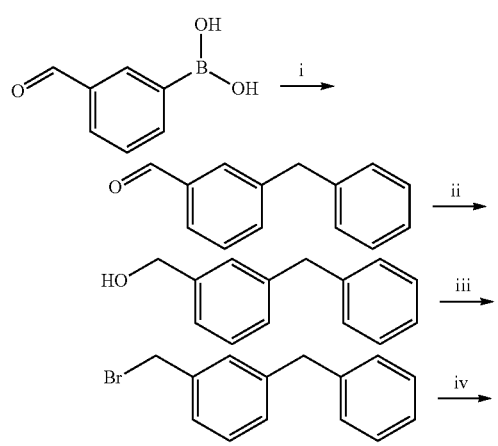

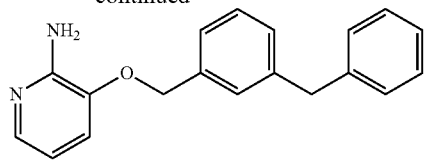

Reagents and conditions: (i) benzyl bromide, Pd(PPh$_3$)$_4$, Na$_2$CO$_3$, toluene, 80° C.; (ii) NaBH$_4$, MeOH, 0° C.; (iii) HBr, Water; CH$_2$Cl$_2$ (v:v = 1:1), RT; (iv) 2-amino-3-hydroxylpyridine, Cs$_2$CO$_3$, DMF, RT.

Step 1: Preparation of 3-benzyl benzaldehyde (TAC5-b Intermediate 1)

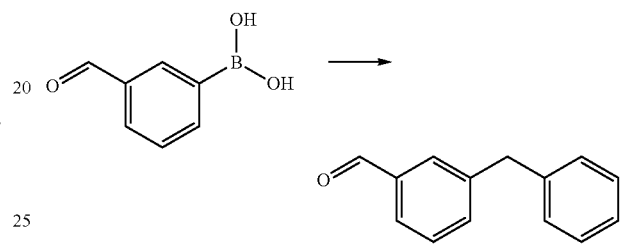

3-formylphenyl boronic acid (450 mg, 3.0 mmol) and tetrakis(triphenyl phosphine) palladium (0) (139 mg, 0.12 mmol) were added and purged with argon. Toluene (15 ml), benzyl bromide and 2N Na$_2$CO$_3$ (3 ml) were added thereto, and the resulting reaction mixture was stirred at 80° C. for 4 hours. After completion of the reaction, the reaction mixture was diluted with NaHCO$_3$ and extracted with CH$_2$Cl$_2$ three times. The combined organic layer was concentrated in vacuum. The crude product was purified by silica gel column chromatography (EA:Hex=Hex 100%-EA 15%) to obtain a product (503 mg, yield=85.3%) as a clear oil.

$^1$H NMR (600 MHz, CDCl$_3$) δ 9.86 (s, 1H), 7.63 (m, 2H), 7.23 (m, 7H), 3.95 (s, 2H); $^{13}$C NMR (150 MHz, CDCl$_3$) δ 191.9, 141.9, 139.8, 136.4, 134.7, 129.5, 128.8, 128.6, 128.4, 127.4, 126.1, 41.2.

Step 2: Preparation of (3-benzylphenyl)methanol (TAC5-b Intermediate 2)

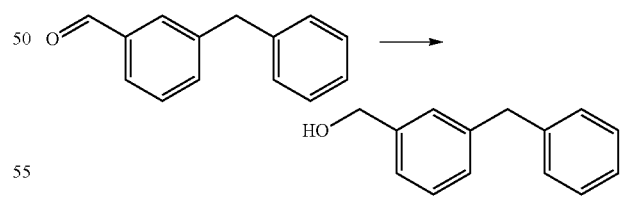

NaBH$_4$ (75 mg, 2 mmol) was added dropwise to a solution of 3-benzyl benzaldehyde (196 mg, 1.0 mmol) in methanol (10 ml) stirred at 0° C. and the resulting reaction mixture was stirred at 0° C. for 1 hour. After completion of the reaction, the reaction mixture was washed with distilled water and extracted with CH$_2$Cl$_2$ three times. The combined organic layer was concentrated in vacuum. The crude product was purified by silica gel column chromatography (EA:Hex=100%–EA 50%) to obtain a product (203 mg, quantitative yield) as a clear oil.

¹H NMR (600 MHz, CDCl₃) δ 7.13 (m, 9H), 4.41 (s, 2H), 3.89 (s, 2H), 2.89 (s, 1H); ¹³C NMR (150 MHz, CDCl₃) δ 141.2, 140.9, 140.9, 128.7, 128.4, 128.3, 127.9, 127.3, 125.9, 124.6, 64.7, 41.7.

Step 3: Preparation of 1-benzyl-3-(bromomethyl)benzene (TAC5-b Intermediate)

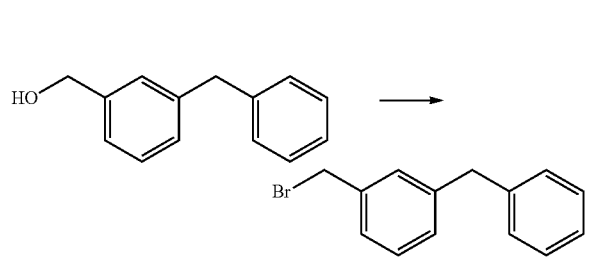

(3-benzylphenyl)methanol (198 mg, 1.0 mmol) was diluted in a mixture of DCM and HBr (5 ml, v:v=1:1) and the resulting reaction mixture was stirred at room temperature for 36 hours. After completion of the reaction, the reaction mixture was diluted with NaHCO₃ and extracted with CH₂Cl₂ three times. The combined organic layer was concentrated in vacuum. The crude product was purified by silica gel column chromatography (EA:Hex=100%–EA 10%) to obtain a product (185 mg, yield=70.8%) as a clear oil.

¹H NMR (600 MHz, CDCl₃) δ 7.17 (m, 9H), 4.36 (s, 2H), 3.92 (s, 2H); ¹³C NMR (150 MHz, CDCl₃) δ 141.6, 140.5, 137.8, 129.4, 129.0, 128.9, 128.8, 128.5, 126.8, 126.1, 41.6, 33.5.

Step 4: Preparation of 3-((3-benzylbenzyl)oxy)pyridin-2-amine (TAC5-b)

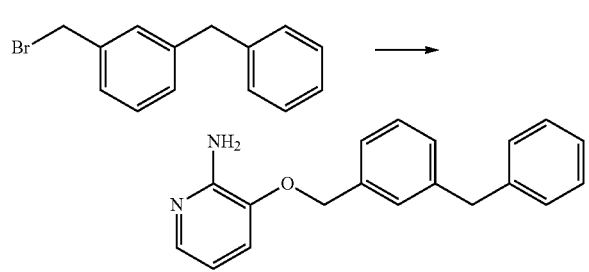

A solution of 1-benzyl-3-(bromomethyl)benzene (178 mg, 0.68 mmol) in DMF (3.8 ml) was added to a solution of 2-amino-3-hydroxypyridine (75 mg, 0.68 mmol) and Cs₂CO₃ (222 mg, 0.68 mmol) in DMF (3 ml). The resulting reaction mixture was stirred at room temperature for 2 hours. After completion of the reaction, the reaction mixture was diluted with NaHCO₃ and extracted with CH₂Cl₂ three times. The combined organic layer was concentrated in vacuum. The crude product was purified by silica gel column chromatography (EA:Hex=100%–EA 100%) to obtain a product (110 mg, yield=55.9%) as a yellow solid.

¹H NMR (600 MHz, CDCl₃) δ 7.65 (d, J=6.0 Hz, 1H), 7.21 (s, 9H), 6.88 (d, J=6.6 Hz, 1H), 6.53 (dd, J=7.8 Hz, 1H), 4.94 (s, 2H), 4.79 (bs, 2H), 3.96 (s, 2H); ¹³C NMR (150 MHz, CDCl₃) δ 150.3, 141.5, 141.3, 140.6, 138.9, 136.5, 128.8, 128.7, 128.6, 128.4, 128.0, 126.1, 125.2, 116.7, 113.3, 70.0, 41.6; LRMS (ESI) m/z calcd. for C₁₉H₁₉N₂O [M+H]⁺ 291.14; found: 291.20.

Preparation Example 3: Preparation of 3-(benzyloxy)-N-phenylpyridin-2-amine (TAC5-c)

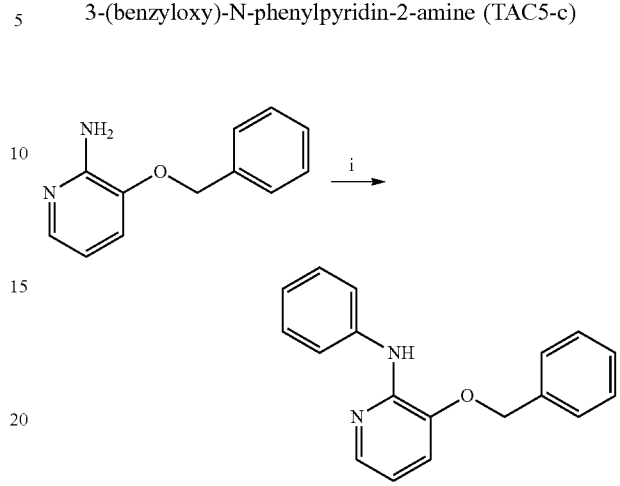

Reagents and conditions: (i) bromobenzene, CuI, DMEDA, K₂CO₃, 1,4-dioxane, 90° C..

1.0 g of 2-amino-3-benzyloxypyridine, 0.48 g of copper (I) iodide, 1.38 g of potassium carbonate, and 270 μL of N,N'-dimethylethylenediamine were dissolved in 25 ml of 1,4-dioxane. 786 μl of bromobenzene was slowly added to the resulting solution, followed by stirring at 90° C. for 17 hours. After 17 hours, the organic layer was extracted three times with saturated sodium hydrogen carbonate and dichloromethane. The obtained organic layer was dried over anhydrous sodium sulfate and filtered to obtain a solution. The obtained solution was concentrated in vacuum and the residue was purified by silica gel column chromatography to obtain 0.11 g of 3-(benzyloxy)-N-phenylpyridin-2-amine (TAC5_c).

¹H NMR (600 MHz, CDCl₃) δ 7.86 (dd, J=4.8 Hz, 1H), 7.70 (d, J=7.8 Hz, 2H), 7.46-7.39 (m, 5H), 7.23 (t, J=7.8 Hz, 2H), 7.07 (bs, 1H), 7.04 (dd, J=7.8 Hz, 1H), 6.69 (dd, J=7.4 Hz, 1H), 5.14 (s, 2H); ¹³C NMR (600 MHz, CDCl₃) δ 147.0, 141.7, 141.0, 138.9, 136.4, 129.2, 129.1, 128.7, 128.0, 121.9, 119.2, 116.6, 114.4, 70.7. LRMS (ESI) m/z calcd. For C₁₈H₁₇N₂O [M+H]⁺ 277.13; found 277.15.

Preparation Example 4: Preparation of 3-(2-ethoxy-1-phenylethoxy)pyridine-2-amine (TAC5-d)

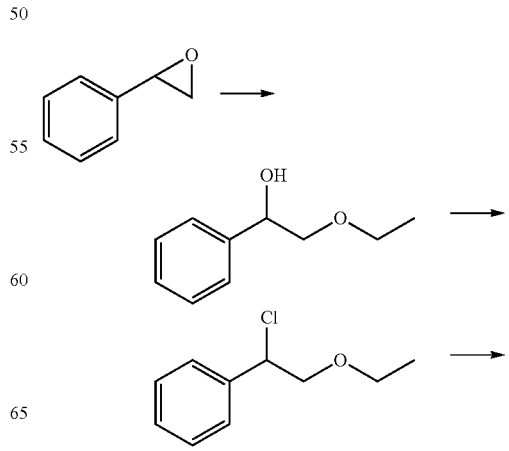

-continued

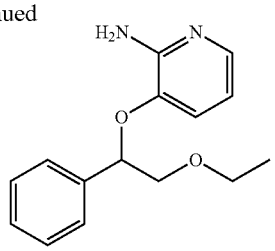

Reagents and conditions: (i) EtOH, NaOH, reflux; (ii) thionyl chloride, DCM, 0° C. to RT; (iii) Cs₂CO₃, 2-amino-3-hydroxyl pyridine, DMF, RT.

Step 1: Synthesis of 2-ethoxy-1-phenylethanol (TAC5-d Intermediate 1)

Styrene oxide (1.13 ml, 10 mmol) was added to a solution of NaOH (440 mg, 11 mmol) in EtOH (50 ml) stirred under an Ar atmosphere, and the resulting reaction mixture was refluxed for 3 hours. The reaction mixture was allowed to cool to room temperature, diluted with saturated NaHCO₃ (aq.) and extracted three times with DCM. The combined DCM layer was dried with Na₂SO₄ (s) and was concentrated in vacuum. The residue was purified by silica gel column chromatography to obtain a target product (800 mg, 48.1%) as a clear oil.

$^1$H NMR (600 MHz, CDCl₃) δ 7.36 (m, 5H), 4.88 (dd, J=9.6 Hz, 1H), 3.57 (m, 3H), 3.43 (t, J=9.0 Hz, 1H), 3.14 (s, 1H), 1.23 (t, J=6.6 Hz, 3H); $^{13}$C NMR (150 MHz, CDCl₃) δ 140.3, 128.2, 127.7, 126.1, 76.1, 72.7, 66.6, 15.0

Step 2: Synthesis of (1-chloro-2-ethoxyethyl)benzene (TAC5-d Intermediate 2)

A solution of thionyl chloride (524 μl, 7.22 mmol) in DCM (10 ml) was added to a solution of compound 4-a (1.0 g, 6.02 mmol) in DCM (15 ml) stirred at 0° C. and the resulting reaction mixture was stirred at 0° C. The reaction mixture was further stirred at 0° C. for one hour and was slowly warmed. After completion of the reaction, the reaction mixture was diluted with NaHCO₃ (aq.) and extracted three times with DCM. The combined organic layer was concentrated in vacuum. The crude product was purified by silica gel column chromatography to obtain a product (452 mg, 40.7%) as a clear oil.

$^1$H NMR (600 MHz, CDCl₃) δ 7.36 (m, 5H), 4.99 (dd, J=7.2 Hz, 1H), 3.81 (m, 2H), 3.55 (m, 2H), 1.97 (t, J=7.2 Hz, 3H); $^{13}$C NMR (150 MHz, CDCl₃) δ 138.7 128.4 128.3 127.2 75.1 66.5 61.0 14.8.

Step 3: Synthesis of 3-(2-ethoxy-1-phenylethoxy)pyridine-2-amine (TAC5-d)

Compound 4-b (200 mg, 1.08 mmol) was added to a solution of 2-amino-3-hydroxypyridine (120 mg, 1.08 mmol) and KOH (68 mg, 1.08 mmol) in DMF (5 ml), and the resulting reaction mixture was stirred at 60° C. for 4 hours. After completion of the reaction, the reaction mixture was diluted with NaHCO₃ (aq.) and extracted three times with DCM. The combined DCM layer was dried over Na₂SO₄(s) and was concentrated in vacuum. The crude product was purified by silica gel column chromatography to obtain a target product (137 mg, 49.1%) as a white solid.

$^1$H NMR (600 MHz, CDCl₃) δ 7.65 (dd, J=6.0 Hz, 1H), 7.36 (m, 5H), 6.71 (d, J=8.4 Hz, 1H), 6.39 (dd, J=7.8 Hz, 1H), 5.12 (dd, J=9.0 Hz, 1H), 5.02 (bs, 2H), 3.84 (m, 1H), 3.61 (m, 3H), 1.24 (t, J=7.2 Hz, 3H); $^{13}$C NMR (150 MHz, CDCl₃) δ 151.7, 140.4, 140.3, 137.9, 128.5, 128.1, 126.3, 121.7, 112.9, 81.5, 74.7, 66.7, 14.9; LRMS (ESI) m/z calcd. for C₁₅H₁₉N₂O₂ [M+H]⁺ 258.14; found: 259.05.

Preparation Example 5: Preparation of 3-(2-(2-aminoethoxy)-1-phenylethoxy)pyridine-2-amine (TAC5-e)

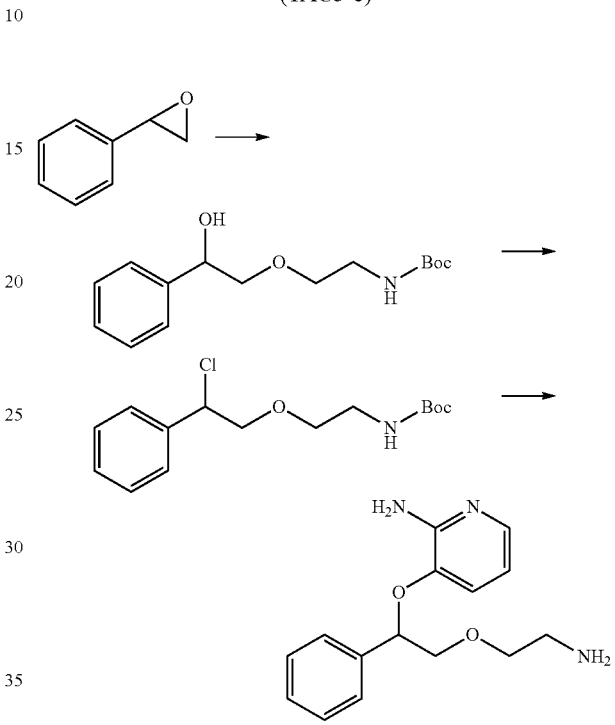

Reagents and conditions: (i) N-Boc-ethanolamine, NaH, THF, 60° C.; (ii) thionyl chloride, DCM, 0° C.; (iii) 1. Cs₂CO₃, 3-hydroxyl-2-aminopyridine, DMF, RT; 2. TFA, DCM (v:v = 1:2), RT, 4 h.

Step 1: Synthesis of tert-butyl(2-(2-hydroxy-2-phenylethoxy)ethyl)carbamate (TAC5-e Intermediate 1)

A solution of NaH (60% dispersion in mineral oil, 40 mg, 1.0 mmol) in N-Boc-ethanol amine:THF (1.0 ml, v:v=1:1) was stirred at 60° C., styrene oxide (114 μl, 1.0 mmol) was added thereto, and the resulting reaction mixture was further stirred at 60° C. overnight. After completion of the reaction, the reaction mixture was diluted with NaHCO₃(aq.) and extracted three times with DCM. The combined organic layer was dried over Na₂SO₄(s) and concentrated in vacuum. The crude product was purified by silica gel column chromatography to obtain a target product (70 mg, 24.9%) as a clear oil.

$^1$H NMR (600 MHz, CDCl₃) δ 7.36 (m, 5H), 5.04 (bs, 1H), 4.87 (dd, J=8.4 Hz, 1H), 3.58 (m, 4H), 3.32 (bs, 2H), 3.22 (s, 1H), 1.43 (s, 10H); $^{13}$C NMR (150 MHz, CDCl₃) δ 140.3, 128.3, 127.8, 126.1, 76.5, 72.7, 70.4, 40.3, 28.4.

Step 2: Synthesis of tert-butyl(2-(2-chloro-2-phenylethoxy)ethyl)carbamate (TAC5-e Intermediate 2)

Thionyl chloride (40 μl, 0.55 mmol) was added to a solution of compound 5-a (128 mg, 0.46 mmol) in DCM (4.5 ml) stirred at 0° C. and the resulting reaction mixture was stirred at 0° C. for 1.5 hours. After completion of the reaction, the reaction mixture was diluted with NaHCO₃ (aq.) and extracted three times with DCM. The combined DCM layer was dried over Na₂SO₄(s) and concentrated in vacuum. The crude product was purified by silica gel column chromatography to obtain a target product (69 mg, 50.6%) as a clear oil.

$^1$H NMR (600 MHz, CDCl₃) δ 7.36 (m, 5H), 4.97 (t, J=6.0 Hz, 1H), 4.79 (s, 1H), 3.86 (m, 2H), 3.55 (m, 2H), 3.27 (s, 2H), 1.44 (s, 10H); $^{13}$C NMR (150 MHz, CDCl₃) δ 138.5, 128.7, 128.6, 127.4, 75.5, 70.3, 60.8, 40.2, 28.4.

Step 3: Synthesis of 3-(2-(2-aminoethoxy)-1-phenylethoxy)pyridin-2-amine (TAC5-e)

A solution of Compound 5-b (69 mg, 0.24 mmol), Cs₂CO₃ (79 mg, 0.24 mmol) and 2-amino-3-hydroxylpyridine (27 mg, 0.24 mmol) in DMF (3 ml) was stirred at room temperature to 40° C. overnight. After completion of the reaction, the reaction mixture was diluted with NaHCO₃ (aq.) and extracted three times with DCM. The combined DCM layer was dried over Na₂SO₄(s) and concentrated in vacuum. The crude product was purified by silica gel column chromatography to obtain a target product. The purified product was used in subsequent reactions without further confirmation. The purified compound was stiffed in DCM:TFA (v:v=2:1) at room temperature for 4 hours. After completion of the reaction, the reaction mixture was diluted with NaHCO₃ (aq.) and extracted three times with DCM. The combined DCM layer was dried over Na₂SO₄(s). The produced filtrate was concentrated to obtain a target product (10 mg, 15.2%) as a yellow solid.

$^1$H NMR (600 MHz, CD₃OD) δ 7.43 (m, 6H), 8.86 (d, J=7.8 Hz, 1H), 6.42 (dd, J=7.8 Hz, 1H), 5.39 (dd, J=7.2 Hz, 1H), 3.93 (dd, J=10.8 Hz, 1H), 3.75 (dd, J=6.6 Hz, 1H), 3.61 (t, J=5.4 Hz, 2H), 3.35 (s, 1H), 2.81 (bs, 2H); $^{13}$C NMR (150 MHz, CD₃OD) δ 152.9, 142.1, 139.4, 139.2, 129.7, 129.4, 127.7, 121.3, 113.9, 81.5, 76.2, 73.4, 41.9.; LRMS (ESI) m/z calcd. for C₁₅H₂₀N₃O₂ [M+H]⁺ 274.15; found: 274.10.

Example 1: Establishment of QSAR (Quantitative Structure Activity Relationship) Model The overall workflow of QSAR model establishment of screening implemented by the present invention is shown in FIG. 1.

The initial major compounds of the present invention were identified using a QSAR modeling approach as disclosed in Tropsha (Tropsha, Mol Inform 29: 476-488 (2010)). Since the initial goal was to find antagonistic compounds of TLR8, a set of ligand data was prepared using several known TLR8 antagonistic compounds. The ligand data set was classified into 128 active molecules and 106 inactive molecules based on the activity data of the compounds reported in the literature. If necessary, the chemical structure was sketched and optimized using a molecular operating environment (MOE 2016) (Molecular Operating Environment (MOE 2016)(Molecular Operating Environment (MOE), 2013.08; Chemical Computing Group ULC, 1010 Sherbooke St. West, Suite #910, Montreal, QC, Canada, H3A 2R7, 2017). The QSAR model was constructed using three algorithms: k-Nearest neighbor (k-NN), random forest (RF) and support vector machine (SVM). The chemical properties of each molecule were expressed as DRAGONX-H™ or MOE descriptors. A predictive model that satisfies the statistical threshold $Q^2$ or the correct classification rate (CCR) of 0.7 was identified using three QSAR methods (k-NN, RF and SVM) (Table 2), which is suitable for rational prediction. Virtual screening was performed on a library of 2,000 molecules of chemical compounds filtered using a fingerprint-based method in a multivariate library of ~8,000,000 molecules. The top 13 compounds were selected for experimental verification of activity, and RAW 264.7 cells were cultured along with 1, 10, 50 or 100 μM of compounds to identify the most potent candidate among them. After 24 hours, MTT ((3-(4,5-dimethylthiazol-2-yl)-2,5-diphenyltetrazolium bromide) assay was performed (FIG. 2A), and TAC1, TAC3, TAC4, TACE, TACT, TAC12 and TAC13 exhibited cytotoxicity. Therefore, additional MTT assays and enzyme-linked immunosorbent assay (ELISA) were performed on TAC2, TAC5 and TAC10. The three compounds were non-cytotoxic at concentrations of 1, 10 and 50 μM, and TAC2 and TAC5 inhibited the secretion of CL075 (TLR7/8 antagonist)-induced TNF-α (FIGS. 2C and 2D). In addition, TAC5 exhibited an increased inhibitory effect compared to the inhibitory effect of TAC2 in a dose-dependent manner.

TABLE 2

| Machine learning methods | Descriptors | Prediction CCR | Accuracy | Sensitivity | Specificity |
|---|---|---|---|---|---|
| k-Nearest Neighbor | MOE 2D | 0.711 ± 0.031 | 0.748 | 0.875 | 0.547 |
| k-Nearest Neighbor | DragonX-H | 0.733 ± 0.083 | 0.766 | 0.881 | 0.585 |
| Random Forest | MOE 2D | 0.737 ± 0.057 | 0.777 | 0.632 | 0.869 |
| Random Forest | DragonX-H | 0.717 ± 0.029 | 0.732 | 0.635 | 0.809 |
| Support Vector Machine | MOE 2D | 0.773 ± 0.031 | 0.762 | 0.721 | 0.794 |
| Support Vector Machine | DragonX-H | 0.705 ± 0.043 | 0.745 | 0.594 | 0.839 |

Example 2: Effect of TAC5, TAC5-a or TAC5-c on the Activity of NF-κB and MAPK (Effect of TAC5 on CL075-Induced TLR7 and TLR8 Signaling)

Cell Culture and Preparation

RAW264.7 cells (ATCC, Manassas, Va., USA), which are mouse macrophages, were cultured in low-glucose DMEM (Thermo Fisher Scientific Inc.) supplemented with 10% FBS, 100 IU/ml penicillin and 100 μg/ml streptomycin in a culture system. Human monocyte THP1 cells were cultured in RPMI 1640 (Thermo Fisher Scientific Inc.) supplemented with 10% FBS, 100 IU/ml penicillin and 100 μg/ml streptomycin and then differentiation thereof into macrophages was induced using 10 nM phorbol 12-myristate 13-acetate (PMA) (Sigma-Aldrich Co. LLC.) for 24 hours. CL075, R848, CpG-ODN and Poly(I:C) were purchased from InvivoGen (San Diego, Calif., USA), and LPS was purchased from Sigma-Aldrich Co. (St. Louis, Mo., USA).

The following experiment was performed in order to determine the effects of TAC5 on the activity of NF-κB and MAPK.

Western Blotting of NF-κB and MAPK

In order to determine the effect of TAC5 on the activity of NF-κB and MAPK, a total-protein extraction solution (M-PER, Thermo Fisher Scientific Inc.) was mixed with a protease and phosphatase inhibitory mixture and the resulting mixture was added to a RAW 264.7 cell pellet. The pellet was cooled for 10 minutes and the lysate was centrifuged at 16000×g for 10 minutes. Then, the cytoplasmic and nuclear proteins were each extracted using NE-PER nuclear and cytoplasmic extraction reagents (Thermo Fisher Scientific Inc.) and the concentration of the proteins was measured using a BCA kit (Sigma-Aldrich Co. LLC). Then, the same amount of protein was spread on an SDS-polyacrylamide gel, and transferred to a HYBOND-ECL™ nitrocellulose membrane (Amersham Pharmacia Biotech, Inc., Piscataway, N.J., USA). The membrane was blocked with a 0.05% skim milk powder in deionized water for 1 hour, and then gently shaken overnight at a temperature of 4° C. with a primary antibody ((the primary antibody is an antibody against iNOS (BD Biosciences, San Jose, Calif., USA) and β-actin (Santa Cruz Biotechnology, Inc., Dallas, Tex., USA)) to conduct immunoblotting. After thoroughly shaking with PBST, the membrane was cultured along with an anti-mouse/-rabbit HRP-conjugated secondary antibody (Thermo Fisher Scientific Inc.) for 2 hours, proteins were detected using a SUPERSIGNAL™ West Pico ECL solution (Thermo Fisher Scientific Inc.), HDAC1 (Merck Millipore, Billerica, Mass., USA), p-NF-κB (p-p65), IκBα, p-ERK, ERK, p-JNK, JNK, p-p38, p38, and β-actin (Santa Cruz Biotechnology, Inc., Dallas, Tex., USA) proteins were visualized using the FUJI™ LAS-3000 system (Fujifilm, Tokyo, Japan), and the results are shown in FIGS. 3A-3E.

As shown in FIGS. 3A-3E, when RAW 264.7 cells which are control mouse macrophages, were treated only with CL075, IκBα was decreased due to the increased activity of NF-κB, whereas, when the RAW 264.7 cells were treated with a combination of CL075 and TAC5, the degree of degradation of IκBα and the amount of NF-κB moved to the nucleus were decreased due to the inhibited activity of NF-κB. In addition, when the cells were treated only with CL075, the activity of MAPK increased and thus ERK, JNK, and p38 were phosphorylated. However, when the cells were treated with a combination of CL075 and TAC5, the activity of MAPK was inhibited and the degree of phosphorylation of the enzymes was reduced.

The result shows that TAC5 according to the present invention inhibits the MyD88-dependent signaling pathway induced by CL075 binding to TLR7/8.

In standard in-vitro assays, among other TACs, TAC5 exhibited excellent antagonistic effects on CL075-induced activation of TLR7 and TLR8 in mouse macrophages (RAW264.7 cells). Western blot analysis showed that TAC5 inhibited CL075-induced NF-κB activation and IκBα degradation in RAW264.7 cells (FIG. 3A). TLRs are known to induce activation of c-Jun N-terminal kinase (JNK), extracellular signal-regulated kinase (ERK) and p38 mitogen-activated protein kinase (p38), as mitogen-activated protein kinases (MAPK), and regulate various cellular functions, including proliferation and apoptosis. It can be seen from the present invention that TAC5 inhibits CL075-induced activation of MAPKs, that is, phosphorylation of JNK, ERK and p38 (FIG. 3B). Then, RAW264.7 cells were cultured in CL075 or a combination of CL075 and poly(dT), and TLR8-mediated signals were elevated (Gorden, K K, et al. J Immunol 177: 8164-8170 (2006); Jurk, M., et al. Eur J Immunol 36: 1815-1826 (2006)). The result of measurement of the level of TNF-α secretion showed that TAC5 exhibits a slightly improved inhibitory effect in cells treated with a combination of CL075 and poly(dT), compared to cells treated only with CL075 (FIG. 3C). NF-κB activation induced by CL075 was confirmed through immunofluorescence staining using confocal microscopy in RAW264.7 cells. TAC5 significantly reduced the expression level of phosphorylated p65 (p-p65) and caused inactivation of NF-κB (FIG. 3D). In cells treated with TAC5 and other TLR antagonists, TAC5 exhibited moderate inhibitory effects on poly(I:C)-induced TLR3-mediated TNF-α secretion, but reduced TLR7/8-mediated TNF-α secretion in a dose-dependent manner (FIG. 3E). Meanwhile, TNF-α production did not affect cells treated with Pam3CSK4 (TLR1/2 antagonist) or LPS (TLR4 antagonist).

Example 3: TNF-α Inhibition Profile of 3-amino Derivative of TAC5 (TAC5-a)

TAC5 has a simple structure with a 2-aminopyridine functional group linked to a benzyl ring with a methoxy group (FIG. 2B). TAC5-a (3-((4-aminobenzyl)oxy)pyridin-2-amine), TAC5-b ((3-(3-benzyloxy)oxy)pyridin-2-amine)), TAC5-c (3-(benzyloxy)-N-phenylpyridin-2-amine), TAC5-d (3-(2-ethoxy-1-phenylethoxy)pyridine-2-amine) and TAC5-e (3-(2-(2-aminoethoxy)-1-phenylethoxy)pyridine-2-amine) derivatives were produced (FIG. 4A) by performing three modifications on the structure of TAC5 in order to enhance the activity thereof. Cytotoxicity in RAW 264.7 cells was tested by treatment with these compounds at a concentration of 12.5 to 50 μM. This preliminary investigation showed that TAC5-b significantly reduced cell viability, while TAC5-c showed slight cytotoxicity at 50 μM (FIG. 4B). Meanwhile, TAC5-a, TAC5-d and TAC5-e did not exhibit cytotoxic effects on cells. All of TAC5-a, TAC5-c, TAC5-d, and TAC5-e inhibited TLR7/8-mediated IL-6 expression dependently in THP-1 cells (human monocyte cell line) (FIG. 4C); Further experiments were performed using, TAC5-a, one of the compounds, at a concentration of 1 to 50 μM. The inhibitory effect of TAC5-a on TLR-mediated signaling was confirmed by measuring TNF-α secretion through ELISA in THP1-derived macrophages. As expected, TAC5-a did not block TLR4 (LPS)-, TLR1/2 (Pam3CSK4)- and TLR2/6 (FSL-1)-mediated TNF-α secretion (FIG. 4D). In addition, in order to evaluate the antagonistic effect of TAC5-a on endosomal TLR activation, cells were cultured along with this compound in the presence of R848 (TLR7/8) or CL075 (TLR7/8), imiquimod (IMQ; TLR7), TL8 (TLR8), poly(I:C) (TLR3) or CpG ODN (TLR9) (FIGS. 4E, 4F and 4G). The results showed that TAC5-a significantly inhibited TLR3-, TLR7-, TLR8- and TLR9-mediated TNF-α or IL-6 secretion in a dose-dependent manner. This suggests that TAC5-a is a potential blocker of endosomal TLR activation.

Example 4: Effects of TAC5-a on Psoriasis and SLE-Like Disease Models

The therapeutic efficacy of TAC5-a was evaluated in a psoriasis mouse model and a SLE mouse model. Psoriasis was induced in 6-7 week old C57BL/6 mice by topically applying 42 mg of IMQ cream (5%) to the shaved back skin of the mice for 6 consecutive days (FIG. 5A). TAC5-a was injected daily at doses of 50, 100 and 200 nmol/g and the effect thereof on severity was analyzed. The reversal of the degree of inflammation was evident in the back skin of TAC5-a-treated mice (FIG. 5B), but was relatively weaker than the effect of methotrexate (MTX), a chemotherapy drug. With regard to the scores using PASI (psoriasis area and severity index scores), the PASI score significantly decreased to less than 4.0 on the fourth day of treatment from 8.0 or higher (FIG. 5C). Therefore, treatment with TAC5-a adequately prevented spleen hypertrophy (FIG. 5D), which was directly correlated with the weight kinetics of the treatment group (FIG. 5E).

Histological analysis and immunochemical staining were performed on skin samples of mouse dorsal lesions. The sample was fixed with 4% paraformaldehyde solution, then embedded in paraffin and cut to 7 μm on a glass slide. The sections were stained with hematoxylin and eosin (H&E) and the thickness of the dermis and epidermis were measured. The thickness of skin was measured with a Leica DMi8 fluorescence microscope using a Leica LAS X Hardware Configurator (Leica Microsystems GmbH, Wetzlar, Germany). IMQ-mediated skin inflammation was evaluated by immunohistochemistry (IHC) using a primary antibody that recognizes CD68 (ab31630, 1:200 dilution) as a macrophage marker. The result of measurement of the thickness of the epidermis and the dermis of the TAC5-a and MTX (positive control group) groups showed that therapeutic effects similar to those of the treatment group were observed (FIG. 5F). The skin was stained with hematoxylin and eosin (H&E) in order to evaluate the thickness of the epidermis (yellow arrow) and dermis (green arrow) in IMQ-induced psoriasis mice and thereby to observe the histopathological changes of skin lesions in each group (FIG. 5G). Immunohistochemical analysis of skin lesions in each group was performed using a primary antibody that recognizes CD68. TAC5-a effectively reduced the expression of CD68 (brown) (FIG. 5H). The therapeutic effect of TAC5-a on the SLE disease model could also be clearly observed through appearance evaluation or size decrease of the swollen lymph node (FIG. 6A).

Quantitative Real-Time PCR (qRT-PCR)

QRT-PCR analysis was performed to detect the expression levels of specific genes in lymph nodes, spleen and kidney. Total RNA was isolated from lymph nodes, spleen and kidneys of 16-week-old mice using TRI reagent (Sigma-Aldrich, Co.). RNA was applied to qRT-PCR based on SYBR green (Enzo Life Sciences, Inc., Farmingdale, N.Y., USA). The following primers for the marker gene were used: mTLR7, 5'-ATG TGG ACA CGG AAG AGA CAA-3'(SEQ ID NO: 1) and 5'-GGT AAG GGT AAG ATT GGT G-3'(SEQ ID NO: 2); mTLR9, 5'-ATG GTT CTC CGT CGA AGG ACT-3' (SEQ ID NO: 3) and 5'-GAG GCT TCA GCT CAC AGG G-3'(SEQ ID NO: 4); mIL-6, 5'-GAG GAT ACC ACT CCC AAC AGA CC-3'(SEQ ID NO: 5) and 5'-AAG TGC ATC ATC GTT GTT CAT ACA-3'(SEQ ID NO: 6); mMyd88, 5'-CAC CTG TGT CTG GTC CAT TG-3'(SEQ ID NO: 7) and 5'-CTG TTG GAC ACC TGG AGA CA-3'(SEQ ID NO: 8); mIL-17, 5'-GCT CCA GAA GGC CCT CAG A-3' (SEQ ID NO: 9) and 5'-AGC TTT CCC TCC GCA TTG A-3'(SEQ ID NO: 10); mGAPDH, 5'-CTC AAC ACG GGA AAC CTC AC-3' (SEQ ID NO: 11) and 5'-CGC TCC ACC AAC TAA GAA CG-3'(SEQ ID NO: 12) (Bioneer, Daejeon, Korea). Quantified individual RNA expression levels were normalized to GAPDH and expressed as RNA expression levels relative to the corresponding wild-type mice.

The therapeutic potential of TAC5-a on systemic autoimmunity was further determined by intraperitoneally injecting 10 nmol/g (daily dosage) of TAC5-a (dissolved in 1% dimethylsulfoxide [DMSO]) into MARC/lpr mice for 11 days. This inhibitor clearly influenced mouse lymphatic proliferation. Lymphocyte swelling in TAC5-a-treated mice was significantly prevented in vehicle-treated mice (FIG. 6A). The production of anti-dsDNA autoantibodies was kept low (FIG. 6B), and serum antinuclear antibodies (ANAs) were reduced by treatment with inhibitors (FIG. 6C). The detection of certain proteins, such as albumin, in the urine serves as a marker for a kidney pathology called glomerulonephritis (GN), which is caused by inflammation of the glomerulus. As shown in FIG. 6D, the content of urine albumin was significantly reduced by treatment with TAC5-a, which indicates therapeutic efficacy for GN expression. Then, the effect of TAC5-a on the relative expression behaviors of specific genes in lymph nodes, spleen and kidneys at the transcription level was confirmed. TAC5-a significantly reduced TLR7, IL-17 and IL-6 mRNA levels in lymph nodes (FIGS. 6E to 6G). Expression of TLR7, TLR9 and MyD88 mRNA was observed in the spleen (FIGS. 6H to 6J) and expression of TLR7 and IL-17 was observed in the kidney (FIGS. 6K to 6L). This means that, as shown in FIG. 6A, the prevention of lymph node swelling may be caused by down-regulation of proinflammatory cytokines.

Example 5: Prediction of TAC5-a Binding Mode in TLR7/8

Figure 7E:
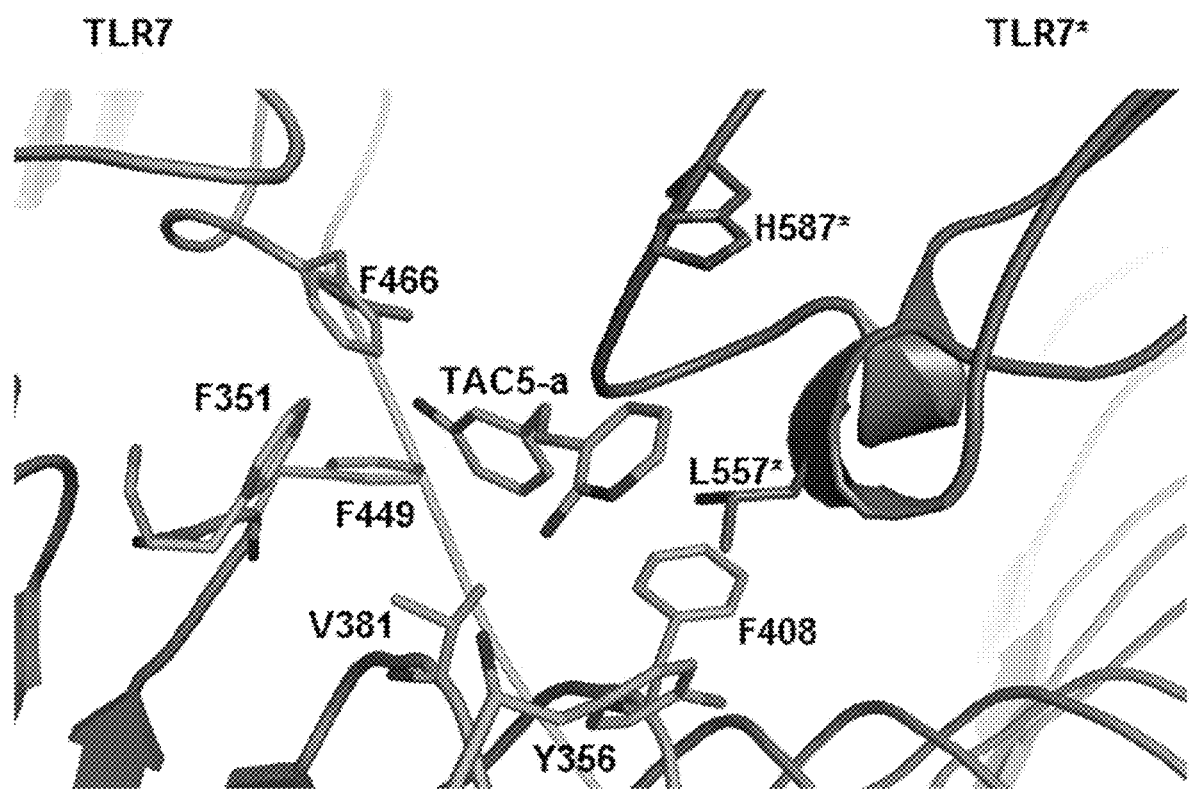
Figure 7F:
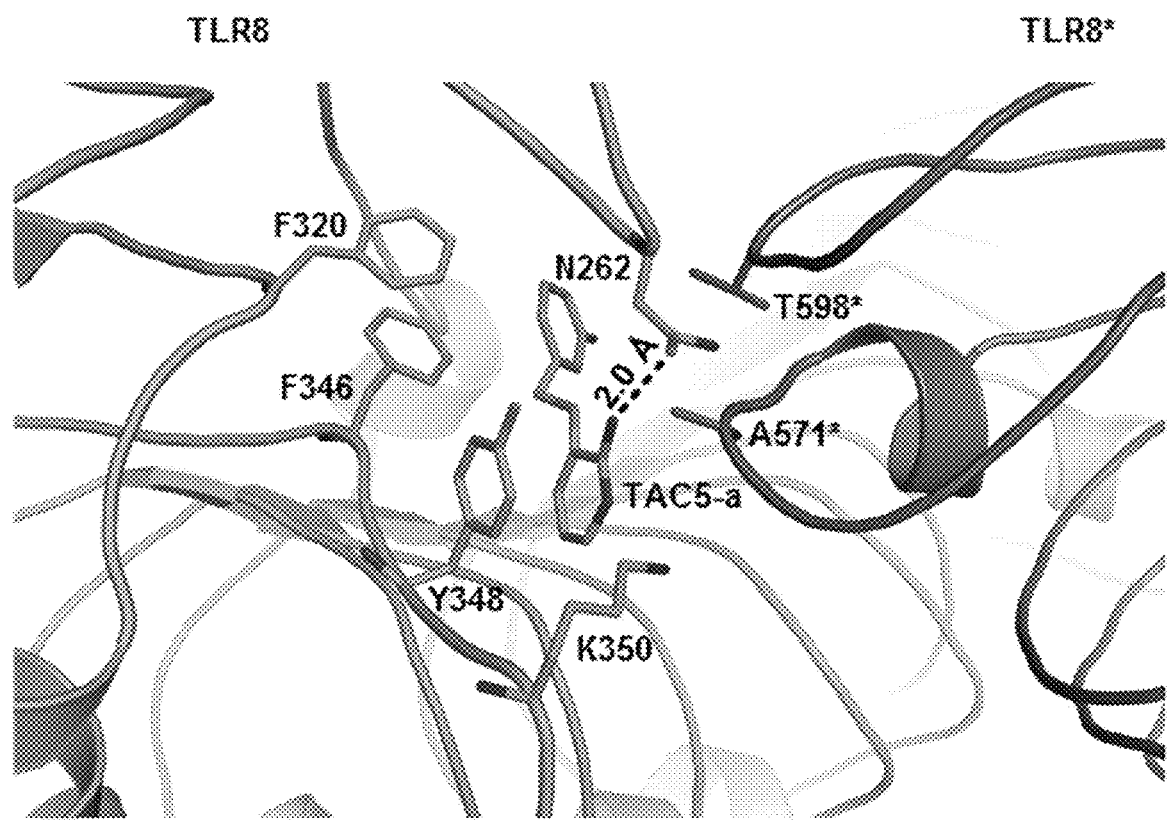

After confirming in-vitro and in-vivo efficacy of TAC5-a, the binding modes and interaction patterns thereof with TLR7 and TLR8 were predicted. The sites of agonist/antagonist binding to these receptors are well defined through X-ray crystallography research. The chemical structure of TAC5-a was docked with representative low energy forms of TLR7 and TLR8. Analysis of the topmost docked pose showed that the inhibitor stably occupies the cavity present in the lateral junction between the two subunits (FIGS. 7A to 7D), and forms primarily hydrophobic contacts with adjacent amino acids. The 2-amino pyridine ring interacts with F408 through π-interaction, and the phenylamine group is stacked in the hydrophobic region defined by F466, F351 and F449 of TLR7 (FIG. 7E). Similarly, the 2-amino-pyridine ring has a π-stacking interaction with Y348 and the amino group thereof forms a hydrogen bond between 2-A and N262 of TLR8. Hydrophobic interactions were also observed between the phenylamine group of TAC5-a and TLR8 residue, F320 and F346 (FIG. 7F). This indicates that the antagonistic activity of TAC5-a may be primarily caused by the hydrophobic ring stabilizing the entire structure inside the polar-aromatic small molecule binding cavity of TLR7/8.

INDUSTRIAL APPLICABILITY

The novel compounds represented by TAC5 and derivatives thereof, TAC5-a or TAC5-c, according to the present invention prevent TNFα secretion, NFkB activation, IkB (nuclear factor kappa-light-chain-enhancer of activated B cell) degradation, and phosphorylation of MAPKs (p38, c-Jun N-terminal kinase and extracellular signal-regulated kinase), which are induced by poly(I:C) (TLR3 agonist), IMQ (TLR7 agonist), CL075 (TLR7/8 agonist), R848 (TLR7/8 agonist), TL8 (TLR8 agonist) or CpG ODN (TLR9 agonist), and inhibit the production of inflammatory cytokines, thereby exhibiting an potent effect as a composition for preventing or treating TLR3/7/8/9-related autoimmune diseases and inflammatory diseases, in particular, including systemic lupus erythematosus and psoriasis.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

The invention claimed is:

1. A compound represented by any one selected from Formulas 1-2 to 1-9 or a pharmaceutically acceptable salt thereof:

[Formula 1-2]

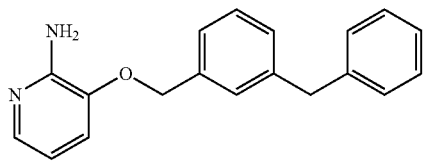

[Formula 1-3]

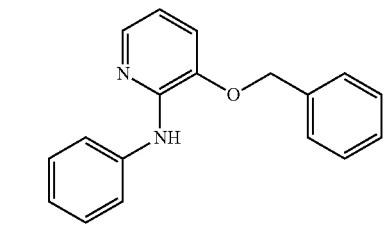

[Formula 1-4]

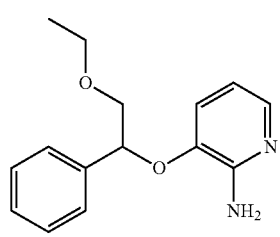

[Formula 1-5]

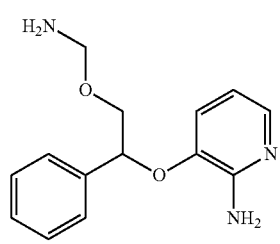

[Formula 1-6]

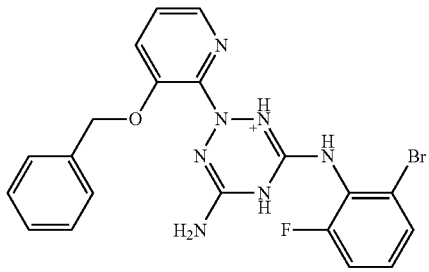

[Formula 1-7]

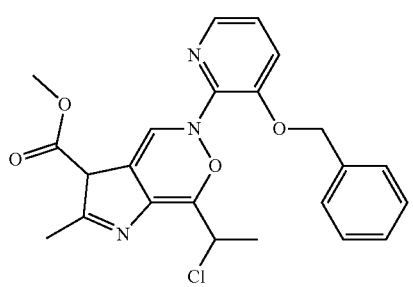

[Formula 1-8]

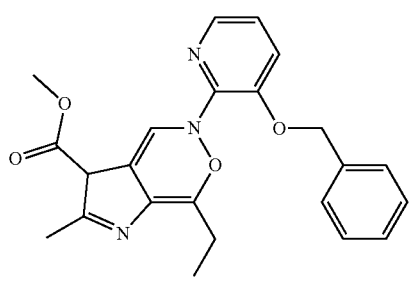

[Formula 1-9]

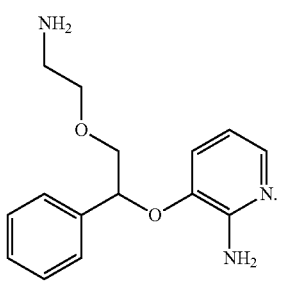

2. A method of preparing a compound of Formula 1-3 comprising reacting a solution of 2-amino-3-benzyloxypyridine, copper (I) iodide, potassium carbonate and N,N'-dimethylethylenediamine with bromobenzene to synthesize 3-(benzyloxy)-N-phenylpyridin-2-amine

[Formula 1-3]

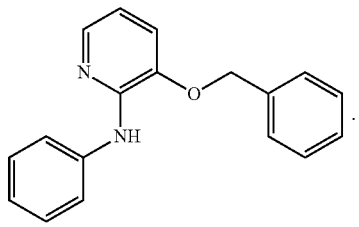

3. A method of treating an autoimmune disease or an inflammatory disease in a subject in need thereof, comprising administering an effective amount of a pharmaceutical composition comprising the compound or a pharmaceutically acceptable salt thereof of claim 1 as an active ingredient to the subject.

4. The method of treating an autoimmune disease or an inflammatory disease of claim 3, wherein the autoimmune disease or inflammatory disease is selected from the group consisting of psoriasis, systemic lupus erythematosus (SLE), skin rash, photosensitivity, arthritis, oral ulcer, nephritis, hemocytopenia, vasculitis, serositis, inflammatory bowel disease (IBD), diabetes, multiple sclerosis, skin sclerosis, pemphigus, atopic dermatitis, urethritis, cystitis, arteriosclerosis, allergic disease, rhinitis, asthma, acute pain, chronic pain, periodontitis, gingivitis, gout, myocardial infarction, congestive heart failure, high blood pressure, angina pectoris, gastric ulcer, cerebral infarction, Down's syndrome, multiple sclerosis, obesity, dementia, depression, schizophrenia, tuberculosis, sleep disorders, sepsis, burns, pancreatitis, Parkinson's disease, and stroke.

5. The method of treating an autoimmune disease or an inflammatory disease of claim 3, wherein the composition further comprises a pharmaceutically acceptable carrier, excipient or diluent.

* * * * *